(12) United States Patent
Khachaturian et al.

(10) Patent No.: US 9,721,339 B2
(45) Date of Patent: *Aug. 1, 2017

(54) DEVICE HAVING DIGITAL INFRARED SENSOR AND NON-TOUCH OPTICAL DETECTION OF AMPLIFIED TEMPORAL VARIATION OF VITAL SIGNS

(71) Applicants: Mark Khachaturian, Boca Raton, FL (US); Michael G. Smith, Austin, TX (US)

(72) Inventors: Mark Khachaturian, Boca Raton, FL (US); Michael G. Smith, Austin, TX (US)

(73) Assignee: Arc Devices, LTD, Galway (IE)

( * ) Notice: Subject to any disclaimer, the term of this patent is extended or adjusted under 35 U.S.C. 154(b) by 206 days.

This patent is subject to a terminal disclaimer.

(21) Appl. No.: 14/457,001

(22) Filed: Aug. 11, 2014

(65) Prior Publication Data

US 2016/0004910 A1   Jan. 7, 2016

Related U.S. Application Data

(63) Continuation of application No. 14/324,235, filed on Jul. 6, 2014.

(30) Foreign Application Priority Data

Jul. 4, 2014 (GB) .................................. 1411983.8

(51) Int. Cl.
   *G06K 9/00* (2006.01)
   *G06T 7/00* (2017.01)
   (Continued)

(52) U.S. Cl.
   CPC .......... *G06T 7/0012* (2013.01); *A61B 5/0008* (2013.01); *A61B 5/0013* (2013.01);
   (Continued)

(58) Field of Classification Search
   None
   See application file for complete search history.

(56) References Cited

U.S. PATENT DOCUMENTS

4,315,150 A   2/1982   Darringer et al.
4,322,012 A   3/1982   Conti
(Continued)

FOREIGN PATENT DOCUMENTS

DE   19827343 A1   12/1999
EP   2045590 A1   4/2009
(Continued)

OTHER PUBLICATIONS

Bai, J., et al., "Selectively de-animating video," ACM Transactions on Graphics, (2012).
(Continued)

*Primary Examiner* — Shefali Goradia
(74) *Attorney, Agent, or Firm* — Michael G Smith, Esq.

(57) ABSTRACT

A microprocessor is operably coupled to a camera from which patient vital signs are determined and a digital infrared sensor. A temporal variation of images from the camera is generated and amplified from which the patient vital signs, such as heart rate or respiratory rate, can be determined and displayed or stored and temperature is determined from digital infrared sensor.

20 Claims, 28 Drawing Sheets

(51) Int. Cl.

| | | |
|---|---|---|
| A61B 5/026 | (2006.01) | |
| G01J 5/32 | (2006.01) | |
| G01J 5/02 | (2006.01) | |
| G01J 5/08 | (2006.01) | |
| A61B 5/00 | (2006.01) | |
| A61B 5/01 | (2006.01) | |
| G06T 5/20 | (2006.01) | |
| A61B 5/0205 | (2006.01) | |
| A61B 5/0402 | (2006.01) | |
| A61B 5/1455 | (2006.01) | |
| G06K 9/46 | (2006.01) | |
| G06K 9/62 | (2006.01) | |
| G06T 7/20 | (2017.01) | |
| G06T 3/40 | (2006.01) | |
| G06T 5/10 | (2006.01) | |
| G06F 19/00 | (2011.01) | |
| G01J 5/30 | (2006.01) | |
| H04N 5/33 | (2006.01) | |
| G01K 1/02 | (2006.01) | |
| G01K 13/00 | (2006.01) | |
| G06F 3/042 | (2006.01) | |
| H04N 5/378 | (2011.01) | |
| G06T 5/00 | (2006.01) | |
| G06T 7/13 | (2017.01) | |
| G06T 7/90 | (2017.01) | |
| G01J 5/00 | (2006.01) | |
| A61B 5/021 | (2006.01) | |
| A61B 5/024 | (2006.01) | |
| A61B 5/08 | (2006.01) | |

(52) U.S. Cl.
CPC .......... *A61B 5/0059* (2013.01); *A61B 5/0064* (2013.01); *A61B 5/0075* (2013.01); *A61B 5/0077* (2013.01); *A61B 5/01* (2013.01); *A61B 5/015* (2013.01); *A61B 5/02055* (2013.01); *A61B 5/0261* (2013.01); *A61B 5/0402* (2013.01); *A61B 5/14551* (2013.01); *A61B 5/14552* (2013.01); *A61B 5/441* (2013.01); *A61B 5/6898* (2013.01); *A61B 5/725* (2013.01); *A61B 5/7225* (2013.01); *A61B 5/7257* (2013.01); *A61B 5/7264* (2013.01); *A61B 5/7267* (2013.01); *A61B 5/7275* (2013.01); *A61B 5/7278* (2013.01); *A61B 5/742* (2013.01); *A61B 5/743* (2013.01); *A61B 5/7425* (2013.01); *G01J 5/0025* (2013.01); *G01J 5/025* (2013.01); *G01J 5/0893* (2013.01); *G01J 5/30* (2013.01); *G01J 5/32* (2013.01); *G01K 1/02* (2013.01); *G01K 13/004* (2013.01); *G06F 3/042* (2013.01); *G06F 19/3406* (2013.01); *G06K 9/00221* (2013.01); *G06K 9/00241* (2013.01); *G06K 9/00268* (2013.01); *G06K 9/00288* (2013.01); *G06K 9/00456* (2013.01); *G06K 9/00624* (2013.01); *G06K 9/00711* (2013.01); *G06K 9/46* (2013.01); *G06K 9/4604* (2013.01); *G06K 9/6218* (2013.01); *G06T 3/40* (2013.01); *G06T 5/00* (2013.01); *G06T 5/10* (2013.01); *G06T 5/20* (2013.01); *G06T 7/0016* (2013.01); *G06T 7/13* (2017.01); *G06T 7/20* (2013.01); *G06T 7/90* (2017.01); *H04N 5/33* (2013.01); *H04N 5/378* (2013.01); *A61B 5/021* (2013.01); *A61B 5/024* (2013.01); *A61B 5/02416* (2013.01); *A61B 5/02433* (2013.01); *A61B 5/0816* (2013.01); *A61B 2560/0214* (2013.01); *A61B 2560/0475* (2013.01); *A61B 2576/00* (2013.01); *G01J 2005/0077* (2013.01); *G06K 2009/4666* (2013.01); *G06T 2207/10004* (2013.01); *G06T 2207/10016* (2013.01); *G06T 2207/10048* (2013.01); *G06T 2207/20024* (2013.01); *G06T 2207/20076* (2013.01); *G06T 2207/20132* (2013.01); *G06T 2207/30004* (2013.01); *G06T 2207/30088* (2013.01); *G06T 2207/30104* (2013.01); *G06T 2207/30201* (2013.01); *G06T 2210/22* (2013.01)

(56) References Cited

U.S. PATENT DOCUMENTS

| | | | |
|---|---|---|---|
| 4,602,642 | A | 7/1986 | O'Hara et al. |
| 5,150,969 | A | 9/1992 | Goldberg et al. |
| 5,368,038 | A | 11/1994 | Fraden |
| 5,743,644 | A | 4/1998 | Kobayashi |
| 6,095,682 | A | 8/2000 | Hollander et al. |
| 6,292,685 | B1 | 9/2001 | Pompei |
| 6,358,216 | B1 | 3/2002 | Kraus et al. |
| 6,742,927 | B2 | 6/2004 | Bellifemine |
| 6,751,342 | B2 * | 6/2004 | Shepard ............... G01N 25/72 250/332 |
| 6,757,412 | B1 * | 6/2004 | Parsons ................. G06T 7/0012 128/922 |
| 7,339,685 | B2 | 3/2008 | Carlson et al. |
| 7,346,386 | B2 | 3/2008 | Pompei |
| 7,520,668 | B2 | 4/2009 | Chen |
| 7,572,056 | B2 | 8/2009 | Lane |
| 7,787,938 | B2 | 8/2010 | Pompei |
| 8,452,382 | B1 | 5/2013 | Roth |
| 8,517,603 | B2 | 8/2013 | Fraden |
| 8,617,081 | B2 | 12/2013 | Mestha et al. |
| 8,950,935 | B1 * | 2/2015 | Khachaturian ........ A61B 5/742 374/121 |
| 2002/0172410 | A1 * | 11/2002 | Shepard ................ G01N 25/72 382/141 |
| 2004/0013162 | A1 | 1/2004 | Beerwerth |
| 2005/0023991 | A1 | 2/2005 | Kemper |
| 2007/0183475 | A1 | 8/2007 | Hutcherson |
| 2008/0175301 | A1 | 7/2008 | Chen |
| 2009/0141124 | A1 | 6/2009 | Liu et al. |
| 2009/0172591 | A1 | 7/2009 | Pomper |
| 2009/0175317 | A1 | 7/2009 | Chan et al. |
| 2009/0221880 | A1 | 9/2009 | Soderberg et al. |
| 2011/0112791 | A1 * | 5/2011 | Pak ....................... A61B 1/227 702/131 |
| 2011/0199203 | A1 | 8/2011 | Hsu |
| 2011/0228811 | A1 | 9/2011 | Fraden |
| 2011/0251493 | A1 | 10/2011 | Poh et al. |
| 2011/0286644 | A1 | 11/2011 | Kislal |
| 2012/0130251 | A1 | 5/2012 | Huff |
| 2012/0130252 | A1 | 5/2012 | Pohjanen et al. |
| 2012/0150482 | A1 | 6/2012 | Yildizyan et al. |
| 2012/0242844 | A1 | 9/2012 | Walker et al. |
| 2013/0245462 | A1 | 9/2013 | Capdevila et al. |
| 2013/0271591 | A1 | 10/2013 | Van Leest et al. |
| 2014/0003461 | A1 | 1/2014 | Roth |
| 2014/0003462 | A1 | 1/2014 | Roth |
| 2014/0064327 | A1 | 3/2014 | Roth |
| 2014/0064328 | A1 | 3/2014 | Roth |
| 2014/0064333 | A1 | 3/2014 | Roth |
| 2014/0072190 | A1 * | 3/2014 | Wu ....................... G06T 7/2053 382/128 |
| 2014/0072228 | A1 | 3/2014 | Rubinstein |
| 2014/0072229 | A1 | 3/2014 | Wadhwa |
| 2014/0088434 | A1 | 3/2014 | Roth |
| 2014/0088435 | A1 | 3/2014 | Roth |
| 2014/0088436 | A1 | 3/2014 | Roth |
| 2014/0112367 | A1 | 4/2014 | Roth |
| 2014/0114600 | A1 | 4/2014 | Roth |
| 2016/0073897 | A1 * | 3/2016 | Khachaturian ........ A61B 5/01 600/408 |

(56) References Cited

U.S. PATENT DOCUMENTS

FOREIGN PATENT DOCUMENTS

| EP | 2674735 A1 | 12/2013 |
|---|---|---|
| GB | 1322906.7 | 7/1973 |
| GB | 2291498 A | 1/1996 |
| WO | 9202792 A1 | 2/1992 |
| WO | 9801730 A1 | 1/1998 |
| WO | 9939166 A1 | 8/1999 |
| WO | 9967611 A1 | 12/1999 |

OTHER PUBLICATIONS

Balakrishnan, Guha, Fredo Durand, and John Guttag. "Detecting pulse from head motions in video." Computer Vision and Pattern Recognition (CVPR), 2013 IEEE Conference on. IEEE, 2013.
Bojanic, S., et al., "Ocular microtremor: a tool for measuring depth of anaesthesia?" British J. Anaestheia, 86(4): 519-522 (2001).
Burt, P. and Adelson, E., "The laplacian pyramid as a compact image code," IEEE Trans. Comm., 31(4): 532-540 (1983).
Covidien, Filac 3000 EZ-EZA Electronic Thermometer Operating Manual, 2012, http://www.covidien.com/imageServer.aspx?contentID=31819&contenttype=application/pdf, retrieved from the Internet on July 24, 2015.
Fleet, D.J. and Jepson, A.D., "Computation of component image velocity from local phase information," Int. J. Comput., Vision 5(1): 77-104 (Sep. 1990).
Freeman, W.T., et al., "Motion without movement," SIGGRAPH Comput. Graph., 25: 27-30 (Jul. 1991).
Fuchs, M., et al., "Real-time temporal shaping of high-speed video streams," Computers & Graphics, 34(5): 575-584 (2010).
Gautama, T. and Van Hulle, M., "A phase-based approach to the estimation of the optical flow field using spatial filtering", Neural Netlvorks, IEEE Transactions, 13(5): 1127-1136 (Sep. 2002).
Liu, C., et al., "Motion magnification", ACAM Trans. Graph., 24: 519-526 (Jul. 2005).
Lucas, Bruce D., and Takeo Kanade. "An iterative image registration technique with an application to stereo vision." IJCAI. vol. 81.1981.
Ming-Zher Poh et al. Non-contact, automated cardiac pulse measurements using video imaging and blind source separation, Optics Express, 18(10): 10762-10?74, 2010.
Portilla, J. and Simoncelli, E.D., "A parametric texture model based on joint statistics of complex wavelet coefficients," Int. J. Comput. Vision, 49(1 ): 49-70 (Oct. 2000).
Rolfs, M., "Microsaccades: Small steps on a long way," Vision Res., 49(20): 2415-2441 (2009).
Rubinstein, M, "Eulerian Video Magnification" You Tube, http://www.youtube.com/watch?v=ONZcjs1Pjmk, May 23, 2012, 3 pages.
Rubinstein, M., et al., "Motion denoising with application to time-lapse photography," IEEE Computer Vision and Pattern Recognition, CVPR, pp. 313-320 (Jun. 2011).
Simoncelli, E.P. and Freeman, W.T., The steerable pyramid: a flexible architecture for multiscale derivative computation, in Proc. of the 1995 Int'l Conf. on Image Proc., IEEE Computer Society,ICIP, Washington, DC, USA, 3:3444 (1995).
Timoner Samson J. Subpixel motion estimation from sequences of video images. Diss. Massachusetts Institute of Technology, 1999.
Timoner Samson J., and Dennis M. Freeman. "Multi-image gradient-based algorithms for motion estimation." Optical engineering 40.9 (2001 ): 2003-2016.
Unuma Munetoshi, Ken Anjyo, and Ryozo Takeuchi. "Fourier principles for emotion-based human figure animation." Proceedings of the 22nd annual conference on Computer graphics and interactive techniques. ACM, 1995.
Verkruysse, Wim, Lars 0. Svaasand, and J. Stuart Nelson. "Remote plethysmographic imaging using ambient light." Optics express 16.26 (2008): 21434-21445.

Viola Paul, and Michael J. Jones. "Robust real-time face detection." International journal of computer vision 57.2 (2004): 137-154.
Wadhwa, Neal, et al. "Phase-based video motion processing." ACM Transactions on Graphics (TOG) 32.4 (2013): 80.
Wadhwa, Neal, et al. "Riesz pyramids for fast phase-based video magnification." Computational Photography (ICCP), 2014 IEEE International Conference on. IEEE, 2014.
Wang J., et al., "The cartoon animation filter," ACM Trans. Graph., 25: 1169-1173 (2006).
Wu, H.-Y., et al., "Eulerian video magnification for revealing subtle changes in the world," ACM Trans. Graph. (Proc. SIGGRAPH), 31 (Aug. 2012).
Hao-Yu Wu, Eulerian Video Magnification for Revealing Subtle Changes in the World, ACM Transactions on Graphics (TOG)—SIGGRAPH 2012 Conference Proceedings, vol. 31 Issue 4, Jul. 2012, Article No. 65, ACM New York, NY, USA, ISSN: 0730-0301 EISSN: 1557-7368 doi 10.1145/2185520.2185561, published on Jul. 1, 2012, retrieved from the Internet on Jul. 9, 2014 from http://people.csail.mit.edu/billf/publications/Eulearian_Video_Magnification.pdf.
Eduardo S.L. Gastal, Adaptive Manifolds for Real-Time High-Dimensional Filtering, ACM Transactions on Graphics (TOG)—SIGGRAPH 2012 Conference Proceedings, vol. 31 Issue 4, Jul. 2012, Article No. 33, ACM New York, NY, USA, ISSN: 0730-0301 EISSN: 1557-7368, doi10.1145/2185520.2185529, retrieved from the Internet on on Jul. 9, 2013 from http://inf.ufrgs.br/~eslgastal/AdaptiveManifolds/Gastal_Oliveira_SIGGRAPH2012_Adaptive_Manifolds.pdf.
Sunghyun Cho, Video deblurring for hand-held cameras using patch-based synthesis, ACM Transactions on Graphics (TOG)—SIGGRAPH 2012 Conference Proceedings, vol. 31 Issue 4, Jul. 2012, Article No. 64, ACM New York, NY, USA, ISSN: 0730-0301 EISSN: 1557-7368 doi 10.1145/2185520.2185561, published on Jul. 1, 2012, retrieved from the Internet on Jul. 9, 2014 from http://juew.org/publication/video_deblur.pdf.
C. Liu, Motion magnification, ACM SIGGRAPH 2005, pp. 519-526, 2005, retrieved from the Internet on Jul. 9, 2014 fromhttp://people.csail.mit.edu/celiu/pdfs/motionmag.pdf.
O. Arikan, Interactive Motion Generation from Examples, ACM Transactions on Graphics (TOG), Proceedings of ACM SIGGRAPH 2002, vol. 21 Issue 3, Jul. 2002, pp. 483-490, ACM New York, NY, USA, ISBN:1-58113-521-1, doi 10.1145/566654.566606, retrieved from the Internet on Jul. 9, 2014from http://www.okanarikan.com/Papers/SynthesisFromExamples/paper.pdf.
wikipedia.com, Category: Data Clustering Algorithms, retrieved from the Internet on Jun. 17, 2014 at http://en.wikipedia.org/wiki/Category:Data_clustering_algorithms.
wikipedia.com, Filter (signal processing), retrieved from the Internet on Jun. 17, 2014 at http://en.wikipedia.org/wiki/Filter_(signal_processing).
R Fisher. S. Perkins. A. Walker and E. Wolfart, Frequency Filter, Image Processing Learning Resources, 2003, retrieved from the Internet on Jun. 24, 2014 at http://homepages.inf.ed.ac.uk/rbf/HIPR2/freqfilt.htm.
wikipedia.com, Band-pass filter, retrieved from the Internet on Jul. 7, 2014 at http://en.wikipedia.org/wiki/Band-pass_filter.
wikipedia.com, Low-pass filter, retrieved from the Internet on Jul. 7, 2014 at http://en.wikipedia.org/wiki/Low-pass_filter.
wikipedia.com, High-pass filter, retrieved from the Internet on Jul. 7, 2014 at http://en.wikipedia.org/wiki/High-pass_filter.
R Fisher. S. Perkins. A. Walker and E. Wolfart, Fourier Transform, Image Processing Learning Resources, 2003, retrieved from the Internet on Jul. 7, 2014 at http://homepages.inf.ed.ac.uk/rbf/HIPR2/fourier.htm.
wikipedia.com, Expectation-maximization algorithm, retrieved from the Internet on Jul. 7, 2014 at http://en.wikipedia.org/wiki/Expectation-maximization_algorithm.
wikipedia.com, Fuzzy clustering, retrieved from the Internet on Jul. 7, 2014 at http://en.wikipedia.org/wiki/Fuzzy_clustering.
wikipedia.com, k-means clustering, retrieved from the Internet on Jul. 7, 2014 at http://en.wikipedia.org/wiki/K-means_clustering.

(56) References Cited

OTHER PUBLICATIONS

Michael Rubinstein, Feb. 2014, Eulerian Video Magnification for Revealing Subtle Changes in the World, retrieved from the Internet on Jun. 6, 2014 at http://people.csail.mit.edu/mrub/vidmag/.

* cited by examiner

DEVICE HAVING DIGITAL INFRARED SENSOR AND NON-TOUCH OPTICAL DETECTION OF AMPLIFIED TEMPORAL VARIATION OF VITAL SIGNS

RELATED APPLICATIONS

This application claims the benefit and priority under 35 U.S.C. 119 to GB 1411983.8 filed on 4 Jul. 2014.

This application is a continuation of, and claims the benefit and priority under 35 U.S.C. 120 of U.S. application Ser. No. 14/324,235 filed on 6 Jul. 2014.

FIELD

This disclosure relates generally to motion amplification in images.

BACKGROUND

Conventional personal computers implement motion amplification.

BRIEF DESCRIPTION

One aspect includes a non-touch thermometer to measure temperature, the non-touch thermometer including: a microprocessor, a battery operably coupled to the microprocessor, a single button operably coupled to the microprocessor, a camera operably coupled to the microprocessor and providing at least two images to the microprocessor, a digital infrared sensor operably coupled to the microprocessor, the digital infrared sensor having ports that provide only digital readout, and a display device operably coupled to the microprocessor, where the microprocessor is operable to receive from the ports that provide only digital readout a digital signal that is representative of an infrared signal detected by the digital infrared sensor and the microprocessor is operable to determine the temperature from the digital signal that is representative of the infrared signal and the microprocessor including a pixel-examination-module configured to examine pixel values of the at least two images, a temporal-variation module to determine temporal variation of the pixel values between the at least two images being below a particular threshold, a signal processing module configured to amplify the temporal variation resulting in amplified temporal variation, and a visualizer to visualize a pattern of flow of blood in the amplified temporal variation in the at least two images.

One aspect includes a non-touch thermometer to measure temperature, the non-touch thermometer including: a microprocessor, a battery operably coupled to the microprocessor, a single button operably coupled to the microprocessor, a camera operably coupled to the microprocessor and providing at least two images to the microprocessor, a digital infrared sensor operably coupled to the microprocessor, the digital infrared sensor having only digital readout ports, the digital infrared sensor having no analog sensor readout ports, and a display device operably coupled to the microprocessor, where the microprocessor is operable to receive from the digital readout ports a digital signal that is representative of an infrared signal detected by the digital infrared sensor and the microprocessor is operable to determine the temperature from the digital signal that is representative of the infrared signal and the microprocessor including a pixel-examination-module configured to examine pixel values of the at least two images, a temporal-variation module to determine temporal variation of the pixel values between the at least two images being below a particular threshold, a signal processing module configured to amplify the temporal variation resulting in amplified temporal variation, and a visualizer to visualize a pattern of flow of blood in the amplified temporal variation in the at least two images.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into four sections. In the first section, apparatus of digital infrared sensor implementations are described. In the second section, implementations of methods of digital infrared sensors are described. In the third section, implementations of apparatus of vital sign amplification are described. In the fourth section, implementations of methods of vital sign amplification are described. In the fifth section, hardware and operating environments in conjunction with which implementations may be practiced are described. Finally, in the sixth section, a conclusion of the detailed description is provided. The apparatus and methods disclosed in the third and fourth sections are notably beneficial in generating a temporal variation from which a heartrate and the respiratory rate can be generated.

Digital Infrared Sensor Apparatus Implementations

In this section, particular apparatus of implementations are described by reference to a series of diagrams.

Figure 1:
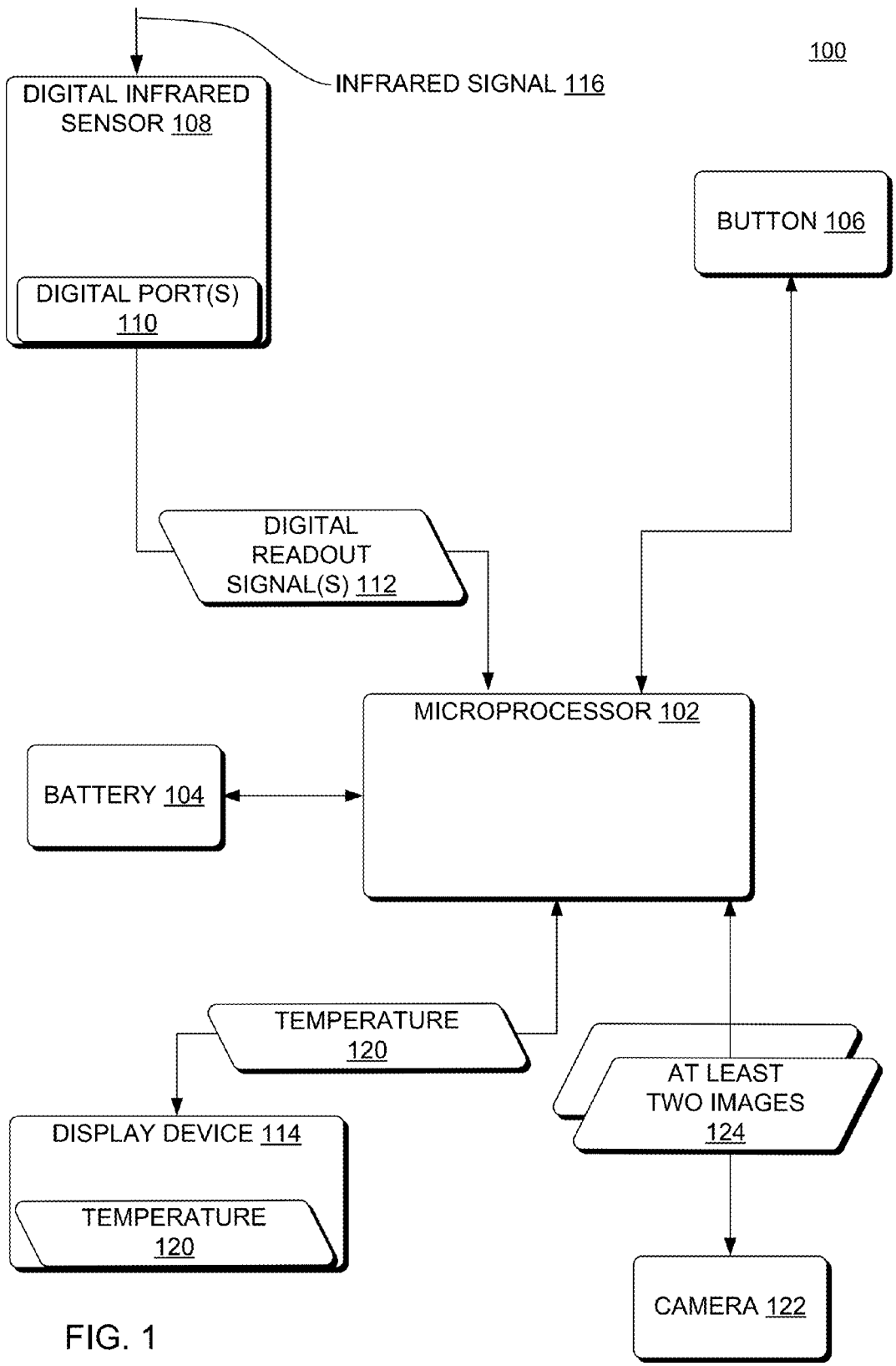
FIG. 1 is a block diagram of a non-touch thermometer that does not include a digital infrared sensor, according to an implementation.

FIG. 1 is a block diagram of a non-touch thermometer 100 that does not include a digital infrared sensor, according to an implementation. Non-touch thermometer 100 is an apparatus to measure temperature. The non-touch thermometer 100 includes a microprocessor 102. The non-touch thermometer 100 includes a battery 104 that is operably coupled to the microprocessor 102. The non-touch thermometer 100 includes a single button 106 that is operably coupled to the microprocessor 102. The non-touch thermometer 100 includes a digital infrared sensor 108 that is operably coupled to the microprocessor 102. The digital infrared sensor 108 includes digital ports 110 that provide only digital readout signal 112. The non-touch thermometer 100 includes a display device 114 that is operably coupled to the microprocessor 102. The microprocessor 102 is operable to receive from the digital ports 110 that provide only digital readout signal 112. The digital readout signal 112 that is representative of an infrared signal 116 detected by the digital infrared sensor 108. The microprocessor 102 is operable to determine the temperature 120 from the digital readout signal 112 that is representative of the infrared signal 116. The non-touch thermometer 100 includes a camera 122 that is operably coupled to the microprocessor 102 and is operable to provide two or more images 124 to the microprocessor 102.

Figure 2:
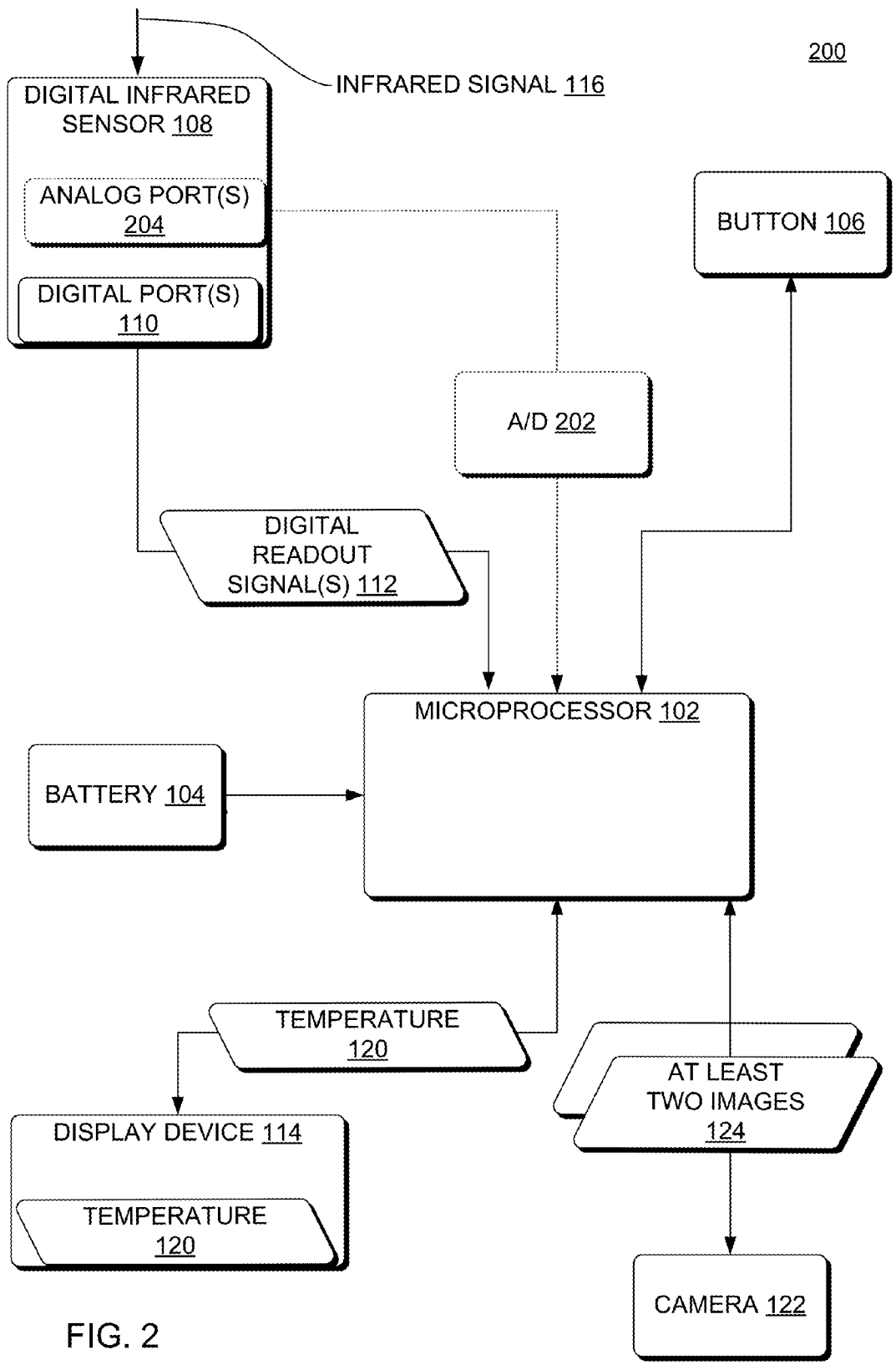
FIG. 2 is a block diagram of a non-touch thermometer that does not include an analog-to-digital converter, according to an implementation.

FIG. 2 is a block diagram of a non-touch thermometer 200 that does not include an analog-to-digital converter, according to an implementation. The non-touch thermometer 200 does not include an analog-to-digital (A/D) converter 202 operably coupled between the digital infrared sensor 108 and the microprocessor 102. The digital infrared sensor 108 also does not include analog readout ports 204. The dashed lines of the analog-to-digital converter 202 and the analog readout ports 204 indicates absence of the A/D converter 202 and the analog readout ports 204 in the non-touch thermometer 200. The non-touch thermometer 200 includes a microprocessor 102. The non-touch thermometer 200 includes a battery 104 that is operably coupled to the microprocessor 102. The non-touch thermometer 200 includes a single button 106 that is operably coupled to the microprocessor 102. The non-touch thermometer 200 includes a digital infrared sensor 108 that is operably coupled to the microprocessor 102 with no analog-to-digital converter that is operably coupled between the digital infrared sensor 108 and the microprocessor 102, the digital infrared sensor 108 having only digital ports 110, the digital infrared sensor 108 having no analog sensor readout ports. The non-touch thermometer 200 includes and a display device 114 that is operably coupled to the microprocessor 102, where the microprocessor 102 is operable to receive from the digital ports 110 a digital readout signal 112 that is representative of an infrared signal 116 detected by the digital infrared sensor 108 and the microprocessor 102 is operable to determine the temperature 120 from the digital readout signal 112 that is representative of the infrared signal 116. The non-touch thermometer 200 also includes a camera 122 that is operably coupled to the microprocessor 102 and is operable to provide two or more images 124 to the microprocessor 102.

In some implementations, the digital IR sensor 108 is a low noise amplifier, 17-bit ADC and powerful DSP unit through which high accuracy and resolution of the thermometer is achieved.

In some implementations, the digital IR sensor 108, 10-bit pulse width modulation (PWM) is configured to continuously transmit the measured temperature in range of −20 . . . 120° C., with an output resolution of 0.14° C. The factory default power on reset (POR) setting is SMBus.

In some implementations, the digital IR sensor 108 is packaged in an industry standard TO-39 package.

In some implementations, the generated object and ambient temperatures are available in RAM of the digital IR sensor 108 with resolution of 0.01° C. The temperatures are accessible by 2 wire serial SMBus compatible protocol (0.02° C. resolution) or via 10-bit PWM (Pulse Width Modulated) output of the digital IR sensor 108.

In some implementations, the digital IR sensor 108 is factory calibrated in wide temperature ranges: −40 . . . 85° C. for the ambient temperature and −70 . . . 380° C. for the object temperature.

In some implementations of the digital IR sensor 108, the measured value is the average temperature of all objects in the Field Of View (FOV) of the sensor. In some implementations, the digital IR sensor 108 has a standard accuracy of ±0.5° C. around room temperatures, and in some implementations, the digital IR sensor 108 has an accuracy of ±0.2° C. in a limited temperature range around the human body temperature.

These accuracies are only guaranteed and achievable when the sensor is in thermal equilibrium and under isothermal conditions (there are no temperature differences across the sensor package). The accuracy of the thermometer can be influenced by temperature differences in the package induced by causes like (among others): Hot electronics behind the sensor, heaters/coolers behind or beside the sensor or by a hot/cold object very close to the sensor that not only heats the sensing element in the thermometer but also the thermometer package. In some implementations of the digital IR sensor 108, the thermal gradients are measured internally and the measured temperature is compensated in consideration of the thermal gradients, but the effect is not totally eliminated. It is therefore important to avoid the causes of thermal gradients as much as possible or to shield the sensor from the thermal gradients.

In some implementations, the digital IR sensor 108 is calibrated for an object emissivity of 1, but in some implementations, the digital IR sensor 108 is calibrated for any emissivity in the range 0.1 . . . 1.0 without the need of recalibration with a black body.

In some implementations of the digital IR sensor 108, the PWM can be easily customized for virtually any range desired by the customer by changing the content of 2 EEPROM cells. Changing the content of 2 EEPROM cells has no effect on the factory calibration of the device. The PWM pin can also be configured to act as a thermal relay (input is To), thus allowing for an easy and cost effective implementation in thermostats or temperature (freezing/boiling) alert applications. The temperature threshold is programmable by the microprocessor 102 of the non-touch thermometer. In a non-touch thermometer having a SMBus system the programming can act as a processor interrupt that can trigger reading all slaves on the bus and to determine the precise condition.

In some implementations, the digital IR sensor 108 has an optical filter (long-wave pass) that cuts off the visible and near infra-red radiant flux is integrated in the package to provide ambient and sunlight immunity. The wavelength pass band of the optical filter is from 5.5 till 14 μm.

In some implementations, the digital IR sensor 108 is controlled by an internal state machine, which controls the measurements and generations of the object and ambient temperatures and does the post-processing of the temperatures to output the temperatures through the PWM output or the SMBus compatible interface.

Some implementations of the non-touch thermometer includes 2 IR sensors, the output of the IR sensors being amplified by a low noise low offset chopper amplifier with programmable gain, converted by a Sigma Delta modulator to a single bit stream and fed to a DSP for further processing. The signal is treated by programmable (by means of EEPROM contend) FIR and IIR low pass filters for further reduction of the bandwidth of the input signal to achieve the desired noise performance and refresh rate. The output of the IIR filter is the measurement result and is available in the internal RAM. 3 different cells are available: One for the on-board temperature sensor and 2 for the IR sensors. Based on results of the above measurements, the corresponding ambient temperature Ta and object temperatures To are generated. Both generated temperatures have a resolution of 0.01° C. The data for Ta and To is read in two ways: Reading RAM cells dedicated for this purpose via the 2-wire interface (0.02° C. resolution, fixed ranges), or through the PWM digital output (10 bit resolution, configurable range). In the last step of the measurement cycle, the measured Ta and To are rescaled to the desired output resolution of the PWM) and the regenerated data is loaded in the registers of the PWM state machine, which creates a constant frequency with a duty cycle representing the measured data.

In some implementations, the digital IR sensor 108 includes a SCL pin for Serial clock input for 2 wire communications protocol, which supports digital input only, used as the clock for SMBus compatible communication. The SCL pin has the auxiliary function for building an external voltage regulator. When the external voltage regulator is used, the 2-wire protocol for a power supply regulator is overdriven.

In some implementations, the digital IR sensor 108 includes a slave deviceA/PWM pin for Digital input/output. In normal mode the measured object temperature is accessed at this pin Pulse Width Modulated. In SMBus compatible mode the pin is automatically configured as open drain NMOS. Digital input/output, used for both the PWM output of the measured object temperature(s) or the digital input/output for the SMBus. In PWM mode the pin can be programmed in EEPROM to operate as Push/Pull or open drain NMOS (open drain NMOS is factory default). In SMBus mode slave deviceA is forced to open drain NMOS I/O, push-pull selection bit defines PWM/Thermal relay operation. The PWM/slave deviceA pin the digital IR sensor 108 operates as PWM output, depending on the EEPROM settings. When WPWM is enabled, after POR the PWM/slave deviceA pin is directly configured as PWM output. When the digital IR sensor 108 is in PWM mode, SMBus communication is restored by a special command. In some implementations, the digital IR sensor 108 is read via PWM or SMBus compatible interface. Selection of PWM output is done in EEPROM configuration (factory default is SMBus). PWM output has two programmable formats, single and dual data transmission, providing single wire reading of two temperatures (dual zone object or object and ambient). The PWM period is derived from the on-chip oscillator and is programmable.

In some implementations, the digital IR sensor 108 includes a VDD pin for External supply voltage and a VSS pin for ground.

The microprocessor 102 has read access to the RAM and EEPROM and write access to 9 EEPROM cells (at addresses 0x00, 0x01, 0x02, 0x03, 0x04, 0x05*, 0x0E, 0x0F, 0x09). When the access to the digital IR sensor 108 is a read operation, the digital IR sensor 108 responds with 16 data bits and 8 bit PEC only if its own slave address, programmed in internal EEPROM, is equal to the SA, sent by the master. A slave feature allows connecting up to 127 devices (SA=0x00 . . . 0x07F) with only 2 wires. In order to provide access to any device or to assign an address to a slave device before slave device is connected to the bus system, the communication starts with zero slave address followed by low R/W bit. When the zero slave address followed by low R/W bit sent from the microprocessor 102, the digital IR sensor 108 responds and ignores the internal chip code information.

In some implementations, two digital IR sensors 108 are not configured with the same slave address on the same bus.

In regards to bus protocol, after every received 8 bits the slave device should issue ACK or NACK. When a microprocessor 102 initiates communication, the microprocessor 102 first sends the address of the slave and only the slave device which recognizes the address will ACK, the rest will remain silent. In case the slave device NACKs one of the bytes, the microprocessor 102 stops the communication and repeat the message. A NACK could be received after the packet error code (PEC). A NACK after the PEC means that there is an error in the received message and the microprocessor 102 will try resending the message. PEC generation includes all bits except the START, REPEATED START, STOP, ACK, and NACK bits. The PEC is a CRC-8 with polynomial X8+X2+X1+1. The Most Significant Bit of every byte is transferred first.

In single PWM output mode the settings for PWM1 data only are used. The temperature reading can be generated from the signal timing as:

$$T_{OUT} = \left(\frac{2t_2}{T} \times (T_{O\_MAX} - T_{O\_MIN})\right) + T_{O\_MIN}$$

where Tmin and Tmax are the corresponding rescale coefficients in EEPROM for the selected temperature output (Ta, object temperature range is valid for both Tobj1 and Tobj2 as specified in the previous table) and T is the PWM period. Tout is TO1, TO2 or Ta according to Config Register [5:4] settings.

The different time intervals t1 . . . t4 have following meaning:

t1: Start buffer. During t1 the signal is always high. t1=0.125 s×T (where T is the PWM period)

t2: Valid Data Output Band, 0 . . . ½T. PWM output data resolution is 10 bit.

t3: Error band—information for fatal error in EEPROM (double error detected, not correctable).

t3=0.25 s×T. Therefore a PWM pulse train with a duty cycle of 0.875 will indicate a fatal error in EEPROM (for single PWM format). FE means Fatal Error.

In regards to a format for extended PWM, the temperature transmitted in Data 1 field can be generated using the following equation:

$$T_{OUT1} = \left(\frac{4t_2}{T} \times (T_{MAX1} - T_{MIN1})\right) + T_{MIN1}$$

For Data 2 field the equation is:

$$T_{OUT2} = \left(\frac{4t_5}{T} \times (T_{MAX2} - T_{MIN2})\right) + T_{MIN2}$$

Figure 3:
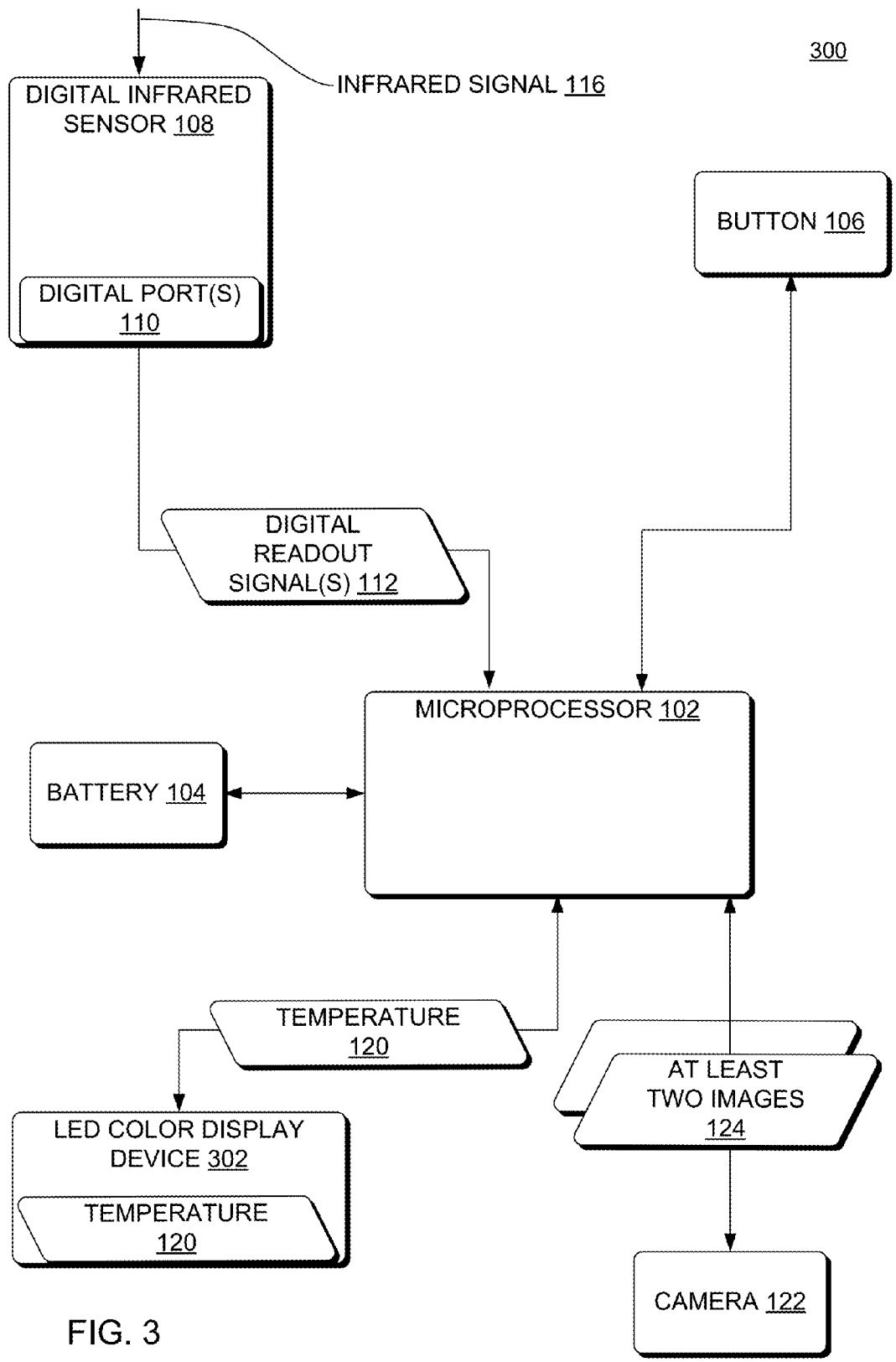
FIG. 3 is a block diagram of a non-touch thermometer having a color display device, according to an implementation.

FIG. 3 is a block diagram of a non-touch thermometer 300 having a color display device, according to an implementation. In FIG. 3, the display device 114 of FIG. 1 is a LED color display device.

In regards to the structural relationship of the digital infrared sensor 108 and the microprocessor 102 in FIG. 1-3, heat radiation on the digital infrared sensor 108 from any source such as the microprocessor 102 or heat sink, will distort detection of infrared energy by the digital infrared sensor 108. In order to prevent or at least reduce heat transfer between the digital infrared sensor 108 and the microprocessor 102, the non-touch thermometers 100, 200 and 300 are low-powered devices and thus low heat-generating devices that are also powered by a battery 104; and that are only used for approximately a 5 second period of time for each measurement (1 second to acquire the temperature samples and generate the body core temperature result, and 4 seconds to display that result to the operator) so there is little heat generated by the non-touch thermometers 100, 200 and 300 in active use.

The internal layout of the non-touch thermometers 100, 200 and 300 minimizes as practically as possible the digital infrared sensor as far away in distance from all other components such the microprocessor 102 within the practical limitations of the industrial design of the non-touch thermometers 100, 200 and 300.

Figure 23:
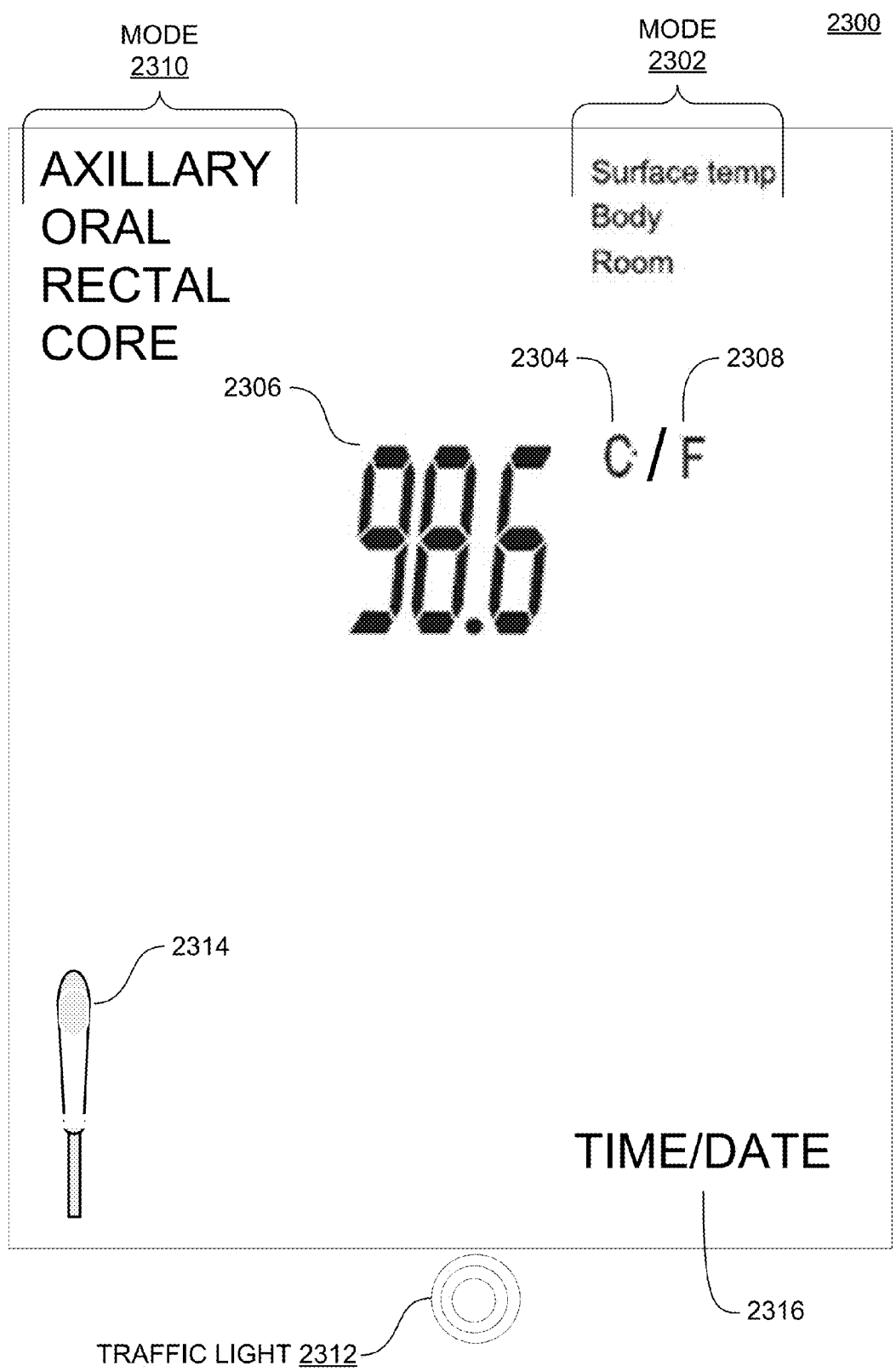
FIG. 23 is a representation of display that is presented on the display device of apparatus in FIGS. 1-3 and 24-28, according to an implementation.

More specifically, to prevent or at least reduce heat transfer between the digital infrared sensor 108 and the microprocessor 102, the digital infrared sensor 108 is isolated on a separate PCB from the PCB that has the microprocessor 102, as shown in FIG. 23, and the two PCBs are connected by only a connector that has 4 pins. The minimal connection of the single connector having 4 pins reduces heat transfer from the microprocessor 102 to the digital infrared sensor 108 through the electrical connector and through transfer that would occur through the PCB material if the digital infrared sensor 108 and the microprocessor 102 were mounted on the same PCB.

Digital Infrared Sensor Method Implementations

In the previous section, apparatus of the operation of an implementation was described. In this section, the particular methods performed by non-touch thermometer 100, 200 and 300 of such an implementation are described by reference to a series of flowcharts.

Figure 4:
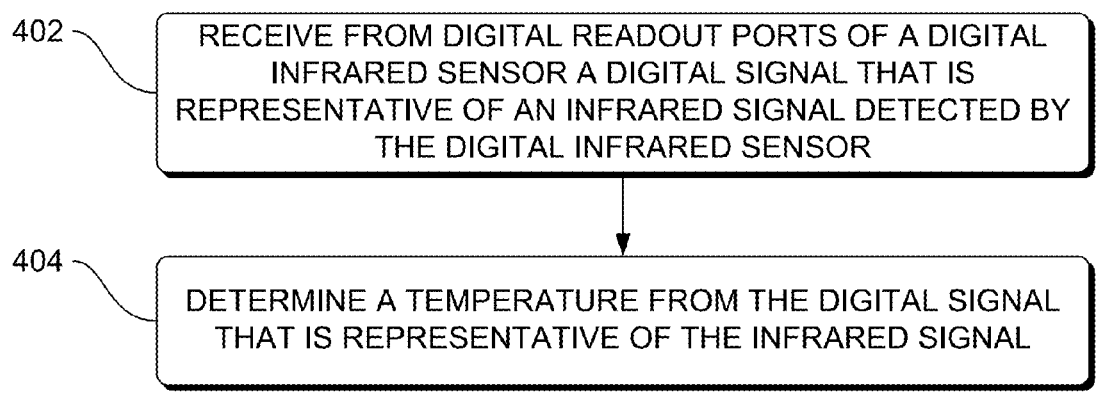
FIG. 4 is a flowchart of a method to determine a temperature from a digital infrared sensor, according to an implementation.

FIG. 4 is a flowchart of a method 400 to determine a temperature from a digital infrared sensor, according to an implementation. Method 400 includes receiving from the digital readout ports of a digital infrared sensor a digital signal that is representative of an infrared signal detected by the digital infrared sensor, at block 402.

Method 400 also includes determining a temperature from the digital signal that is representative of the infrared signal, at block 404.

Figure 5:
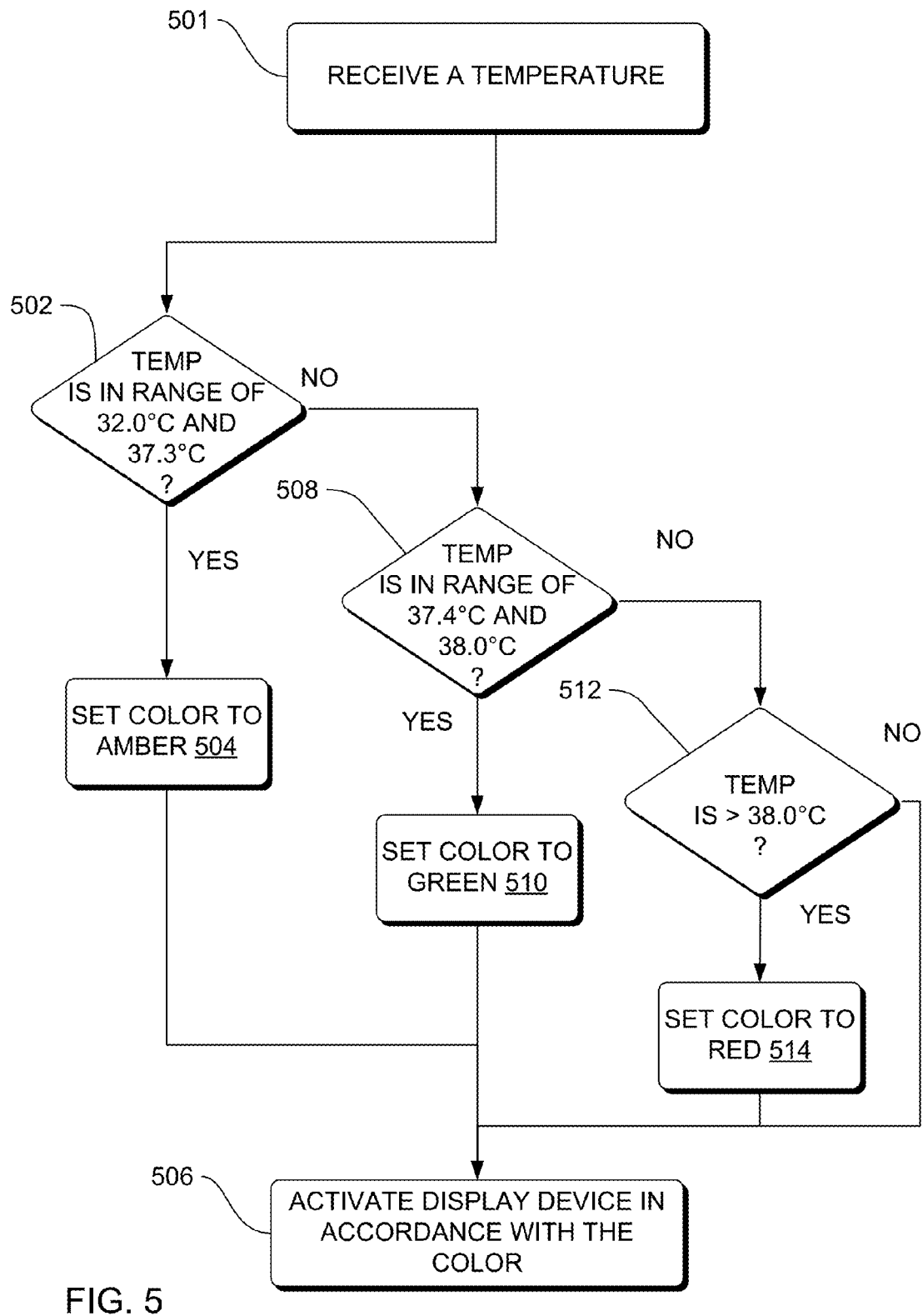
FIG. 5 is a flowchart of a method to display temperature color indicators, according to an implementation of three colors.

FIG. 5 is a flowchart of a method 500 to display temperature color indicators, according to an implementation of three colors. Method 500 provides color rendering in the color LED 2312 to indicate a general range of a temperature.

Method 500 includes receiving a temperature (such as temperature 120 in FIG. 1), at block 501.

Method 500 also includes determining whether or not the temperature is in the range of 32.0° C. and 37.3° C., at block 502. If the temperature is in the range of 32.0° C. and 37.3° C., then the color is set to 'amber' to indicate a temperature that is low, at block 504 and the background of the color LED 2312 is activated in accordance with the color, at block 506.

If the temperature is not the range of 32.0° C. and 37.3° C., then method 500 also includes determining whether or not the temperature is in the range of 37.4° C. and 38.0° C., at block 508. If the sensed temperature is in the range of 37.4° C. and 38.0° C., then the color is set to green to indicate no medical concern, at block 510 and the background of the color LED 2312 is activated in accordance with the color, at block 506.

If the temperature is not the range of 37.4° C. and 38.0° C., then method 500 also includes determining whether or not the temperature is over 38.0° C., at block 512. If the temperature is over 38.0° C., then the color is set to 'red' to indicate alert, at block 512 and the background of the color LED 2312 is activated in accordance with the color, at block 506.

Method 500 assumes that temperature is in gradients of 10ths of a degree. Other temperature range boundaries are used in accordance with other gradients of temperature sensing.

In some implementations, some pixels in the color LED 2312 are activated as an amber color when the temperature is between 36.3° C. and 37.3° C. (97.3° F. to 99.1° F.), some pixels in the color LED 2312 are activated as a green when the temperature is between 37.4° C. and 37.9° C. (99.3° F. to 100.2° F.), some pixels in the color LED 2312 are activated as a red color when the temperature is greater than 38° C. (100.4° F.). In some implementations, the color LED 2312 is a backlit LCD screen 302 in FIG. 3 (which is easy to read in a dark room) and some pixels in the color LED 2312 are activated (remain lit) for about 5 seconds after the single button 106 is released. After the color LED 2312 has shut off, another temperature reading can be taken by the apparatus. The color change of the color LED 2312 is to alert the operator of the apparatus of a potential change of body temperature of the human or animal subject. The temperature reported on the display can be used for treatment decisions.

Figure 6:
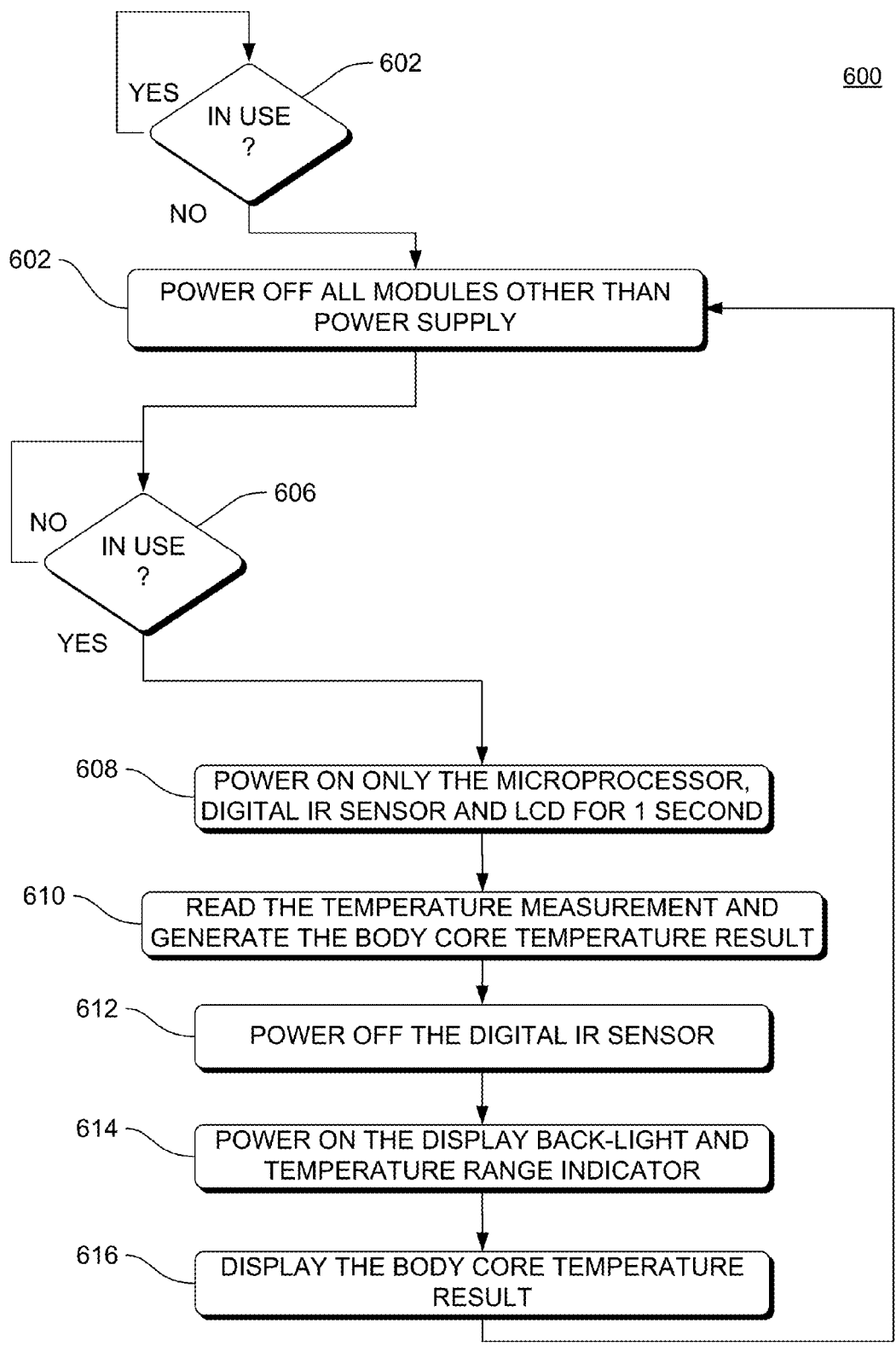
FIG. 6 is a flowchart of a method to manage power in a non-touch thermometer having a digital infrared sensor, according to an implementation.

FIG. 6 is a flowchart of a method 600 to manage power in a non-touch device having a digital infrared sensor, according to an implementation. The method 600 manages power in the device, such as non-touch thermometer in FIG. 1-3, the non-touch thermometer 2400 in FIG. 24, the hand-held device 2100 in FIG. 21 and/or the computer 2200 in FIG. 22 in order to reduce heat pollution in the digital infrared sensor.

Figure 21:
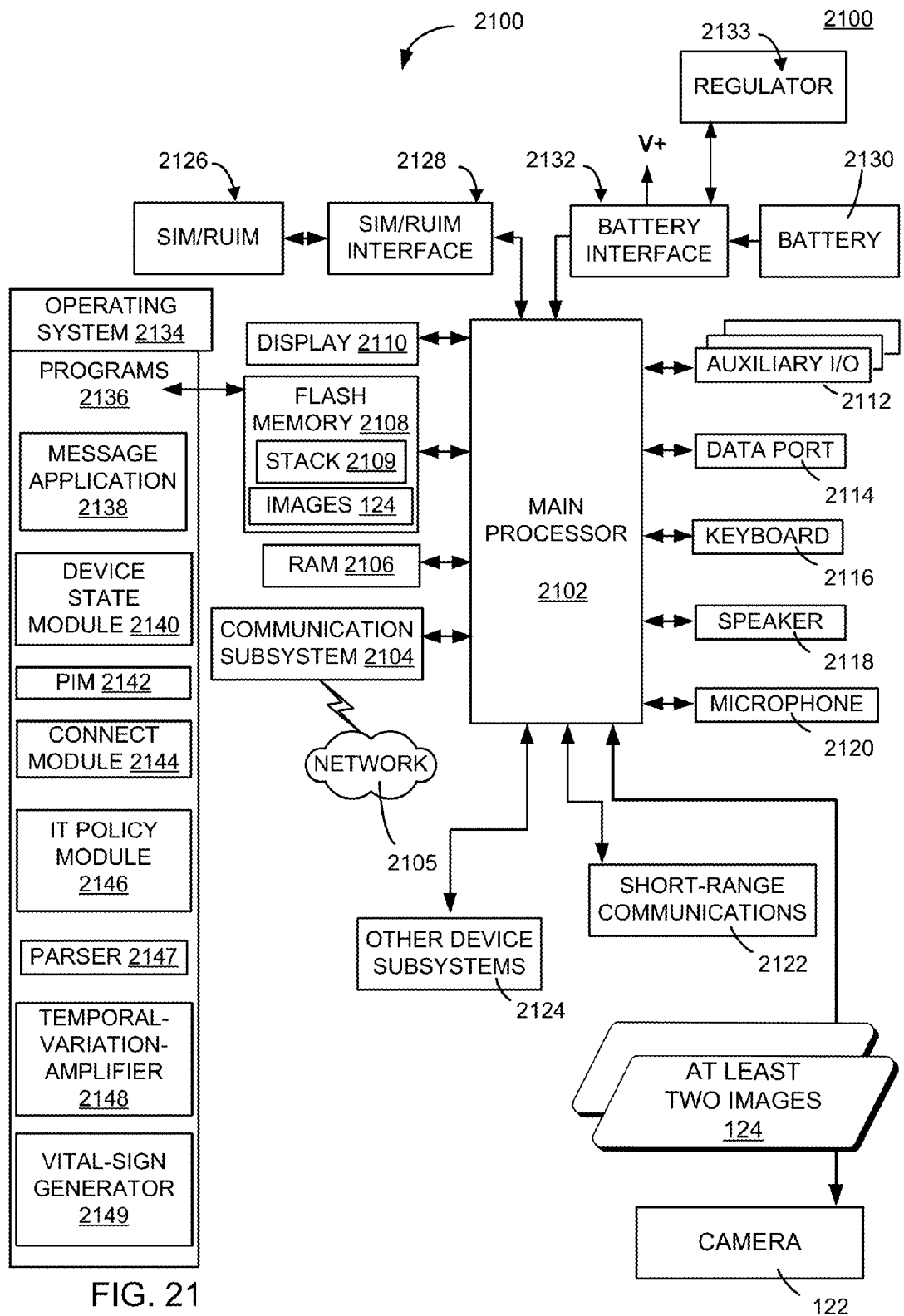
FIG. 21 is a block diagram of a hand-held device, according to an implementation.
Figure 22:
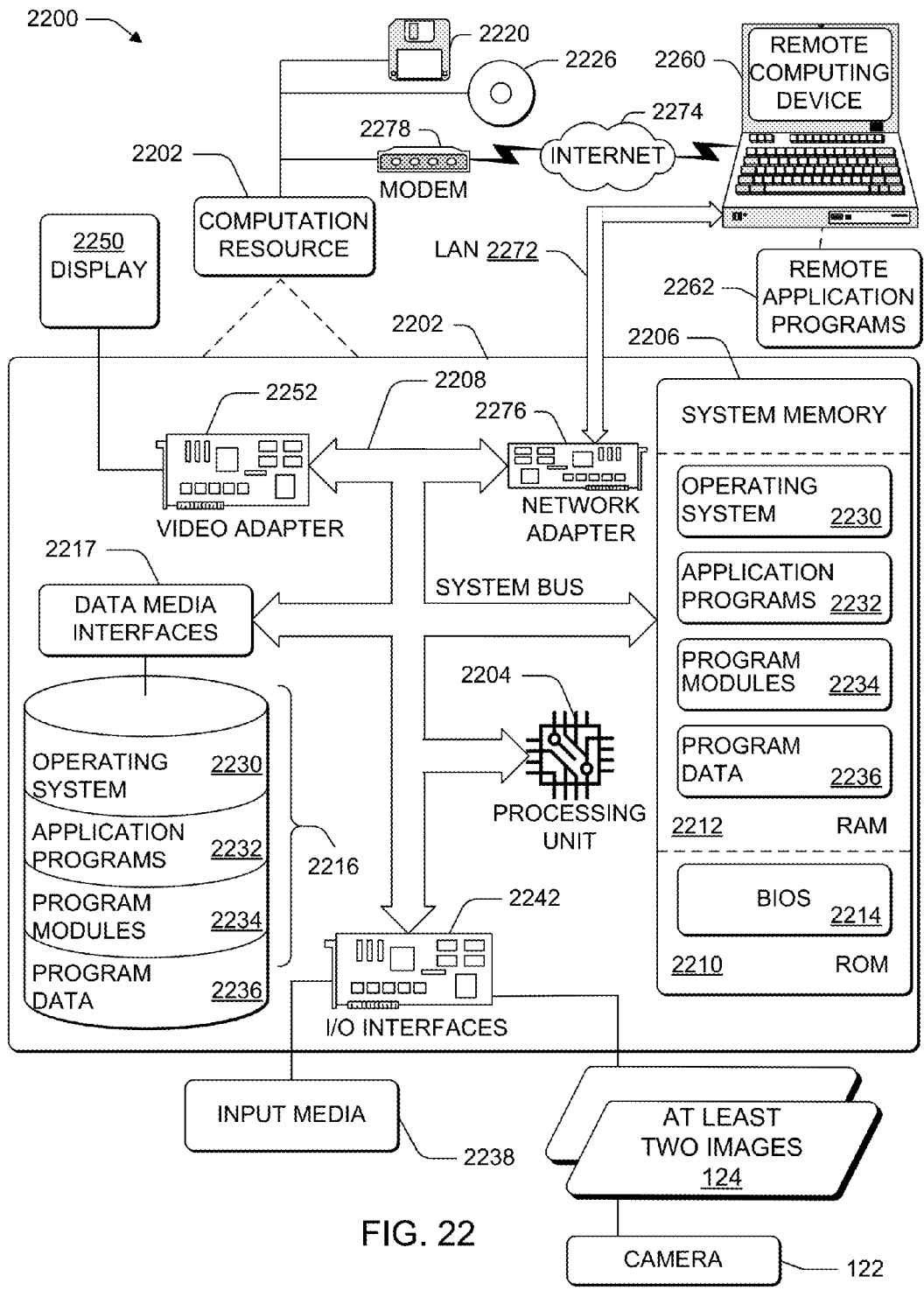
FIG. 22 illustrates an example of a computer environment, according to an implementation.
Figure 24:
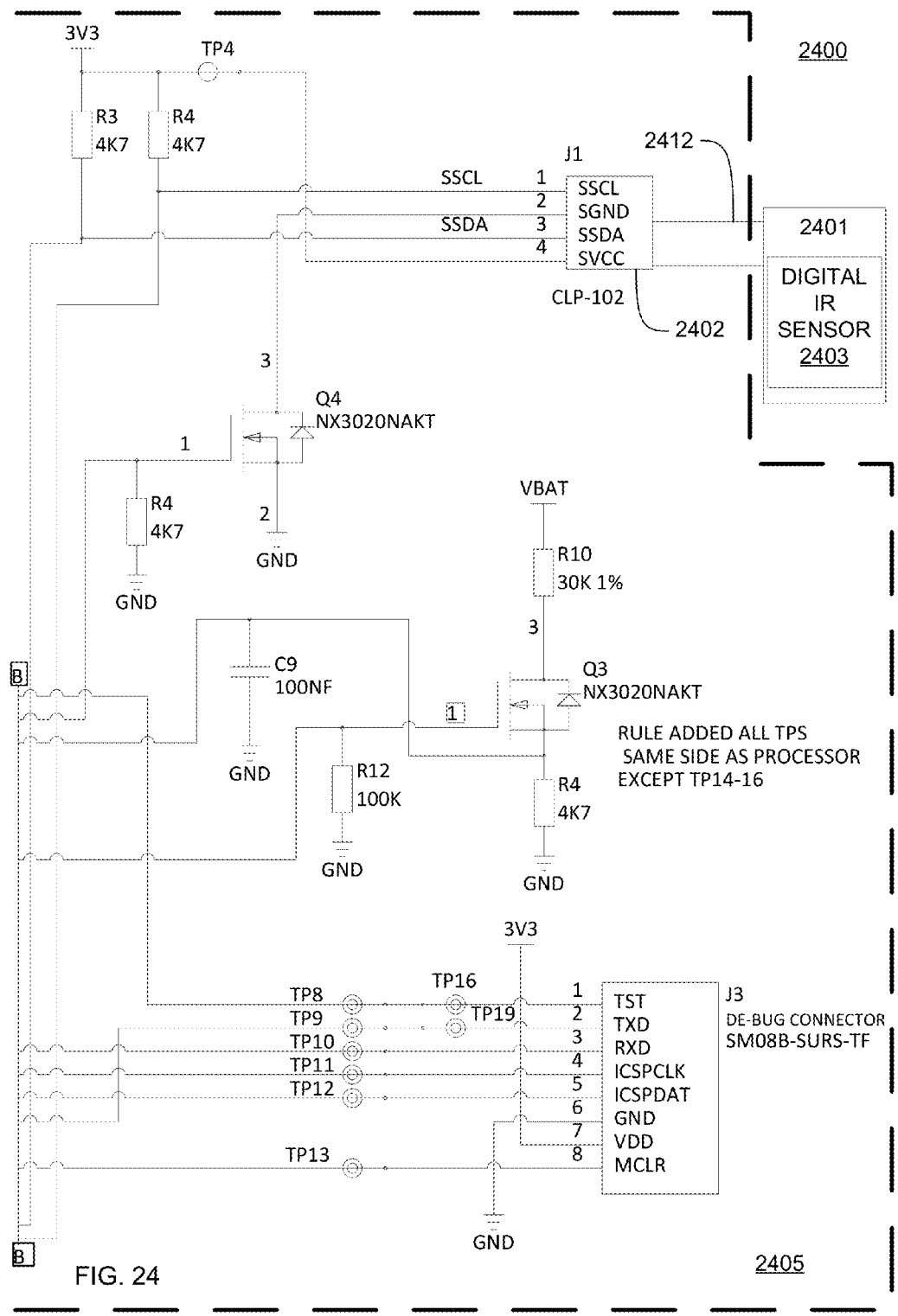
FIG. 24 is a portion of a schematic of a circuit board of a non-touch thermometer, according to an implementation.

To prevent or at least reduce heat transfer between the digital infrared sensor 108 and the microprocessor 102, microprocessor 2404 In FIG. 24, main processor 2102 in FIG. 21 or processing unit 2204 in FIG. 22, the components of the non-touch thermometers 100, 200 and 300 in FIG. 1-3, the non-touch thermometer 2400 in FIG. 24, the hand-held device 2100 in FIG. 21 and/or the computer 2200 in FIG. 22 are power controlled, i.e. the non-touch thermometers 100, 200 and 300 in FIG. 1-3, the non-touch thermometer 2400 in FIG. 24, the hand-held device 2100 in FIG. 21 and/or the computer 2200 in FIG. 22 turn subsystems on and off, and the components are only activated when needed in the measurement and display process, which reduces power consumption and thus heat generation by the microprocessor 102, microprocessor 2404 In FIG. 24, main processor 2102 in FIG. 21 or processing unit 2204 in FIG. 22, of the non-touch thermometers 100, 200 and 300 in FIG. 1-3, the non-touch thermometer 2400 in FIG. 24, the hand-held device 2100 in FIG. 21 and/or the computer 2200 in FIG. 22, respectively. When not in use, at block 602, the non-touch thermometers 100, 200 and 300 in FIG. 1-3, the non-touch thermometer 2400 in FIG. 24, the hand-held device 2100 in FIG. 21 and/or the computer 2200 in FIG. 22 are completely powered-off, at block 604 (including the main PCB having the microprocessor 102, microprocessor 2404 In FIG. 24, main processor 2102 in FIG. 21 or processing unit 2204 in FIG. 22, and the sensor PCB having the digital infrared sensor 108) and not drawing any power, other than a power supply, i.e. a boost regulator, which has the effect that the non-touch thermometers 100, 200 and 300 in FIG. 1-3, the non-touch thermometer 2400 in FIG. 24, the hand-held device 2100 in FIG. 21 and/or the computer 2200 in FIG. 22 draw only drawing micro-amps from the battery 104 while in the off state, which is required for the life time requirement of 3 years of operation, but which also means that in the non-use state there is very little powered circuitry in the non-touch thermometers 100, 200 and 300 in FIG. 1-3, the non-touch thermometer 2400 in FIG. 24, the hand-held device 2100 in FIG. 21 and/or the computer 2200 in FIG. 22 and therefore very little heat generated in the non-touch thermometers 100, 200 and 300 in FIG. 1-3, the non-touch thermometer 2400 in FIG. 24, the hand-held device 2100 in FIG. 21 and/or the computer 2200 in FIG. 22.

When the non-touch thermometers 100, 200 and 300 in FIG. 1-3, the non-touch thermometer 2400 in FIG. 24, the hand-held device 2100 in FIG. 21 and/or the computer 2200 in FIG. 22 are started by the operator, at block 606, only the microprocessor 102, microprocessor 2404 In FIG. 24, main processor 2102 in FIG. 21 or processing unit 2204 in FIG. 22, digital infrared sensor 108, and low power LCD (e.g. display device 114) are turned on for the first 1 second, at block 608, to take the temperature measurement via the digital infrared sensor 108 and generate the body core temperature result via the microprocessor 102 in FIG. 1-3, microprocessor 2404 in FIG. 24, main processor 2102 in FIG. 21 or processing unit 2204 in FIG. 22, at block 610. In this way, the main heat generating components (the LCD 114, the main PCB having the microprocessor 102 and the sensor PCB having the digital infrared sensor 108), the display back-light and the temperature range indicator (i.e. the traffic light indicator 2312) are not on and therefore not generating heat during the critical start-up and measurement process, no more than 1 second. After the measurement process of block 610 has been completed, the digital infrared sensor 108 is turned off, at block 612, to reduce current usage from the batteries and heat generation, and also the display back-light and temperature range indicators are turned on, at block 614.

The measurement result is displayed for 4 seconds, at block 616, and then the non-touch thermometers 100, 200 and 300 in FIG. 1-3, the non-touch thermometer 2400 in FIG. 24, the hand-held device 2100 in FIG. 21 and/or the computer 2200 in FIG. 22 are put in low power-off state, at block 618.

In some implementations of methods and apparatus of FIG. 1-6 an operator can take the temperature of a subject at multiple locations on a patient and from the temperatures at multiple locations to determine the temperature at a number of other locations of the subject. The multiple source points of which the electromagnetic energy is sensed are mutually exclusive to the location of the correlated temperature. In one example, the carotid artery source point on the subject and a forehead source point are mutually exclusive to the core temperature of the subject, an axillary temperature of the subject, a rectal temperature of the subject and an oral temperature of the subject.

The correlation of action can include a calculation based on Formula 1:

$$T_{body} = |f_{stb}(T_{surface\ temp} + f_{ntc}(T_{ntc})) + F4_{body}| \quad \text{Formula 1}$$

where $T_{body}$ is the temperature of a body or subject
where $f_{stb}$ is a mathematical formula of a surface of a body
where $f_{ntc}$ is mathematical formula for ambient temperature reading
where $T_{surface\ temp}$ is a surface temperature determined from the sensing.
where $T_{ntc}$ is an ambient air temperature reading
where $F4_{body}$ is a calibration difference in axillary mode, which is stored or set in a memory of the apparatus either during manufacturing or in the field. The apparatus also sets, stores and retrieves $F4_{oral}$, $F4_{core}$, and $F4_{rectal}$ in the memory.

$f_{ntc}(T_{ntc})$ is a bias in consideration of the temperature sensing mode. For example $f_{axillary}(T_{axillary})=0.2°$ C., $f_{oral}(T_{oral})=0.4°$ C., $f_{rectal}(T_{rectal})=0.5°$ C. and $f_{core}(T_{core})=0.3°$ C.

In some implementations of determining a correlated body temperature of carotid artery by biasing a sensed temperature of a carotid artery, the sensed temperature is biased by +0.5° C. to yield the correlated body temperature. In another example, the sensed temperature is biased by −0.5° C. to yield the correlated body temperature. An example of correlating body temperature of a carotid artery follows:

$f_{ntc}(T_{ntc})=0.2°$ C. when $T_{ntc}=26.2°$ C. as retrieved from a data table for body sensing mode.

assumption: $T_{surface\ temp}=37.8°$ C.

$T_{surface\ temp}+f_{ntc}(T_{ntc})=37.8°$ C.+0.2° C.=38.0° C.

$f_{stb}(T_{surface\ temp}+f_{ntc}(T_{ntc}))=38°$ C.+1.4° C.=39.4° C.

assumption: $F4_{body}=0.5°$ C.

$T_{body}=$ $|f_{stb}(T_{surface\ temp}+f_{ntc}(T_{ntc}))+F4_{body}|=|39.4°$ C.+0.5 C|=39.9° C.

The correlated temperature for the carotid artery is 40.0° C.

In an example of correlating temperature of a plurality of external locations, such as a forehead and a carotid artery to an axillary temperature, first a forehead temperature is calculated using formula 1 as follows:

$f_{ntc}(T_{ntc})=0.2°$ C. when $T_{ntc}=26.2°$ C. as retrieved from a data table for axillary sensing mode.

assumption: $T_{surface\ temp}=37.8°$ C.

$T_{surface\ temp}+f_{ntc}(T_{ntc})=37.8°$ C.+0.2° C.=38.0° C.

$f_{stb}(T_{surface\ temp}+f_{ntc}(T_{ntc}))=38°$ C.+1.4° C.=39.4° C.

assumption: $F4_{body}=0°$ C.

$T_{body}=|f_{stb}(T_{surface\ temp}+f_{ntc}(T_{ntc}))+F4_{body}|=|39.4°$ C.+0 C|=39.4° C.

And second, a carotid temperature is calculated using formula 1 as follows:

$f_{ntc}(T_{ntc})=0.6°$ C. when $T_{ntc}=26.4°$ C. as retrieved from a data table.

assumption: $T_{surface\ temp}=38.0°$ C.

$T_{surface\ temp}+f_{ntc}(T_{ntc})=38.0°$ C.+0.6° C.=38.6° C.

$f_{stb}(T_{surface\ temp}+f_{ntc}(T_{ntc}))=38.6°$ C.+1.4 C=40.0° C.

assumption: $F4_{body}=0°$ C.

$T_{body}=|f_{stb}(T_{surface\ temp}+f_{ntc}(T_{ntc}))+F4_{body}|=|40.0°$ C.+0 C|=40.0° C.

Thereafter the correlated temperature for the forehead (39.4° C.) and the correlated temperature for the carotid artery (40.0° C.) are averaged, yielding the final result of the scan of the forehead and the carotid artery as 39.7° C.

Vital Sign Motion Amplification Apparatus Implementations

Apparatus in FIG. 7-15 use spatial and temporal signal processing to generate vital signs from a series of digital images.

Figure 7:
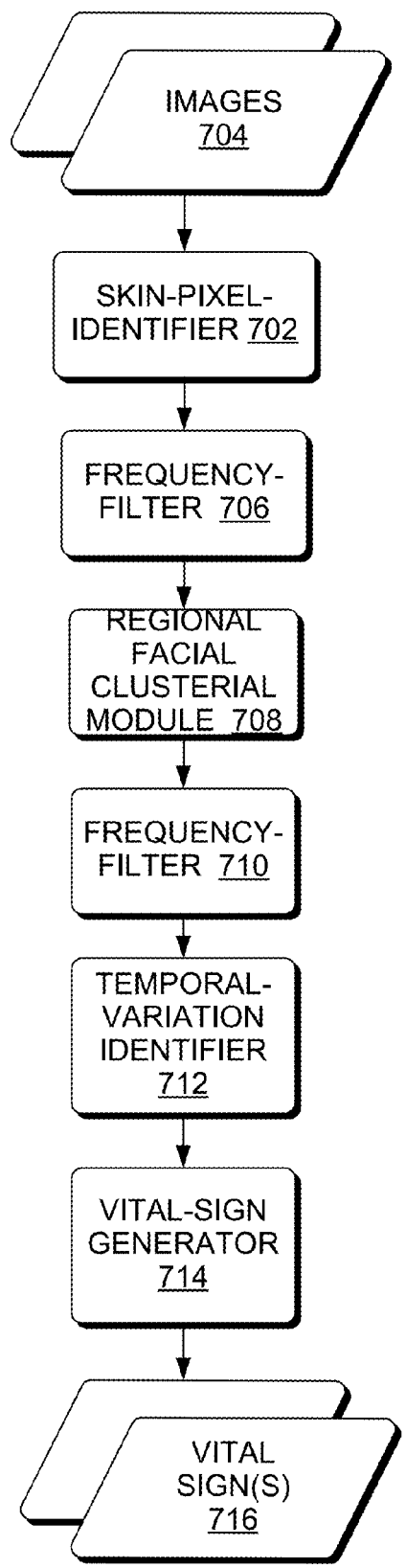
FIG. 7 is a block diagram of an apparatus of motion amplification, according to an implementation.

FIG. 7 is a block diagram of an apparatus 700 of motion amplification, according to an implementation. Apparatus 700 analyzes the temporal and spatial variations in digital images of an animal subject in order to generate and communicate biological vital signs.

In some implementations, apparatus 700 includes a skin-pixel-identifier 702 that identifies pixel values that are representative of the skin in two or more images 704. In some implementations the images 704 are frames of a video. The skin-pixel-identifier 702 performs block 1602 in FIG. 16. Some implementations of the skin-pixel-identifier 702 perform an automatic seed point based clustering process on the two or more images 704. In some implementations, apparatus 700 includes a frequency filter 706 that receives the output of the skin-pixel-identifier 702 and applies a frequency filter to the output of the skin-pixel-identifier 702. The frequency filter 706 performs block 1604 in FIG. 16 to process the images 704 in the frequency domain. In implementations where the apparatus in FIG. 7-15 or the methods in FIG. 16-20 are implemented on non-touch thermometers 100, 200 or 300 in FIG. 1-3, the images 704 in FIG. 7-15 are the images 124 in FIG. 1-3. In some implementations the apparatus in FIG. 7-15 or the methods in FIG. 16-20 are implemented on the hand-held device 2100 in FIG. 21.

In some implementations, apparatus 700 includes a regional facial clusterial module 708 that applies spatial clustering to the output of the frequency filter 706. The regional facial clusterial module 708 performs block 1606 in FIG. 16. In some implementations the regional facial clusterial module 708 includes fuzzy clustering, k-means clustering, expectation-maximization process, Ward's apparatus or seed point based clustering.

In some implementations, apparatus 700 includes a frequency-filter 710 that applies a frequency filter to the output of the regional facial clusterial module 708. The frequency-filter 710 performs block 1608 in FIG. 16. In some implementations, the frequency-filter 710 is a one-dimensional spatial Fourier Transform, a high pass filter, a low pass filter, a bandpass filter or a weighted bandpass filter. Some implementations of frequency-filter 710 includes de-noising (e.g. smoothing of the data with a Gaussian filter). The skin-pixel-identifier 702, the frequency filter 706, the regional facial clusterial module 708 and the frequency-filter 710 amplify temporal variations (as a temporal-variation-amplifier) in the two or more images 704.

In some implementations, apparatus 700 includes a temporal-variation identifier 712 that identifies temporal variation of the output of the frequency-filter 710. Thus, the temporal variation represents temporal variation of the images 704. The temporal-variation identifier 712 performs block 1610 in FIG. 16.

In some implementations, apparatus 700 includes a vital-sign generator 714 that generates one or more vital sign(s) 716 from the temporal variation. The vital sign(s) 716 are displayed for review by a healthcare worker or stored in a volatile or nonvolatile memory for later analysis, or transmitted to other devices for analysis.

Fuzzy clustering is a class of processes for cluster analysis in which the allocation of data points to clusters is not "hard" (all-or-nothing) but "fuzzy" in the same sense as fuzzy logic. Fuzzy logic being a form of many-valued logic which with reasoning that is approximate rather than fixed and exact. In fuzzy clustering, every point has a degree of belonging to clusters, as in fuzzy logic, rather than belonging completely to just one cluster. Thus, points on the edge of a cluster, may be in the cluster to a lesser degree than points in the center of cluster. An overview and comparison of different fuzzy clustering processes is available. Any point x has a set of coefficients giving the degree of being in the kth cluster $w_k(x)$. With fuzzy c-means, the centroid of a cluster is the mean of all points, weighted by a degree of belonging of each point to the cluster:

$$c_k = \frac{\sum_x w_k(x)^m x}{\sum_x w_k(x)^m}.$$

The degree of belonging, $w_k(x)$, is related inversely to the distance from x to the cluster center as calculated on the previous pass. The degree of belonging, $w_k(x)$ also depends on a parameter m that controls how much weight is given to the closest center.

k-means clustering is a process of vector quantization, originally from signal processing, that is popular for cluster analysis in data mining. k-means clustering partitions n observations into k clusters in which each observation belongs to the cluster with the nearest mean, serving as a prototype of the cluster. This results in a partitioning of the data space into Voronoi cells. A Voronoi Cell being a region within a Voronoi Diagram that is a set of points which is specified beforehand. A Voronoi Diagram being a way of dividing space into a number of regions. k-means clustering uses cluster centers to model the data and tends to find clusters of comparable spatial extent, like K-means clustering, but each data point has a fuzzy degree of belonging to each separate cluster.

An expectation-maximization process is an iterative process for finding maximum likelihood or maximum a posteriori (MAP) estimates of parameters in statistical models, where the model depends on unobserved latent variables. The expectation-maximization iteration alternates between performing an expectation step, which creates a function for the expectation of the log-likelihood evaluated using the current estimate for the parameters, and a maximization step, which computes parameters maximizing the expected log-likelihood found on the expectation step. These parameter-estimates are then used to determine the distribution of the latent variables in the next expectation step.

The expectation maximization process seeks to find the maximization likelihood expectation of the marginal likelihood by iteratively applying the following two steps:

1. Expectation step (E step): Calculate the expected value of the log likelihood function, with respect to the conditional distribution of Z given X under the current estimate of the parameters $\theta^{(t)}$:

$$Q(\theta|\theta^{(t)}) = E_{Z|X,\theta^{(t)}}[\log L(\theta;X,Z)]$$

2. Maximization step (M step): Find the parameter that maximizes this quantity:

$$\theta^{(t+1)} = \underset{\theta}{\operatorname{argmax}} Q(\theta|\theta^{(t)})$$

Note that in typical models to which expectation maximization is applied:

1. The observed data points X may be discrete (taking values in a finite or countably infinite set) or continuous (taking values in an uncountably infinite set). There may in fact be a vector of observations associated with each data point.

2. The missing values (aka latent variables) Z are discrete, drawn from a fixed number of values, and there is one latent variable per observed data point.

3. The parameters are continuous, and are of two kinds: Parameters that are associated with all data points, and parameters associated with a particular value of a latent variable (i.e. associated with all data points whose corresponding latent variable has a particular value).

The Fourier Transform is an important image processing tool which is used to decompose an image into its sine and cosine components. The output of the transformation represents the image in the Fourier or frequency domain, while the input image is the spatial domain equivalent. In the Fourier domain image, each point represents a particular frequency contained in the spatial domain image.

The Discrete Fourier Transform is the sampled Fourier Transform and therefore does not contain all frequencies forming an image, but only a set of samples which is large enough to fully describe the spatial domain image. The number of frequencies corresponds to the number of pixels in the spatial domain image, i.e. the image in the spatial and Fourier domain are of the same size.

For a square image of size N×N, the two-dimensional DFT is given by:

$$F(k,l) = \sum_{i=0}^{N-1} \sum_{j=0}^{N-1} f(i,j) e^{-i2\pi \left(\frac{ki}{N} + \frac{lj}{N}\right)}$$

where f(a,b) is the image in the spatial domain and the exponential term is the basis function corresponding to each point F(k,l) in the Fourier space. The equation can be interpreted as: the value of each point F(k,l) is obtained by multiplying the spatial image with the corresponding base function and summing the result.

The basis functions are sine and cosine waves with increasing frequencies, i.e. F(0,0) represents the DC-component of the image which corresponds to the average brightness and F(N−1,N−1) represents the highest frequency.

A high-pass filter (HPF) is an electronic filter that passes high-frequency signals but attenuates (reduces the amplitude of) signals with frequencies lower than the cutoff frequency. The actual amount of attenuation for each frequency varies from filter to filter. A high-pass filter is usually modeled as a linear time-invariant system. A high-pass filter can also be used in conjunction with a low-pass filter to make a band-pass filter. The simple first-order electronic high-pass filter is implemented by placing an input voltage across the series combination of a capacitor and a resistor and using the voltage across the resistor as an output. The product of the resistance and capacitance (R×C) is the time constant ($\tau$); the product is inversely proportional to the cutoff frequency $f_c$, that is:

$$f_c = \frac{1}{2\pi\tau} = \frac{1}{2\pi RC},$$

where $f_c$ is in hertz, $\tau$ is in seconds, R is in ohms, and C is in farads.

A low-pass filter is a filter that passes low-frequency signals and attenuates (reduces the amplitude of) signals with frequencies higher than the cutoff frequency. The actual amount of attenuation for each frequency varies depending on specific filter design. Low-pass filters are also known as high-cut filter, or treble cut filter in audio applications. A low-pass filter is the opposite of a high-pass filter. Low-pass filters provide a smoother form of a signal, removing the short-term fluctuations, and leaving the longer-term trend. One simple low-pass filter circuit consists of a resistor in series with a load, and a capacitor in parallel with the load. The capacitor exhibits reactance, and blocks low-frequency signals, forcing the low-frequency signals through the load instead. At higher frequencies the reactance drops, and the capacitor effectively functions as a short circuit. The combination of resistance and capacitance gives the time constant of the filter. The break frequency, also called the turnover frequency or cutoff frequency (in hertz), is determined by the time constant.

A band-pass filter is a device that passes frequencies within a certain range and attenuates frequencies outside that range. These filters can also be created by combining a low-pass filter with a high-pass filter. Bandpass is an adjective that describes a type of filter or filtering process; bandpass is distinguished from passband, which refers to the actual portion of affected spectrum. Hence, a dual bandpass filter has two passbands. A bandpass signal is a signal containing a band of frequencies not adjacent to zero frequency, such as a signal that comes out of a bandpass filter.

Figure 8:
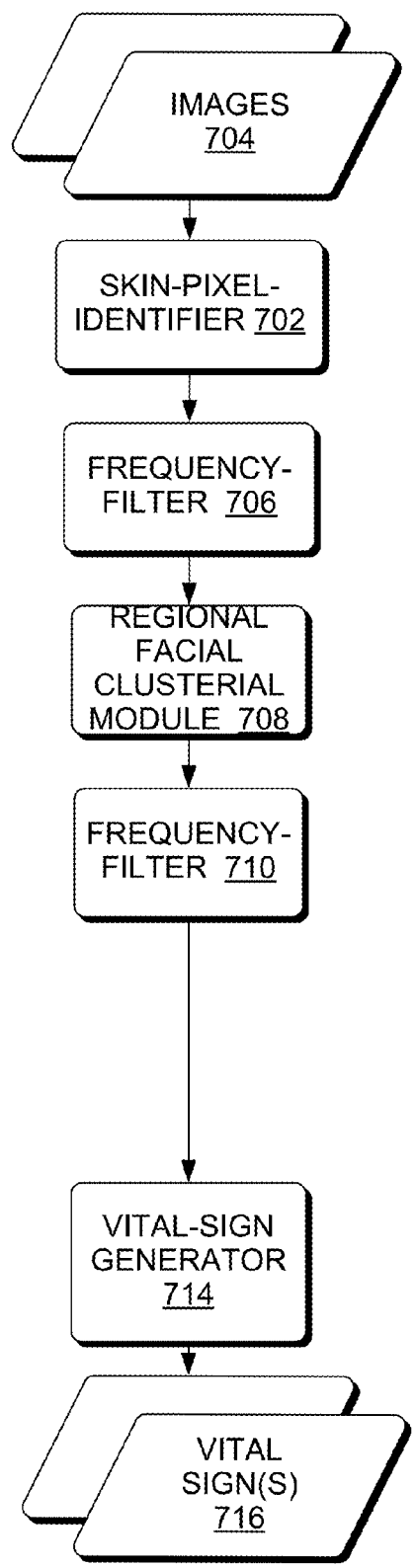
FIG. 8 is a block diagram of an apparatus of motion amplification, according to an implementation.

FIG. 8 is a block diagram of an apparatus 800 of motion amplification, according to an implementation. Apparatus 800 analyzes the temporal and spatial variations in digital images of an animal subject in order to generate and communicate biological vital signs.

In some implementations, apparatus 800 includes a skin-pixel-identifier 702 that identifies pixel values that are representative of the skin in two or more images 704. The skin-pixel-identifier 702 performs block 1602 in FIG. 16. Some implementations of the skin-pixel-identifier 702 performs an automatic seed point based clustering process on the least two images 704.

In some implementations, apparatus 800 includes a frequency filter 706 that receives the output of the skin-pixel-identifier 702 and applies a frequency filter to the output of the skin-pixel-identifier 702. The frequency filter 706 performs block 1604 in FIG. 16 to process the images 704 in the frequency domain.

In some implementations, apparatus 800 includes a regional facial clusterial module 708 that applies spatial clustering to the output of the frequency filter 706. The regional facial clusterial module 708 performs block 1606 in FIG. 16. In some implementations the regional facial clusterial module 708 includes fuzzy clustering, k-means clustering, expectation-maximization process, Ward's apparatus or seed point based clustering.

In some implementations, apparatus 800 includes a frequency-filter 710 that applies a frequency filter to the output of the regional facial clusterial module 708, to generate a temporal variation. The frequency-filter 710 performs block 1608 in FIG. 16. In some implementations, the frequency-filter 710 is a one-dimensional spatial Fourier Transform, a high pass filter, a low pass filter, a bandpass filter or a weighted bandpass filter. Some implementations of frequency-filter 710 includes de-noising (e.g. smoothing of the data with a Gaussian filter). The skin-pixel-identifier 702, the frequency filter 706, the regional facial clusterial module 708 and the frequency-filter 710 amplify temporal variations in the two or more images 704.

In some implementations, apparatus 800 includes a vital-sign generator 714 that generates one or more vital sign(s) 716 from the temporal variation. The vital sign(s) 716 are displayed for review by a healthcare worker or stored in a volatile or nonvolatile memory for later analysis, or transmitted to other devices for analysis.

Figure 9:
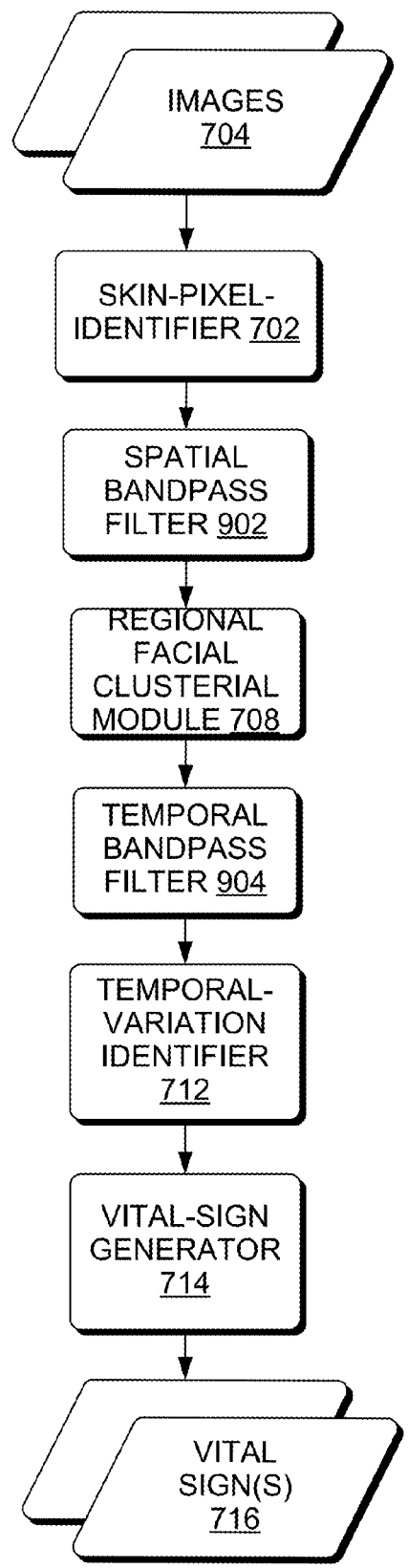
FIG. 9 is a block diagram of an apparatus of motion amplification, according to an implementation.

FIG. 9 is a block diagram of an apparatus 900 of motion amplification, according to an implementation. Apparatus 900 analyzes the temporal and spatial variations in digital images of an animal subject in order to generate and communicate biological vital signs.

In some implementations, apparatus 900 includes a skin-pixel-identifier 702 that identifies pixel values that are representative of the skin in two or more images 704. The skin-pixel-identifier 702 performs block 1602 in FIG. 16. Some implementations of the skin-pixel-identifier 702 performs an automatic seed point based clustering process on the least two images 704.

In some implementations, apparatus 900 includes a spatial bandpass filter 902 that receives the output of the skin-pixel-identifier 702 and applies a spatial bandpass filter to the output of the skin-pixel-identifier 702. The spatial bandpass filter 902 performs block 1802 in FIG. 18 to process the images 704 in the spatial domain.

In some implementations, apparatus 900 includes a regional facial clusterial module 708 that applies spatial clustering to the output of the frequency filter 706. The regional facial clusterial module 708 performs block 1804 in FIG. 18. In some implementations the regional facial clusterial module 708 includes fuzzy clustering, k-means clustering, expectation-maximization process, Ward's apparatus or seed point based clustering.

In some implementations, apparatus 900 includes a temporal bandpass filter 904 that applies a frequency filter to the output of the regional facial clusterial module 708. The temporal bandpass filter 904 performs block 1806 in FIG. 18. In some implementations, the temporal bandpass filter 904 is a one-dimensional spatial Fourier Transform, a high pass filter, a low pass filter, a bandpass filter or a weighted bandpass filter. Some implementations of temporal bandpass filter 904 includes de-noising (e.g. smoothing of the data with a Gaussian filter).

The skin-pixel-identifier 702, the spatial bandpass filter 902, the regional facial clusterial module 708 and the temporal bandpass filter 904 amplify temporal variations in the two or more images 704.

In some implementations, apparatus 900 includes a temporal-variation identifier 712 that identifies temporal variation of the output of the frequency-filter 710. Thus, the temporal variation represents temporal variation of the images 704. The temporal-variation identifier 712 performs block 1808 in FIG. 18.

In some implementations, apparatus 900 includes a vital-sign generator 714 that generates one or more vital sign(s) 716 from the temporal variation. The vital sign(s) 716 are displayed for review by a healthcare worker or stored in a volatile or nonvolatile memory for later analysis, or transmitted to other devices for analysis.

Figure 10:
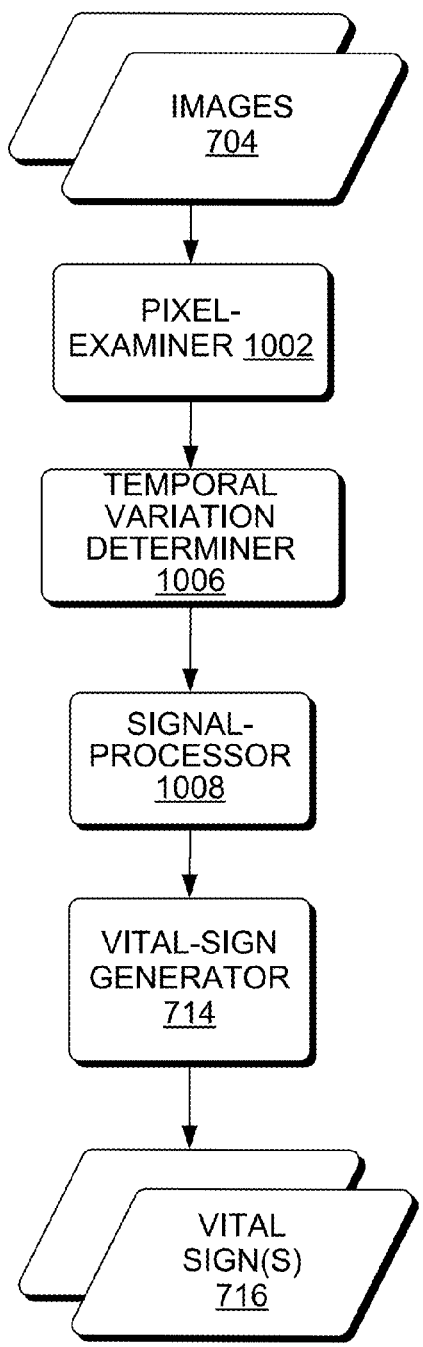
FIG. 10 is a block diagram of an apparatus of motion amplification, according to an implementation.

FIG. 10 is a block diagram of an apparatus 1000 of motion amplification, according to an implementation.

In some implementations, apparatus 1000 includes a pixel-examiner 1002 that examines pixel values of two or more images 704. The pixel-examiner 1002 performs block 1902 in FIG. 19.

In some implementations, apparatus 1000 includes a temporal variation determiner 1006 that determines a temporal variation of examined pixel values. The temporal variation determiner 1006 performs block 1904 in FIG. 19.

In some implementations, apparatus 1000 includes a signal-processor 1008 that applies signal processing to the pixel value temporal variation, generating an amplified temporal variation. The signal-processor 1008 performs block 1906 in FIG. 19. The signal processing amplifies the temporal variation, even when the temporal variation is small. In some implementations, the signal processing performed by signal-processor 1008 is temporal bandpass filtering that analyzes frequencies over time. In some implementations, the signal processing performed by signal-processor 1008 is spatial processing that removes noise. Apparatus 1000 amplifies only small temporal variations in the signal-processing module.

In some implementations, apparatus 900 includes a vital-sign generator 714 that generates one or more vital sign(s) 716 from the temporal variation. The vital sign(s) 716 are displayed for review by a healthcare worker or stored in a volatile or nonvolatile memory for later analysis, or transmitted to other devices for analysis.

While apparatus 1000 can process large temporal variations, an advantage in apparatus 1000 is provided for small temporal variations. Therefore apparatus 1000 is most effective when the two or more images 704 have small temporal variations between the two or more images 704. In some implementations, a vital sign is generated from the amplified temporal variations of the two or more images 704 from the signal-processor 1008.

Figure 11:
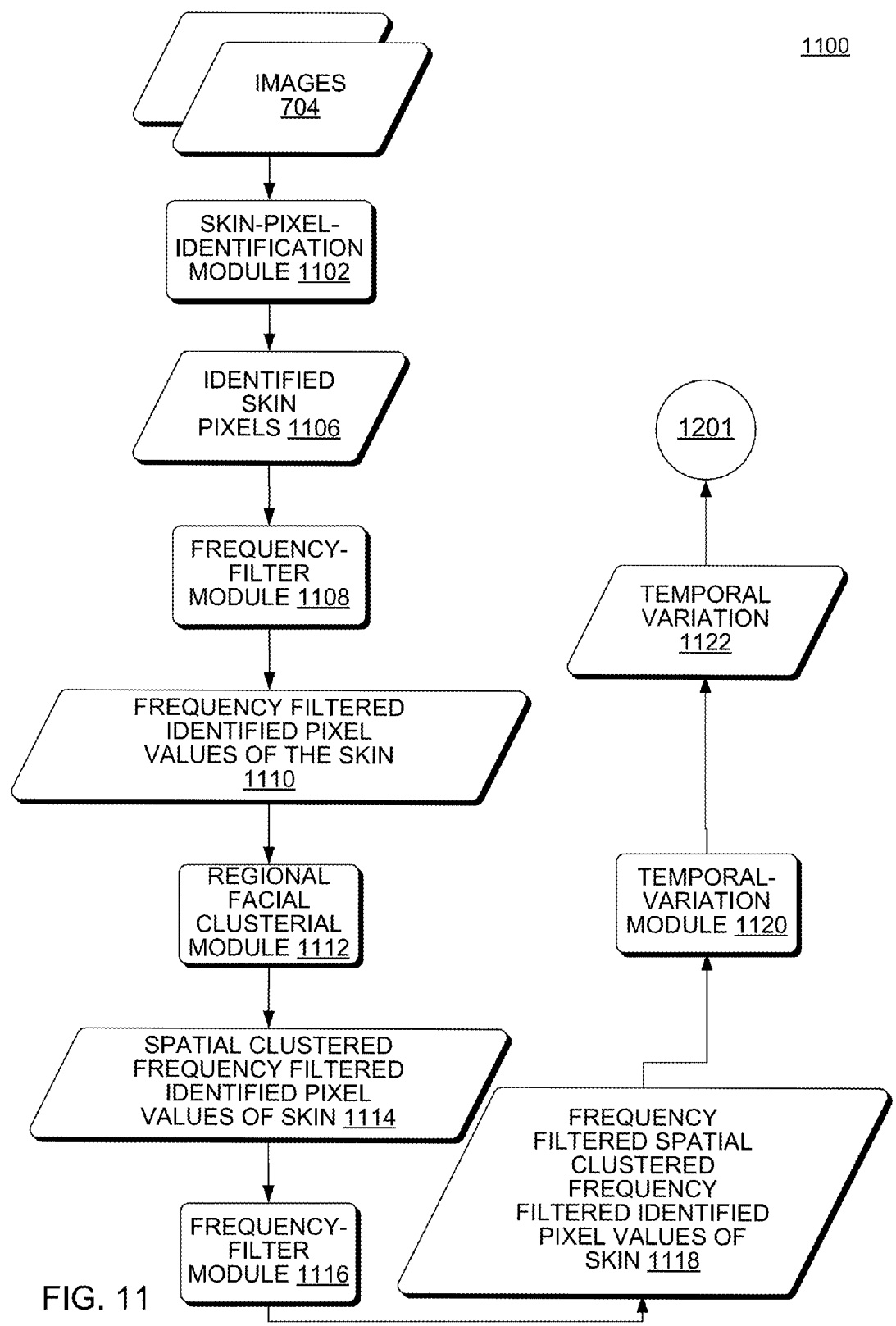
FIG. 11 is a block diagram of an apparatus of motion amplification, according to an implementation.

FIG. 11 is a block diagram of an apparatus 1100 of motion amplification, according to an implementation. Apparatus 1100 analyzes the temporal and spatial variations in digital images of an animal subject in order to generate and communicate biological vital signs.

In some implementations, apparatus 1100 includes a skin-pixel-identification module 1102 that identifies pixel values 1106 that are representative of the skin in two or more images 1104. The skin-pixel-identification module 1102 performs block 1602 in FIG. 16. Some implementations of the skin-pixel-identification module 1102 perform an automatic seed point based clustering process on the least two images 1104.

In some implementations, apparatus 1100 includes a frequency-filter module 1108 that receives the identified pixel values 1106 that are representative of the skin and applies a frequency filter to the identified pixel values 1106. The frequency-filter module 1108 performs block 1604 in FIG. 16 to process the images 704 in the frequency domain. Each of the images 704 is Fourier transformed, multiplied with a filter function and then re-transformed into the spatial domain. Frequency filtering is based on the Fourier Transform. The operator takes an image 704 and a filter function in the Fourier domain. The image 704 is then multiplied with the filter function in a pixel-by-pixel fashion using the formula:

$$G(k, l) = F(k, l) H(k, l)$$

where F(k,l) is the input image 704 of identified pixel values 1106 in the Fourier domain, H(k,l) the filter function and G(k,l) is the filtered image 1110. To obtain the resulting image in the spatial domain, G(k,l) is re-transformed using the inverse Fourier Transform. In some implementations, the frequency-filter module 1108 is a two-dimensional spatial Fourier Transform, a high pass filter, a low pass filter, a bandpass filter or a weighted bandpass filter.

In some implementations, apparatus 1100 includes a spatial-cluster module 1112 that applies spatial clustering to the frequency filtered identified pixel values of skin 1110, generating spatial clustered frequency filtered identified pixel values of skin 1114. The spatial-cluster module 1112 performs block 1606 in FIG. 16. In some implementations the spatial-cluster module 1112 includes fuzzy clustering, k-means clustering, expectation-maximization process, Ward's apparatus or seed point based clustering.

In some implementations, apparatus 1100 includes a frequency-filter module 1116 that applies a frequency filter to the spatial clustered frequency filtered identified pixel values of skin 1114, which generates frequency filtered spatial clustered frequency filtered identified pixel values of skin 1118. The frequency-filter module 1116 performs block 1608 in FIG. 16. In some implementations, the frequency-filter module 1116 is a one-dimensional spatial Fourier Transform, a high pass filter, a low pass filter, a bandpass filter or a weighted bandpass filter. Some implementations of frequency-filter module 1116 includes de-noising (e.g. smoothing of the data with a Gaussian filter).

The skin-pixel-identification module 1102, the frequency-filter module 1108, the spatial-cluster module 1112 and the frequency-filter module 1116 amplify temporal variations in the two or more images 704.

In some implementations, apparatus 1100 includes a temporal-variation module 1120 that determines temporal variation 1122 of the frequency filtered spatial clustered frequency filtered identified pixel values of skin 1118. Thus, temporal variation 1122 represents temporal variation of the images 704. The temporal-variation module 1120 performs block 1610 in FIG. 16.

Figure 12:
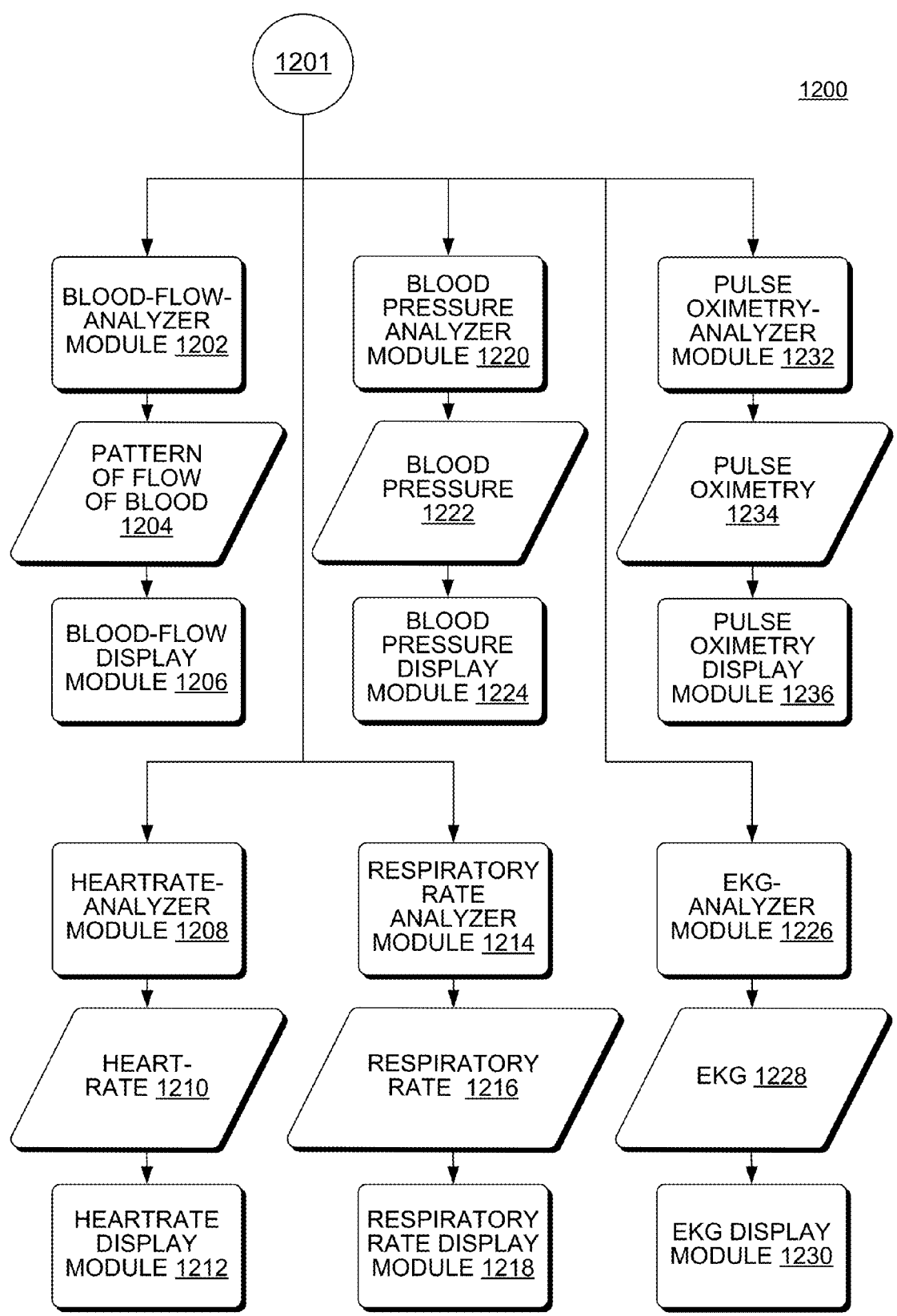
FIG. 12 is a block diagram of an apparatus to generate and present any one of a number of biological vital signs from amplified motion, according to an implementation.

FIG. 12 is a block diagram of an apparatus 1200 to generate and present any one of a number of biological vital signs from amplified motion, according to an implementation.

In some implementations, apparatus 1200 includes a blood-flow-analyzer module 1202 that analyzes a temporal variation to generate a pattern of flow of blood 1204. One example of the temporal variation is temporal variation 1122 in FIG. 11. In some implementations, the pattern flow of blood 1204 is generated from motion changes in the pixels and the temporal variation of color changes in the skin of the images 704. In some implementations, apparatus 1200 includes a blood-flow display module 1206 that displays the pattern of flow of blood 1204 for review by a healthcare worker.

In some implementations, apparatus 1200 includes a heartrate-analyzer module 1208 that analyzes the temporal variation to generate a heartrate 1210. In some implementations, the heartrate 1210 is generated from the frequency spectrum of the temporal signal in a frequency range for heart beats, such as (0-10 Hertz). In some implementations, apparatus 1200 includes a heartrate display module 1212 that displays the heartrate 1210 for review by a healthcare worker.

In some implementations, apparatus 1200 includes a respiratory rate-analyzer module 1214 that analyzes the temporal variation to determine a respiratory rate 1216. In some implementations, the respiratory rate 1216 is generated from the motion of the pixels in a frequency range for respiration (0-5 Hertz). In some implementations, apparatus 1200 includes respiratory rate display module 1218 that displays the respiratory rate 1216 for review by a healthcare worker.

In some implementations, apparatus 1200 includes a blood-pressure analyzer module 1220 that analyzes the temporal variation to a generate blood pressure 1222. In some implementations, the blood-pressure analyzer module 1220 generates the blood pressure 1222 by analyzing the motion of the pixels and the color changes based on a clustering process and potentially temporal data. In some implementations, apparatus 1200 includes a blood pressure display module 1224 that displays the blood pressure 1222 for review by a healthcare worker.

In some implementations, apparatus 1200 includes an EKG analyzer module 1226 that analyzes the temporal variation to generate an EKG 1228. In some implementations, apparatus 1200 includes an EKG display module 1230 that displays the EKG 1228 for review by a healthcare worker.

In some implementations, apparatus 1200 includes a pulse oximetry analyzer module 1232 that analyzes the temporal variation to generate pulse oximetry 1234. In some implementations, the pulse oximetry analyzer module 1232 generates the pulse oximetry 1234 by analyzing the temporal color changes based in conjunction with the k-means clustering process and potentially temporal data. In some implementations, apparatus 1200 includes a pulse oximetry display module 1236 that displays the pulse oximetry 1234 for review by a healthcare worker.

Figure 13:
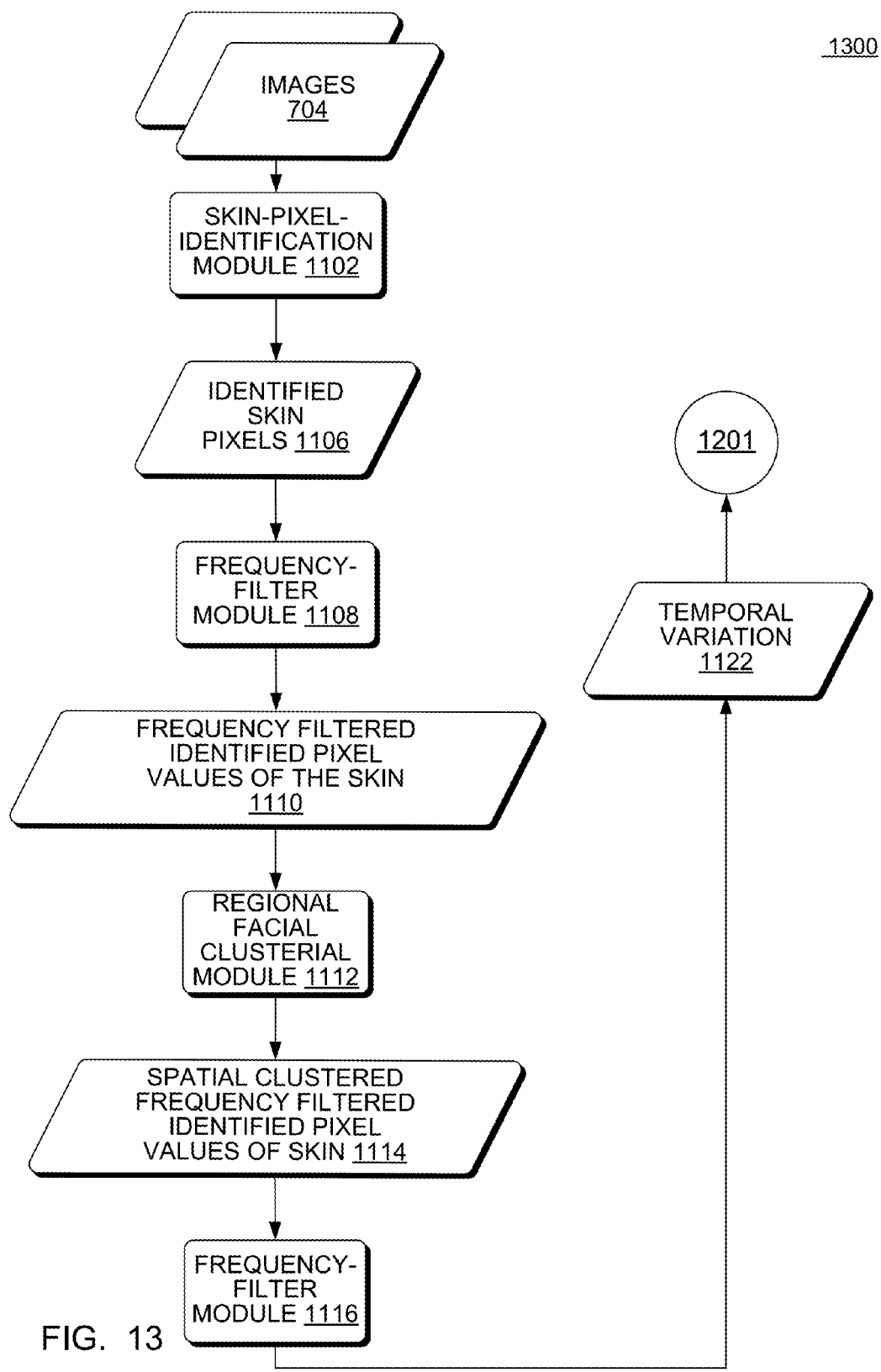
FIG. 13 is a block diagram of an apparatus of motion amplification, according to an implementation.

FIG. 13 is a block diagram of an apparatus 1300 of motion amplification, according to an implementation. Apparatus 1300 analyzes the temporal and spatial variations in digital images of an animal subject in order to generate and communicate biological vital signs.

In some implementations, apparatus 1300 includes a skin-pixel-identification module 1102 that identifies pixel values 1106 that are representative of the skin in two or more images 704. The skin-pixel-identification module 1102 performs block 1602 in FIG. 16. Some implementations of the skin-pixel-identification module 1102 perform an automatic seed point based clustering process on the least two images 704.

In some implementations, apparatus 1300 includes a frequency-filter module 1108 that receives the identified pixel values 1106 that are representative of the skin and applies a frequency filter to the identified pixel values 1106. The frequency-filter module 1108 performs block 1604 in FIG. 16 to process the images 704 in the frequency domain. Each of the images 704 is Fourier transformed, multiplied with a filter function and then re-transformed into the spatial domain. Frequency filtering is based on the Fourier Transform. The operator takes an image 704 and a filter function in the Fourier domain. The image 704 is then multiplied with the filter function in a pixel-by-pixel fashion using the formula:

$$G(k, l) = F(k, l)H(k, l)$$

where $F(k,l)$ is the input image 704 of identified pixel values 1106 in the Fourier domain, $H(k,l)$ the filter function and $G(k,l)$ is the filtered image 1110. To obtain the resulting image in the spatial domain, $G(k,l)$ is re-transformed using the inverse Fourier Transform. In some implementations, the frequency-filter module 1108 is a two-dimensional spatial Fourier Transform, a high pass filter, a low pass filter, a bandpass filter or a weighted bandpass filter.

In some implementations, apparatus 1300 includes a spatial-cluster module 1112 that applies spatial clustering to the frequency filtered identified pixel values of skin 1110, generating spatial clustered frequency filtered identified pixel values of skin 1114. The spatial-cluster module 1112 performs block 1606 in FIG. 16. In some implementations the spatial clustering includes fuzzy clustering, k-means clustering, expectation-maximization process, Ward's apparatus or seed point based clustering.

In some implementations, apparatus 1300 includes a frequency-filter module 1116 that applies a frequency filter to the spatial clustered frequency filtered identified pixel values of skin 1114, which generates frequency filtered spatial clustered frequency filtered identified pixel values of skin 1118. The frequency-filter module 1116 performs block 1608 in FIG. 16 to generate a temporal variation 1122. In some implementations, the frequency-filter module 1116 is a one-dimensional spatial Fourier Transform, a high pass filter, a low pass filter, a bandpass filter or a weighted bandpass filter. Some implementations of the frequency-filter module 1116 includes de-noising (e.g. smoothing of the data with a Gaussian filter). The skin-pixel-identification module 1102, the frequency-filter module 1108, the spatial-cluster module 1112 and the frequency-filter module 1116 amplify temporal variations in the two or more images 704.

The frequency-filter module 1116 is operably coupled to one of more modules in FIG. 12 to generate and present any one or a number of biological vital signs from amplified motion in the temporal variation 1122.

Figure 14:
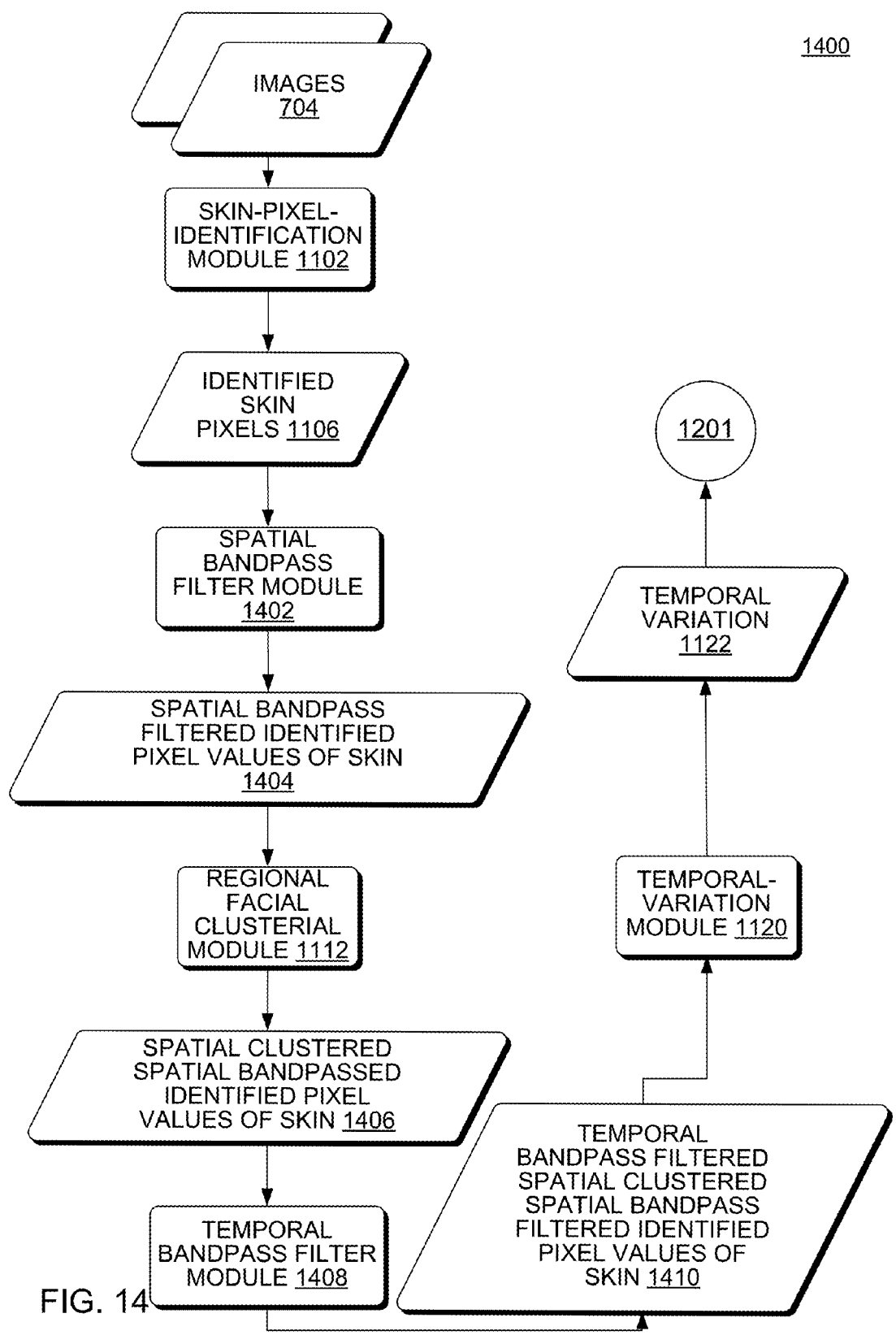
FIG. 14 is a block diagram of an apparatus of motion amplification, according to an implementation.

FIG. 14 is a block diagram of an apparatus 1400 of motion amplification, according to an implementation. Apparatus 1400 analyzes the temporal and spatial variations in digital images of an animal subject in order to generate and communicate biological vital signs.

In some implementations, apparatus 1400 includes a skin-pixel-identification module 1102 that identifies pixel values 1106 that are representative of the skin in two or more images 704. The skin-pixel-identification module 1102 performs block 1602 in FIG. 18. Some implementations of the skin-pixel-identification module 1102 perform an automatic seed point based clustering process on the least two images 704. In some implementations, apparatus 1400 includes a spatial bandpass filter module 1402 that applies a spatial bandpass filter to the identified pixel values 1106, generating spatial bandpassed filtered identified pixel values of skin 1404. In some implementations, the spatial bandpass filter module 1402 includes a two-dimensional spatial Fourier Transform, a high pass filter, a low pass filter, a bandpass filter or a weighted bandpass filter. The spatial bandpass filter module 1402 performs block 1802 in FIG. 18.

In some implementations, apparatus 1400 includes a spatial-cluster module 1112 that applies spatial clustering to the frequency filtered identified pixel values of skin 1110, generating spatial clustered spatial bandpassed identified pixel values of skin 1406. In some implementations the spatial clustering includes fuzzy clustering, k-means clustering, expectation-maximization process, Ward's apparatus or seed point based clustering. The spatial-cluster module 1112 performs block 1804 in FIG. 18.

In some implementations, apparatus 1400 includes a temporal bandpass filter module 1408 that applies a temporal bandpass filter to the spatial clustered spatial bandpass filtered identified pixel values of skin 1406, generating temporal bandpass filtered spatial clustered spatial bandpass filtered identified pixel values of skin 1410. In some implementations, the temporal bandpass filter is a one-dimensional spatial Fourier Transform, a high pass filter, a low pass filter, a bandpass filter or a weighted bandpass filter. The temporal bandpass filter module 1408 performs block 1806 in FIG. 18.

In some implementations, apparatus 1400 includes a temporal-variation module 1120 that determines temporal variation 1522 of the temporal bandpass filtered spatial clustered spatial bandpass filtered identified pixel values of skin 1410. Thus, temporal variation 1522 represents temporal variation of the images 704. The temporal-variation module 1520 performs block 1808 of FIG. 18. The temporal-variation module 1520 is operably coupled to one or more modules in FIG. 12 to generate and present any one of a number of biological vital signs from amplified motion in the temporal variation 1522.

Figure 15:
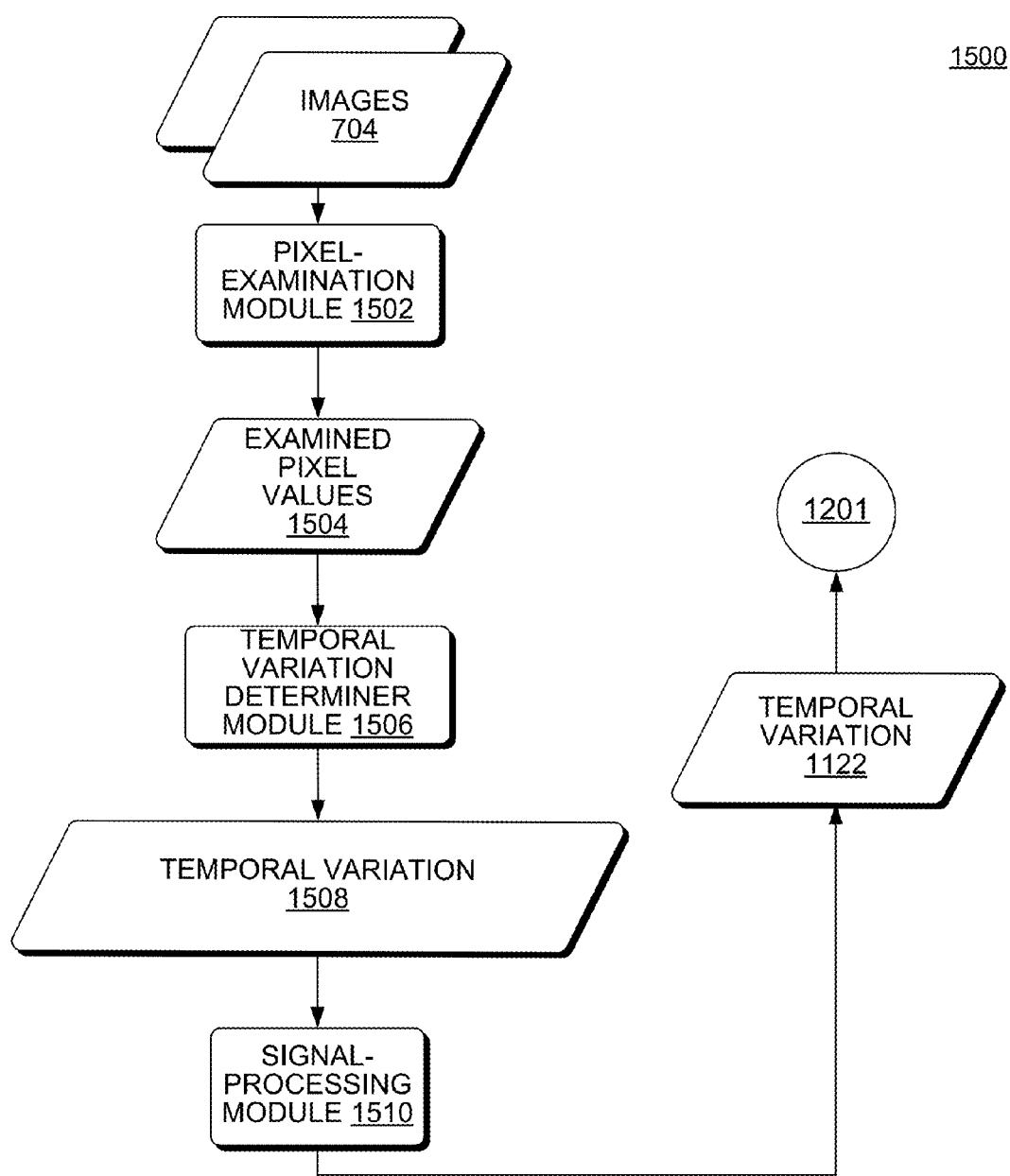
FIG. 15 is an apparatus that performs motion amplification to generate biological vital signs, according to an implementation.

FIG. 15 is a block diagram of an apparatus 1500 of motion amplification, according to an implementation.

In some implementations, apparatus 1500 includes a pixel-examination-module 1502 that examines pixel values of two or more images 704, generating examined pixel values 1504. The pixel-examination-module 1502 performs block 1902 in FIG. 19.

In some implementations, apparatus 1500 includes a temporal variation determiner module 1506 that determines a temporal variation 1508 of the examined pixel values 1504. The temporal variation determiner module 1506 performs block 1904 in FIG. 19.

In some implementations, apparatus 1500 includes a signal-processing module 1510 that applies signal processing to the pixel value temporal variations 1508, generating an amplified temporal variation 1522. The signal-processing module 1510 performs block 1906 in FIG. 19. The signal processing amplifies the temporal variation 1508, even when the temporal variation 1508 is small. In some implementations, the signal processing performed by signal-processing module 1510 is temporal bandpass filtering that analyzes frequencies over time. In some implementations, the signal processing performed by signal-processing module 1510 is spatial processing that removes noise. Apparatus 1500 amplifies only small temporal variations in the signal-processing module.

While apparatus 1500 can process large temporal variations, an advantage in apparatus 1500 is provided for small temporal variations. Therefore apparatus 1500 is most effective when the two or more images 704 have small temporal variations between the two or more images 704. In some implementations, a vital sign is generated from the amplified temporal variations of the two or more images 704 from the signal-processing module 1510.

Vital Sign Motion Amplification Method Implementations

FIG. 16-20 each use spatial and temporal signal processing to generate vital signs from a series of digital images.

Figure 16:
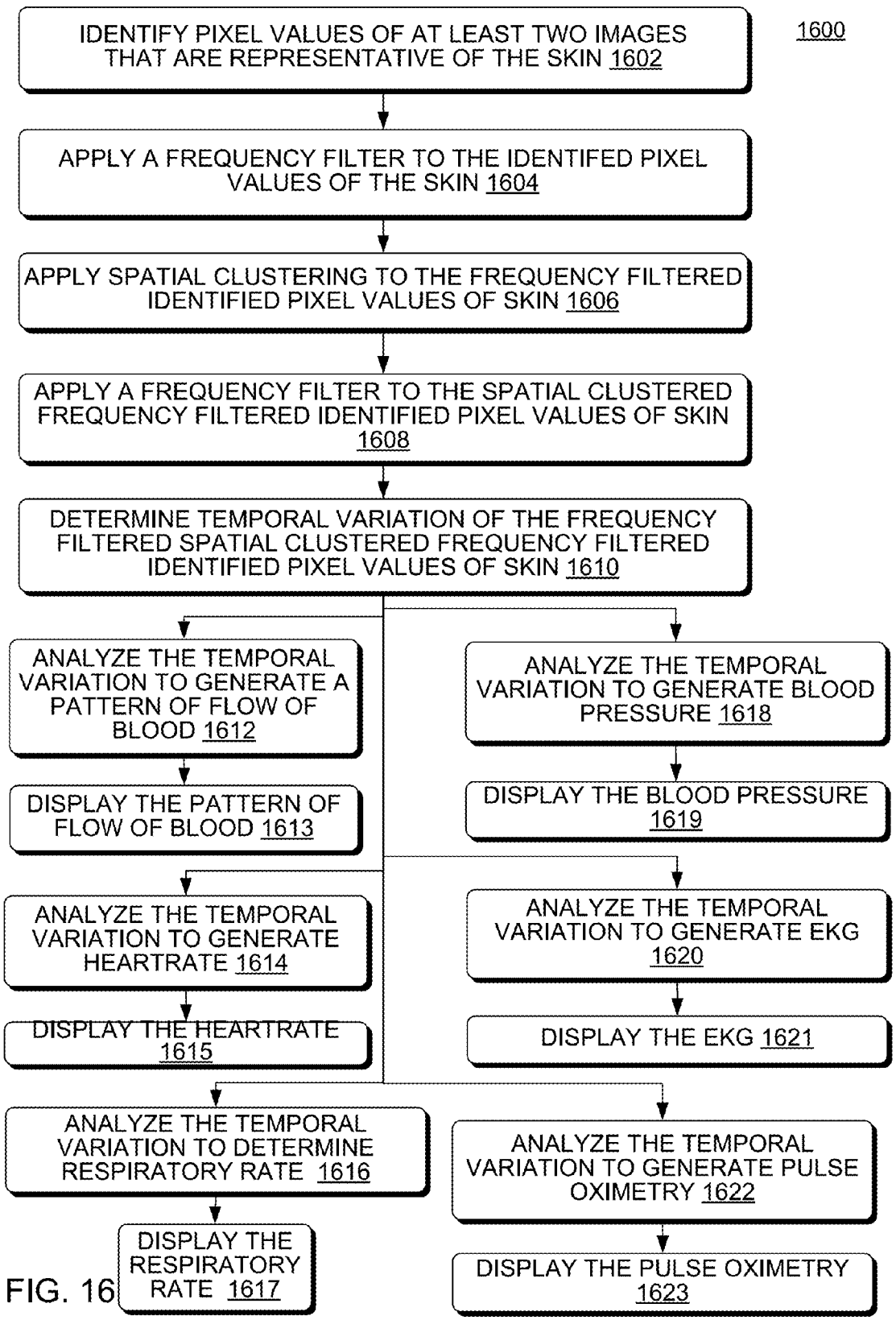
FIG. 16 is a flowchart of a method of motion amplification, according to an implementation.

FIG. 16 is a flowchart of a method 1600 of motion amplification, according to an implementation. Method 1600 analyzes the temporal and spatial variations in digital images of an animal subject in order to generate and communicate biological vital signs.

In some implementations, method 1600 includes identifying pixel values of two or more images that are representative of the skin, at block 1602. Some implementations of identifying pixel values that are representative of the skin includes performing an automatic seed point based clustering process on the least two images.

In some implementations, method 1600 includes applying a frequency filter to the identified pixel values that are representative of the skin, at block 1604. In some implementations, the frequency filter in block 1604 is a two-dimensional spatial Fourier Transform, a high pass filter, a low pass filter, a bandpass filter or a weighted bandpass filter.

In some implementations, method 1600 includes applying spatial clustering to the frequency filtered identified pixel values of skin, at block 1606. In some implementations the spatial clustering includes fuzzy clustering, k-means clustering, expectation-maximization process, Ward's method or seed point based clustering.

In some implementations, method 1600 includes applying a frequency filter to the spatial clustered frequency filtered identified pixel values of skin, at block 1608. In some implementations, the frequency filter in block 1608 is a one-dimensional spatial Fourier Transform, a high pass filter, a low pass filter, a bandpass filter or a weighted bandpass filter. Some implementations of applying a frequency filter at block 1608 include de-noising (e.g. smoothing of the data with a Gaussian filter).

Actions 1602, 1604, 1606 and 1608 amplify temporal variations in the two or more images.

In some implementations, method 1600 includes determining temporal variation of the frequency filtered spatial clustered frequency filtered identified pixel values of skin, at block 1610.

In some implementations, method 1600 includes analyzing the temporal variation to generate a pattern of flow of blood, at block 1612. In some implementations, the pattern flow of blood is generated from motion changes in the pixels and the temporal variation of color changes in the skin. In some implementations, method 1600 includes displaying the pattern of flow of blood for review by a healthcare worker, at block 1613.

In some implementations, method 1600 includes analyzing the temporal variation to generate heartrate, at block 1614. In some implementations, the heartrate is generated from the frequency spectrum of the temporal variation in a frequency range for heart beats, such as (0-10 Hertz). In some implementations, method 1600 includes displaying the heartrate for review by a healthcare worker, at block 1615.

In some implementations, method 1600 includes analyzing the temporal variation to determine respiratory rate, at block 1616. In some implementations, the respiratory rate is generated from the motion of the pixels in a frequency range for respiration (0-5 Hertz). In some implementations, method 1600 includes displaying the respiratory rate for review by a healthcare worker, at block 1617.

In some implementations, method 1600 includes analyzing the temporal variation to generate blood pressure, at block 1618. In some implementations, the blood pressure is generated by analyzing the motion of the pixels and the color changes based on the clustering process and potentially temporal data from the infrared sensor. In some implementations, method 1600 includes displaying the blood pressure for review by a healthcare worker, at block 1619.

In some implementations, method 1600 includes analyzing the temporal variation to generate EKG, at block 1620. In some implementations, method 1600 includes displaying the EKG for review by a healthcare worker, at block 1621.

In some implementations, method 1600 includes analyzing the temporal variation to generate pulse oximetry, at block 1622. In some implementations, the pulse oximetry is generated by analyzing the temporal color changes based in conjunction with the k-means clustering process and potentially temporal data from the infrared sensor. In some implementations, method 1600 includes displaying the pulse oximetry for review by a healthcare worker, at block 1623.

Figure 17:
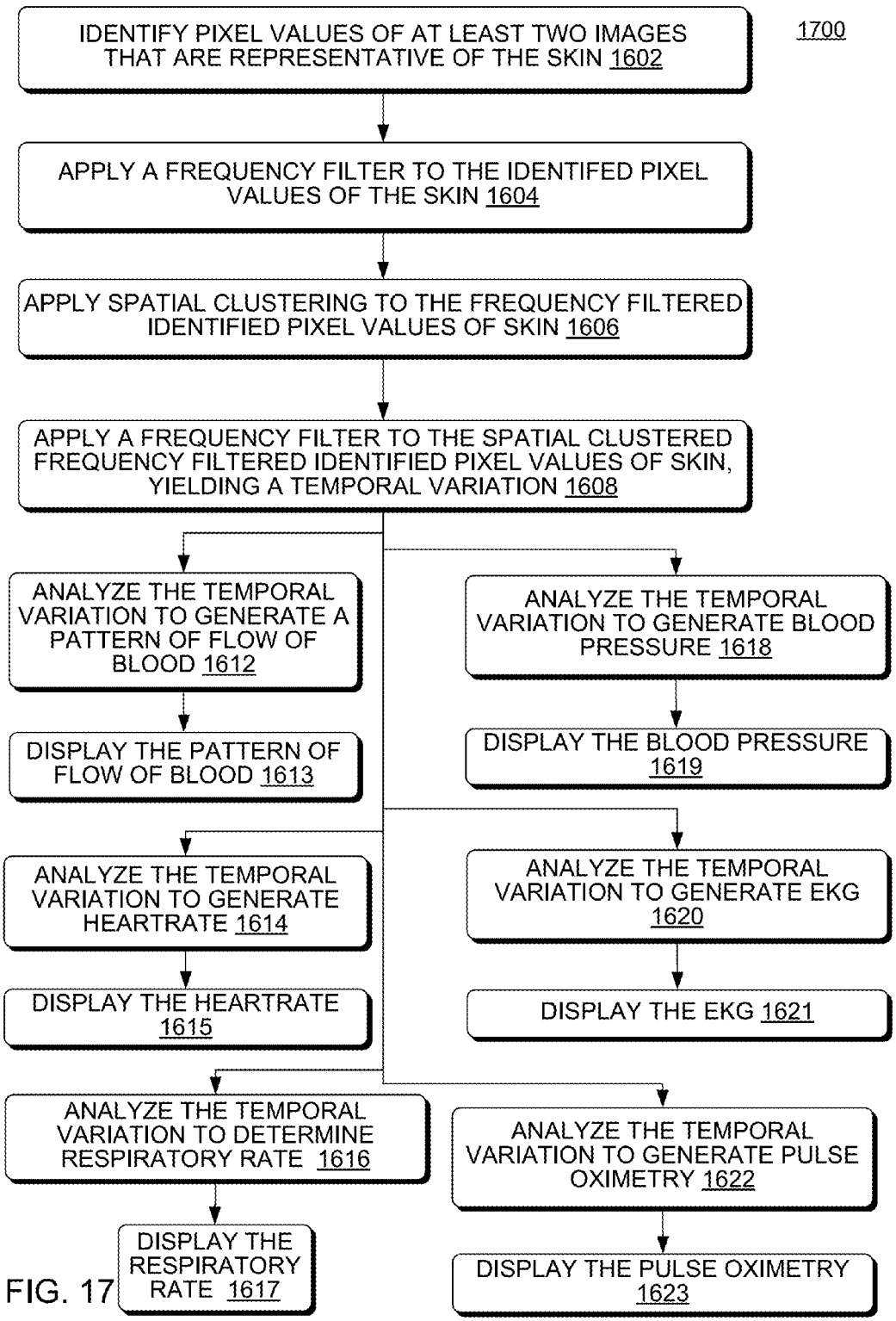
FIG. 17 is a flowchart of a method of motion amplification, according to an implementation that does not include a separate action of determining a temporal variation.

FIG. 17 is a flowchart of a method of motion amplification, according to an implementation that does not include a separate action of determining a temporal variation. Method 1700 analyzes the temporal and spatial variations in digital images of an animal subject in order to generate and communicate biological vital signs.

In some implementations, method 1700 includes identifying pixel values of two or more images that are representative of the skin, at block 1602. Some implementations of identifying pixel values that are representative of the skin includes performing an automatic seed point based clustering process on the least two images.

In some implementations, method 1700 includes applying a frequency filter to the identified pixel values that are representative of the skin, at block 1604. In some implementations, the frequency filter in block 1604 is a two-dimensional spatial Fourier Transform, a high pass filter, a low pass filter, a bandpass filter or a weighted bandpass filter.

In some implementations, method 1700 includes applying spatial clustering to the frequency filtered identified pixel values of skin, at block 1606. In some implementations the spatial clustering includes fuzzy clustering, k-means clustering, expectation-maximization process, Ward's method or seed point based clustering.

In some implementations, method 1700 includes applying a frequency filter to the spatial clustered frequency filtered identified pixel values of skin, at block 1608, yielding a temporal variation. In some implementations, the frequency filter in block 1608 is a one-dimensional spatial Fourier Transform, a high pass filter, a low pass filter, a bandpass filter or a weighted bandpass filter.

In some implementations, method 1700 includes analyzing the temporal variation to generate a pattern of flow of blood, at block 1612. In some implementations, the pattern flow of blood is generated from motion changes in the pixels and the temporal variation of color changes in the skin. In some implementations, method 1700 includes displaying the pattern of flow of blood for review by a healthcare worker, at block 1613.

In some implementations, method 1700 includes analyzing the temporal variation to generate heartrate, at block 1614. In some implementations, the heartrate is generated from the frequency spectrum of the temporal variation in a frequency range for heart beats, such as (0-10 Hertz). In some implementations, method 1700 includes displaying the heartrate for review by a healthcare worker, at block 1615.

In some implementations, method 1700 includes analyzing the temporal variation to determine respiratory rate, at block 1616. In some implementations, the respiratory rate is generated from the motion of the pixels in a frequency range for respiration (0-5 Hertz). In some implementations, method 1700 includes displaying the respiratory rate for review by a healthcare worker, at block 1617.

In some implementations, method 1700 includes analyzing the temporal variation to generate blood pressure, at block 1618. In some implementations, the blood pressure is generated by analyzing the motion of the pixels and the color changes based on the clustering process and potentially temporal data from the infrared sensor. In some implementations, method 1700 includes displaying the blood pressure for review by a healthcare worker, at block 1619.

In some implementations, method 1700 includes analyzing the temporal variation to generate EKG, at block 1620. In some implementations, method 1700 includes displaying the EKG for review by a healthcare worker, at block 1621.

In some implementations, method 1700 includes analyzing the temporal variation to generate pulse oximetry, at block 1622. In some implementations, the pulse oximetry is generated by analyzing the temporal color changes based in conjunction with the k-means clustering process and potentially temporal data from the infrared sensor. In some implementations, method 1700 includes displaying the pulse oximetry for review by a healthcare worker, at block 1623.

Figure 18:
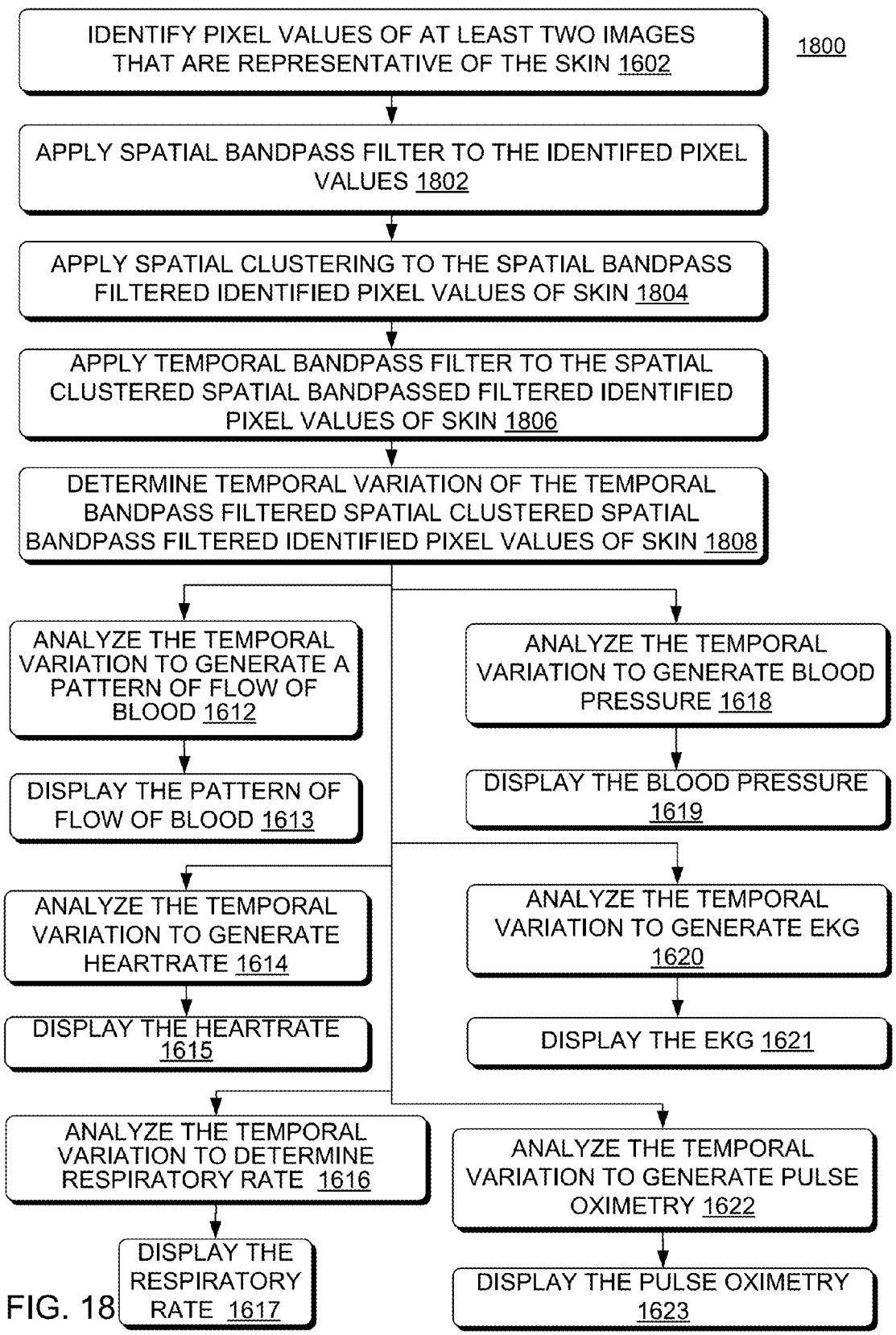
FIG. 18 is a flowchart of a method of motion amplification, according to an implementation.

FIG. 18 is a flowchart of a method 1800 of motion amplification from which to generate and communicate biological vital signs, according to an implementation. Method 1800 analyzes the temporal and spatial variations in digital images of an animal subject in order to generate and communicate the biological vital signs.

In some implementations, method 1800 includes identifying pixel values of two or more images that are representative of the skin, at block 1602. Some implementations of identifying pixel values that are representative of the skin includes performing an automatic seed point based clustering process on the least two images.

In some implementations, method 1800 includes applying a spatial bandpass filter to the identified pixel values, at block 1802. In some implementations, the spatial filter in block 1802 is a two-dimensional spatial Fourier Transform, a high pass filter, a low pass filter, a bandpass filter or a weighted bandpass filter.

In some implementations, method 1800 includes applying spatial clustering to the spatial bandpass filtered identified pixel values of skin, at block 1804. In some implementations the spatial clustering includes fuzzy clustering, k-means clustering, expectation-maximization process, Ward's method or seed point based clustering.

In some implementations, method 1800 includes applying a temporal bandpass filter to the spatial clustered spatial bandpass filtered identified pixel values of skin, at block 1806. In some implementations, the temporal bandpass filter in block 1806 is a one-dimensional spatial Fourier Transform, a high pass filter, a low pass filter, a bandpass filter or a weighted bandpass filter.

In some implementations, method 1800 includes determining temporal variation of the temporal bandpass filtered spatial clustered spatial bandpass filtered identified pixel values of skin, at block 1808.

In some implementations, method 1800 includes analyzing the temporal variation to generate and visually display a pattern of flow of blood, at block 1612. In some implementations, the pattern flow of blood is generated from motion changes in the pixels and the temporal variation of color changes in the skin. In some implementations, method 1800 includes displaying the pattern of flow of blood for review by a healthcare worker, at block 1613.

In some implementations, method 1800 includes analyzing the temporal variation to generate heartrate, at block 1614. In some implementations, the heartrate is generated from the frequency spectrum of the temporal variation in a frequency range for heart beats, such as (0-10 Hertz). In some implementations, method 1800 includes displaying the heartrate for review by a healthcare worker, at block 1615.

In some implementations, method 1800 includes analyzing the temporal variation to determine respiratory rate, at block 1616. In some implementations, the respiratory rate is generated from the motion of the pixels in a frequency range for respiration (0-5 Hertz). In some implementations, method 1800 includes displaying the respiratory rate for review by a healthcare worker, at block 1617.

In some implementations, method 1800 includes analyzing the temporal variation to generate blood pressure, at block 1618. In some implementations, the blood pressure is generated by analyzing the motion of the pixels and the color changes based on the clustering process and potentially temporal data from the infrared sensor. In some implementations, method 1800 includes displaying the blood pressure for review by a healthcare worker, at block 1619.

In some implementations, method 1800 includes analyzing the temporal variation to generate EKG, at block 1620. In some implementations, method 1800 includes displaying the EKG for review by a healthcare worker, at block 1621.

In some implementations, method 1800 includes analyzing the temporal variation to generate pulse oximetry, at block 1622. In some implementations, the pulse oximetry is generated by analyzing the temporal color changes based in conjunction with the k-means clustering process and potentially temporal data from the infrared sensor. In some implementations, method 1800 includes displaying the pulse oximetry for review by a healthcare worker, at block 1623.

Figure 19:
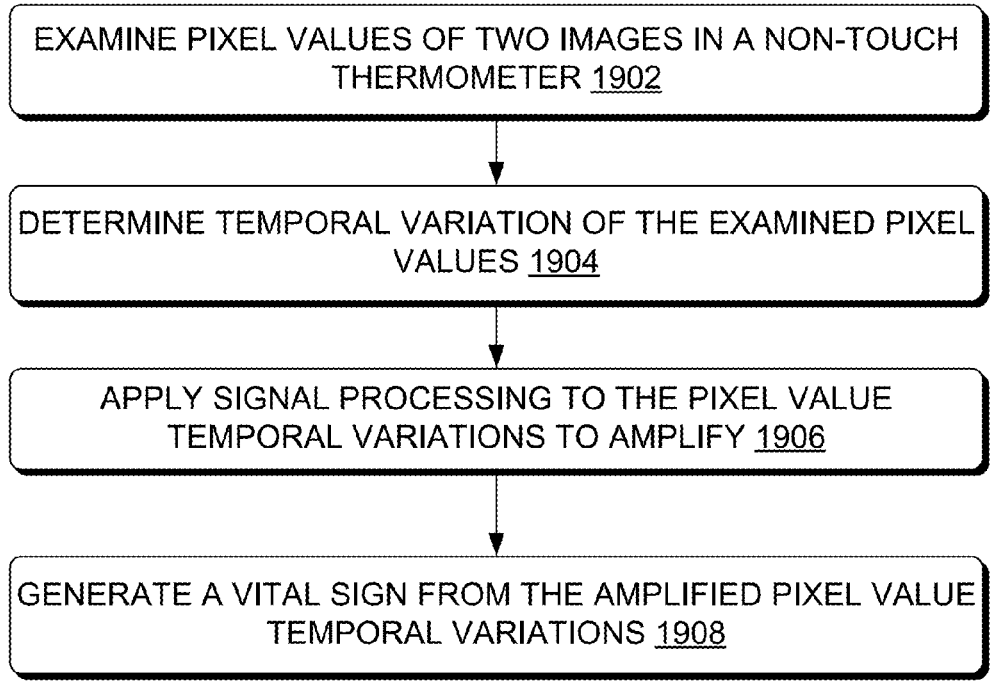
FIG. 19 is a flowchart of a method of motion amplification, according to an implementation.

FIG. 19 is a flowchart of a method 1900 of motion amplification, according to an implementation. Method 1900 displays the temporal variations based on temporal variations in videos that are difficult or impossible to see with the naked eye. Method 1900 applies spatial decomposition to a video, and applies temporal filtering to the frames. The resulting signal is then amplified to reveal hidden information. Method 1900 can visualize flow of blood filling a face in the video and also amplify and reveal small motions, and other vital signs such as blood pressure, respiration, EKG and pulse. Method 1900 can execute in real time to show phenomena occurring at temporal frequencies selected by the operator. A combination of spatial and temporal processing of videos can amplify subtle variations that reveal important aspects of the world. Method 1900 considers a time series of color values at any spatial location (e.g., a pixel) and amplifies variation in a given temporal frequency band of interest. For example, method 1900 selects and then amplifies a band of temporal frequencies including plausible human heart rates. The amplification reveals the variation of redness as blood flows through the face. Lower spatial frequencies are temporally filtered (spatial pooling) to allow a subtle input signal to rise above the camera sensor and quantization noise. The temporal filtering approach not only amplifies color variation, but can also reveal low-amplitude motion.

Method 1900 can enhance the subtle motions around the chest of a breathing baby. Method 1900 mathematical analysis employs a linear approximation related to the brightness constancy assumption used in optical flow formulations. Method 1900 also derives the conditions under which the linear approximation holds. The derivation leads to a multiscale approach to magnify motion without feature tracking or motion estimation. Properties of a voxel of fluid are observed, such as pressure and velocity, which evolve over time. Method 1900 studies and amplifies the variation of pixel values over time, in a spatially-multiscale manner. The spatially-multiscale manner to motion magnification does not explicitly estimate motion, but rather exaggerates motion by amplifying temporal color changes at fixed positions. Method 1900 employs differential approximations that form the basis of optical flow processes. Method 1900 described herein employs localized spatial pooling and bandpass filtering to extract and reveal visually the signal corresponding to the pulse. The domain analysis allows amplification and visualization of the pulse signal at each location on the face. Asymmetry in facial blood flow can be a symptom of arterial problems.

Method 1900 described herein makes imperceptible motions visible using a multiscale approach. Method 1900 amplifies small motions, in one embodiment. Nearly invisible changes in a dynamic environment can be revealed through spatio-temporal processing of standard monocular video sequences. Moreover, for a range of amplification values that is suitable for various applications, explicit motion estimation is not required to amplify motion in natural videos. Method 1900 is well suited to small displacements and lower spatial frequencies. Single framework can amplify both spatial motion and purely temporal changes (e.g., a heart pulse) and can be adjusted to amplify particular temporal frequencies. A spatial decomposition module decomposes the input video into different spatial frequency bands, then applies the same temporal filter to the spatial frequency bands. The outputted filtered spatial bands are then amplified by an amplification factor, added back to the original signal by adders, and collapsed by a reconstruction module to generate the output video. The temporal filter and amplification factors can be tuned to support different applications. For example, the system can reveal unseen motions of a camera, caused by the flipping mirror during a photo burst.

Method 1900 combines spatial and temporal processing to emphasize subtle temporal changes in a video. Method 1900 decomposes the video sequence into different spatial frequency bands. These bands might be magnified differently because (a) the bands might exhibit different signal-to-noise ratios or (b) the bands might contain spatial frequencies for which the linear approximation used in motion magnification does not hold. In the latter case, method 1900 reduces the amplification for these bands to suppress artifacts. When the goal of spatial processing is to increase temporal signal-to-noise ratio by pooling multiple pixels, the method spatially low-pass filters the frames of the video and downsamples the video frames for computational efficiency. In the general case, however, method 1900 computes a full Laplacian pyramid.

Method 1900 then performs temporal processing on each spatial band. Method 1900 considers the time series corresponding to the value of a pixel in a frequency band and applies a bandpass filter to extract the frequency bands of interest. As one example, method 1900 may select frequencies within the range of 0.4-4 Hz, corresponding to 24-240 beats per minute, if the operator wants to magnify a pulse. If method 1900 extracts the pulse rate, then method 1900 can employ a narrow frequency band around that value. The temporal processing is uniform for all spatial levels and for all pixels within each level. Method 1900 then multiplies the extracted bandpassed signal by a magnification factor .alpha. The magnification factor .alpha. can be specified by the operator, and can be attenuated automatically. Method 1900 adds the magnified signal to the original signal and collapses the spatial pyramid to obtain the final output. Since natural videos are spatially and temporally smooth, and since the filtering is performed uniformly over the pixels, the method implicitly maintains spatiotemporal coherency of the results. The motion magnification amplifies small motion without tracking motion. Temporal processing produces motion magnification, shown using an analysis that relies on the first-order Taylor series expansions common in optical flow analyses.

Method 1900 begins with a pixel-examination module in the microprocessor 102 of the non-touch thermometer 100, 200 or 300 examining pixel values of two or more images 704 from the camera 122, at block 1902.

Method 1900 thereafter determines the temporal variation of the examined pixel values, at block 1904 by a temporal-variation module in the microprocessor 102.

A signal-processing module in the microprocessor 102 applies signal processing to the pixel value temporal variations, at block 1906. Signal processing amplifies the determined temporal variations, even when the temporal variations are small. Method 1900 amplifies only small temporal variations in the signal-processing module. While method 1900 can be applied to large temporal variations, an advantage in method 1900 is provided for small temporal variations. Therefore method 1900 is most effective when the input images 704 have small temporal variations between the images 704. In some implementations, the signal processing at block 1906 is temporal bandpass filtering that analyzes frequencies over time. In some implementations, the signal processing at block 1906 is spatial processing that removes noise.

In some implementations, a vital sign is generated from the amplified temporal variations of the input images 704 from the signal processor at block 1908. Examples of generating a vital signal from a temporal variation include as in actions 1612, 1614, 1616, 1618, 1620 and 1622 in FIGS. 16, 17 and 18.

Figure 20:
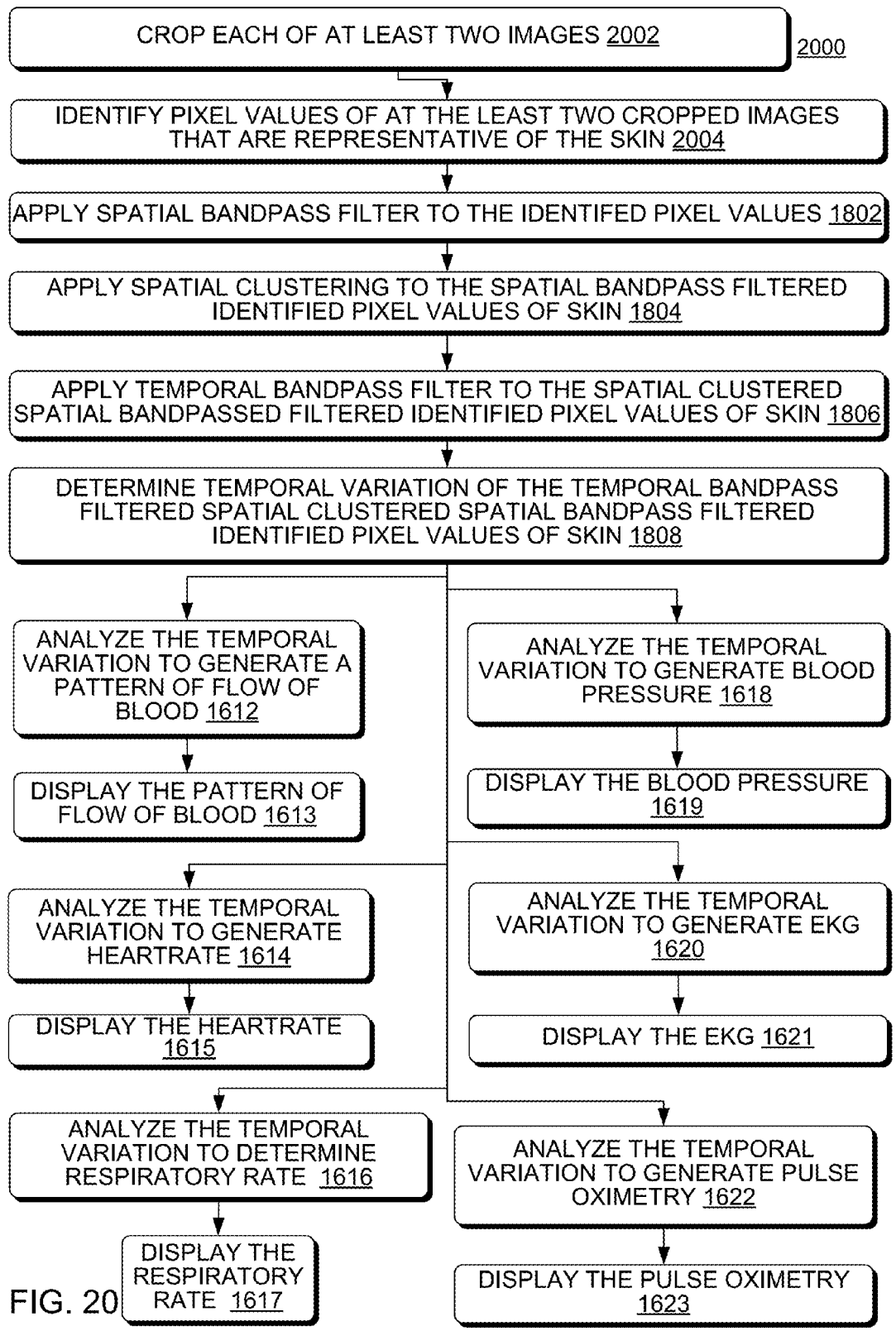
FIG. 20 is a flowchart of a method of motion amplification from which to generate and communicate biological vital signs, according to an implementation.

FIG. 20 is a flowchart of a method 2000 of motion amplification from which to generate and communicate biological vital signs, according to an implementation. Method 2000 analyzes the temporal and spatial variations in digital images of an animal subject in order to generate and communicate the biological vital signs.

In some implementations, method 2000 includes cropping at least two images to exclude areas that do not include a skin region, at block 2002. For example, the excluded area can be a perimeter area around the center of each image, so that an outside border area of the image is excluded. In some implementations of cropping out the border, about 72% of the width and about 72% of the height of each image is cropped out, leaving only 7.8% of the original uncropped image, which eliminates about $^{11}/_{12}$ of each image and reduces the amount of processing time for the remainder of the actions in this process by about 12-fold. This one action alone at block 2002 in method 2000 can reduce the processing time of plurality of images 124 in comparison to method 1800 from 4 minutes to 30 seconds, which is of significant difference to the health workers who used devices that implement method 2000. In some implementations, the remaining area of the image after cropping in a square area and in other implementation the remaining area after cropping is a circular area. Depending upon the topography and shape of the area in the images that has the most pertinent portion of the imaged subject, different geometries and sizes are most beneficial. The action of cropping the images at block 2002 can be applied at the beginning of methods 1600, 1700, 1800 and 1900 in FIGS. 16, 17, 18 and 19, respectively. In other implementations of apparatus 700, 800, 900, 1000, 1100, 1200, 1300, 1400 and 1500, a cropper module that performs action 2002 is placed at the beginning of the modules to greatly decrease processing time of the apparatus.

In some implementations, method 2000 includes identifying pixel values of the at least two or more cropped images that are representative of the skin, at block 2004. Some implementations of identifying pixel values that are representative of the skin include performing an automatic seed point based clustering process on the least two images.

In some implementations, method 2000 includes applying a spatial bandpass filter to the identified pixel values, at block 1802. In some implementations, the spatial filter in block 1802 is a two-dimensional spatial Fourier Transform, a high pass filter, a low pass filter, a bandpass filter or a weighted bandpass filter.

In some implementations, method 2000 includes applying spatial clustering to the spatial bandpass filtered identified pixel values of skin, at block 1804. In some implementations the spatial clustering includes fuzzy clustering, k-means clustering, expectation-maximization process, Ward's method or seed point based clustering.

In some implementations, method 2000 includes applying a temporal bandpass filter to the spatial clustered spatial bandpass filtered identified pixel values of skin, at block 1806. In some implementations, the temporal bandpass filter in block 1806 is a one-dimensional spatial Fourier Transform, a high pass filter, a low pass filter, a bandpass filter or a weighted bandpass filter.

In some implementations, method 2000 includes determining temporal variation of the temporal bandpass filtered spatial clustered spatial bandpass filtered identified pixel values of skin, at block 1808.

In some implementations, method 2000 includes analyzing the temporal variation to generate and visually display a pattern of flow of blood, at block 1612. In some implementations, the pattern flow of blood is generated from motion changes in the pixels and the temporal variation of color changes in the skin. In some implementations, method 2000 includes displaying the pattern of flow of blood for review by a healthcare worker, at block 1613.

In some implementations, method 2000 includes analyzing the temporal variation to generate heartrate, at block 1614. In some implementations, the heartrate is generated from the frequency spectrum of the temporal variation in a frequency range for heart beats, such as (0-10 Hertz). In some implementations, method 2000 includes displaying the heartrate for review by a healthcare worker, at block 1615.

In some implementations, method 2000 includes analyzing the temporal variation to determine respiratory rate, at block 1616. In some implementations, the respiratory rate is generated from the motion of the pixels in a frequency range for respiration (0-5 Hertz). In some implementations, method 2000 includes displaying the respiratory rate for review by a healthcare worker, at block 1617.

In some implementations, method 2000 includes analyzing the temporal variation to generate blood pressure, at block 1618. In some implementations, the blood pressure is generated by analyzing the motion of the pixels and the color changes based on the clustering process and potentially temporal data from the infrared sensor. In some implementations, method 2000 includes displaying the blood pressure for review by a healthcare worker, at block 1619.

In some implementations, method 2000 includes analyzing the temporal variation to generate EKG, at block 1620. In some implementations, method 2000 includes displaying the EKG for review by a healthcare worker, at block 1621.

In some implementations, method 2000 includes analyzing the temporal variation to generate pulse oximetry, at block 1622. In some implementations, the pulse oximetry is generated by analyzing the temporal color changes based in conjunction with the k-means clustering process and potentially temporal data from the infrared sensor. In some implementations, method 2000 includes displaying the pulse oximetry for review by a healthcare worker, at block 1623.

In some implementations, methods 1600-2000 are implemented as a sequence of instructions which, when executed by a microprocessor 102 in FIG. 1-3, microprocessor 2404 In FIG. 24, main processor 2102 in FIG. 21 or processing unit 2204 in FIG. 22, cause the processor to perform the respective method. In other implementations, methods 1600-2000 are implemented as a computer-accessible medium having computer executable instructions capable of directing a microprocessor, such as microprocessor 102 in FIG. 1-3, microprocessor 2404 in FIG. 24, main processor 2102 in FIG. 21 or processing unit 2204 in FIG. 22, to perform the respective method. In different implementations, the medium is a magnetic medium, an electronic medium, or an optical medium.

Hardware and Operating Environment

FIG. 21 is a block diagram of a hand-held device 2100, according to an implementation. The hand-held device 2100 may also have the capability to allow voice communication. Depending on the functionality provided by the hand-held device 2100, the hand-held device 2100 may be referred to as a data messaging device, a two-way pager, a cellular telephone with data messaging capabilities, a wireless Internet appliance, or a data communication device (with or without telephony capabilities).

The hand-held device 2100 includes a number of modules such as a main processor 2102 that controls the overall operation of the hand-held device 2100. Communication functions, including data and voice communications, are performed through a communication subsystem 2104. The communication subsystem 2104 receives messages from and sends messages to wireless networks 2105. In other implementations of the hand-held device 2100, the communication subsystem 2104 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 2104 with the wireless network 2105 represents one or more different Radio Frequency (RF) channels. With newer network protocols, these channels are capable of supporting both circuit switched voice communications and packet switched data communications.

The main processor 2102 also interacts with additional subsystems such as a Random Access Memory (RAM) 2106, a flash memory 2108, a display 2110, an auxiliary input/output (I/O) subsystem 2112, a data port 2114, a keyboard 2116, a speaker 2118, a microphone 2120, short-range communications subsystem 2122 and other device subsystems 2124. In some implementations, the flash memory 2108 includes a hybrid femtocell/Wi-Fi protocol stack 2109. The stack 2109 supports authentication and authorization between the hand-held device 2100 into a shared Wi-Fi network and both a 3G and 4G mobile networks.

Some of the subsystems of the hand-held device 2100 perform communication-related functions, whereas other subsystems may provide "resident" or on-device functions. By way of example, the display 2110 and the keyboard 2116 may be used for both communication-related functions, such as entering a text message for transmission over the wireless network 2105, and device-resident functions such as a calculator or task list.

The hand-held device 2100 can transmit and receive communication signals over the wireless network 2105 after required network registration or activation procedures have been completed. Network access is associated with a subscriber or user of the hand-held device 2100. To identify a subscriber, the hand-held device 2100 requires a SIM/RUIM card 2126 (i.e. Subscriber Identity Module or a Removable User Identity Module) to be inserted into a SIM/RUIM interface 2128 in order to communicate with a network. The SIM card or RUIM 2126 is one type of a conventional "smart card" that can be used to identify a subscriber of the hand-held device 2100 and to personalize the hand-held device 2100, among other things. Without the SIM card 2126, the hand-held device 2100 is not fully operational for communication with the wireless network 2105. By inserting the SIM card/RUIM 2126 into the SIM/RUIM interface 2128, a subscriber can access all subscribed services. Services may include: web browsing and messaging such as e-mail, voice mail, Short Message Service (SMS), and Multimedia Messaging Services (MMS). More advanced services may include: point of sale, field service and sales force automation. The SIM card/RUIM 2126 includes a processor and memory for storing information. Once the SIM card/RUIM 2126 is inserted into the SIM/RUIM interface 2128, the SIM is coupled to the main processor 2102. In order to identify the subscriber, the SIM card/RUIM 2126 can include some user parameters such as an International Mobile Subscriber Identity (IMSI). An advantage of using the SIM card/RUIM 2126 is that a subscriber is not necessarily bound by any single physical mobile device. The SIM card/RUIM 2126 may store additional subscriber information for the hand-held device 2100 as well, including datebook (or calendar) information and recent call information. Alternatively, user identification information can also be programmed into the flash memory 2108.

The hand-held device 2100 is a battery-powered device and includes a battery interface 2132 for receiving one or more rechargeable batteries 2130. In one or more implementations, the battery 2130 can be a smart battery with an embedded microprocessor. The battery interface 2132 is coupled to a regulator 2133, which assists the battery 2130 in providing power V+ to the hand-held device 2100. Although current technology makes use of a battery, future technologies such as micro fuel cells may provide the power to the hand-held device 2100.

The hand-held device 2100 also includes an operating system 2134 and modules 2136 to 2149 which are described in more detail below. The operating system 2134 and the modules 2136 to 2149 that are executed by the main processor 2102 are typically stored in a persistent nonvolatile medium such as the flash memory 2108, which may alternatively be a read-only memory (ROM) or similar storage element (not shown). Those skilled in the art will appreciate that portions of the operating system 2134 and the modules 2136 to 2149, such as specific device applications, or parts thereof, may be temporarily loaded into a volatile store such as the RAM 2106. Other modules can also be included.

The subset of modules 2136 that control basic device operations, including data and voice communication applications, will normally be installed on the hand-held device 2100 during its manufacture. Other modules include a message application 2138 that can be any suitable module that allows a user of the hand-held device 2100 to transmit and receive electronic messages. Various alternatives exist for the message application 2138 as is well known to those skilled in the art. Messages that have been sent or received by the user are typically stored in the flash memory 2108 of the hand-held device 2100 or some other suitable storage element in the hand-held device 2100. In one or more implementations, some of the sent and received messages may be stored remotely from the hand-held device 2100 such as in a data store of an associated host system with which the hand-held device 2100 communicates.

The modules can further include a device state module 2140, a Personal Information Manager (PIM) 2142, and other suitable modules (not shown). The device state module 2140 provides persistence, i.e. the device state module 2140 ensures that important device data is stored in persistent memory, such as the flash memory 2108, so that the data is not lost when the hand-held device 2100 is turned off or loses power.

The PIM 2142 includes functionality for organizing and managing data items of interest to the user, such as, but not limited to, e-mail, contacts, calendar events, voice mails, appointments, and task items. A PIM application has the ability to transmit and receive data items via the wireless network 2105. PIM data items may be seamlessly integrated, synchronized, and updated via the wireless network 2105 with the hand-held device 2100 subscriber's corresponding data items stored and/or associated with a host computer system. This functionality creates a mirrored host computer on the hand-held device 2100 with respect to such items. This can be particularly advantageous when the host computer system is the hand-held device 2100 subscriber's office computer system.

The hand-held device 2100 also includes a connect module 2144, and an IT policy module 2146. The connect module 2144 implements the communication protocols that are required for the hand-held device 2100 to communicate with the wireless infrastructure and any host system, such as an enterprise system, with which the hand-held device 2100 is authorized to interface. Examples of a wireless infrastructure and an enterprise system are given in FIGS. 21 and 22, which are described in more detail below.

The connect module 2144 includes a set of APIs that can be integrated with the hand-held device 2100 to allow the hand-held device 2100 to use any number of services associated with the enterprise system. The connect module 2144 allows the hand-held device 2100 to establish an end-to-end secure, authenticated communication pipe with the host system. A subset of applications for which access is provided by the connect module 2144 can be used to pass IT policy commands from the host system to the hand-held device 2100. This can be done in a wireless or wired manner. These instructions can then be passed to the IT policy module 2146 to modify the configuration of the hand-held device 2100. Alternatively, in some cases, the IT policy update can also be done over a wired connection.

The IT policy module 2146 receives IT policy data that encodes the IT policy. The IT policy module 2146 then ensures that the IT policy data is authenticated by the hand-held device 2100. The IT policy data can then be stored in the flash memory 2106 in its native form. After the IT policy data is stored, a global notification can be sent by the IT policy module 2146 to all of the applications residing on the hand-held device 2100. Applications for which the IT policy may be applicable then respond by reading the IT policy data to look for IT policy rules that are applicable.

The IT policy module 2146 can include a parser 2147, which can be used by the applications to read the IT policy rules. In some cases, another module or application can provide the parser. Grouped IT policy rules, described in more detail below, are retrieved as byte streams, which are then sent (recursively) into the parser to determine the values of each IT policy rule defined within the grouped IT policy rule. In one or more implementations, the IT policy module 2146 can determine which applications are affected by the IT policy data and transmit a notification to only those applications. In either of these cases, for applications that are not being executed by the main processor 2102 at the time of the notification, the applications can call the parser or the IT policy module 2146 when the applications are executed to determine if there are any relevant IT policy rules in the newly received IT policy data.

All applications that support rules in the IT Policy are coded to know the type of data to expect. For example, the value that is set for the "WEP User Name" IT policy rule is known to be a string; therefore the value in the IT policy data that corresponds to this rule is interpreted as a string. As another example, the setting for the "Set Maximum Password Attempts" IT policy rule is known to be an integer, and therefore the value in the IT policy data that corresponds to this rule is interpreted as such.

After the IT policy rules have been applied to the applicable applications or configuration files, the IT policy module 2146 sends an acknowledgement back to the host system to indicate that the IT policy data was received and successfully applied.

The programs 2137 can also include a temporal-variation-amplifier 2148 and a vital sign generator 2149. In some implementations, the temporal-variation-amplifier 2148 includes a skin-pixel-identifier 702, a frequency-filter 706, a regional facial clusterial module 708 and a frequency filter 710 as in FIGS. 7 and 8. In some implementations, the temporal-variation-amplifier 2148 includes a skin-pixel-identifier 702, a spatial bandpass-filter 902, regional facial clusterial module 708 and a temporal bandpass filter 904 as in FIG. 9. In some implementations, the temporal-variation-amplifier 2148 includes a pixel-examiner 1002, a temporal variation determiner 1006 and signal processor 1008 as in FIG. 10. In some implementations, the temporal-variation-amplifier 2148 includes a skin-pixel-identification module 1102, a frequency-filter module 1108, spatial-cluster module 1112 and a frequency filter module 1116 as in FIGS. 11 and 12. In some implementations, the temporal-variation-amplifier module 1102, a spatial bandpass filter module 1402, a spatial-cluster module 1112 and a temporal bandpass filter module 1406 as in FIG. 14. In some implementations, the temporal-variation-amplifier 2148 includes a pixel examination-module 1502, a temporal variation determiner module 1506 and a signal processing module 1510 as in FIG. 15. The camera 122 captures images 124 and the vital sign generator 2149 generates the vital sign(s) 716 that is displayed by display 2110 or transmitted by communication subsystem 2104 or short-range communications subsystem 2122, enunciated by speaker 2118 or stored by flash memory 2108.

Other types of modules can also be installed on the hand-held device 2100. These modules can be third party modules, which are added after the manufacture of the hand-held device 2100. Examples of third party applications include games, calculators, utilities, etc.

The additional applications can be loaded onto the hand-held device 2100 through at least one of the wireless network 2105, the auxiliary I/O subsystem 2112, the data port 2114, the short-range communications subsystem 2122, or any other suitable device subsystem 2124. This flexibility in application installation increases the functionality of the hand-held device 2100 and may provide enhanced on-device functions, communication-related functions, or both. For example, secure communication applications may enable electronic commerce functions and other such financial transactions to be performed using the hand-held device 2100.

The data port 2114 enables a subscriber to set preferences through an external device or module and extends the capabilities of the hand-held device 2100 by providing for information or module downloads to the hand-held device 2100 other than through a wireless communication network.

The alternate download path may, for example, be used to load an encryption key onto the hand-held device 2100 through a direct and thus reliable and trusted connection to provide secure device communication.

The data port 2114 can be any suitable port that enables data communication between the hand-held device 2100 and another computing device. The data port 2114 can be a serial or a parallel port. In some instances, the data port 2114 can be a USB port that includes data lines for data transfer and a supply line that can provide a charging current to charge the battery 2130 of the hand-held device 2100.

The short-range communications subsystem 2122 provides for communication between the hand-held device 2100 and different systems or devices, without the use of the wireless network 2105. For example, the subsystem 2122 may include an infrared device and associated circuits and modules for short-range communication. Examples of short-range communication standards include standards developed by the Infrared Data Association (IrDA), Bluetooth, and the 802.11 family of standards developed by IEEE.

Bluetooth is a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1994, Bluetooth was originally conceived as a wireless alternative to RS-232 data cables. Blutooth can connect several devices, overcoming problems of synchronization. Bluetooth operates in the range of 2400-2483.5 MHz (including guard bands), which is in the globally unlicensed Industrial, Scientific and Medical (ISM) 2.4 GHz short-range radio frequency band. Bluetooth uses a radio technology called frequency-hopping spread spectrum. The transmitted data is divided into packets and each packet is transmitted on one of the 79 designated Bluetooth channels. Each channel has a bandwidth of 1 MHz. The first channel starts at 2402 MHz and continues up to 2480 MHz in 1 MHz steps. The first channel usually performs 1600 hops per second, with Adaptive Frequency-Hopping (AFH) enabled. Originally Gaussian frequency-shift keying (GFSK) modulation was the only modulation scheme available; subsequently, since the introduction of Bluetooth 2.0+EDR, $\pi/4$-DQPSK and 8DPSK modulation may also be used between compatible devices. Devices functioning with GFSK are said to be operating in basic rate (BR) mode where an instantaneous data rate of 1 Mbit/s is possible. The term Enhanced Data Rate (EDR) is used to describe $\pi/4$-DPSK and 8DPSK schemes, each giving 2 and 3 Mbit/s respectively. The combination of these (BR and EDR) modes in Bluetooth radio technology is classified as a "BR/EDR radio". Bluetooth is a packet-based protocol with a master-slave structure. One master may communicate with up to 7 slaves in a piconet; all devices share the master's clock. Packet exchange is based on the basic clock, defined by the master, which ticks at 312.5 µs intervals. Two clock ticks make up a slot of 625 µs; two slots make up a slot pair of 1250 µs. In the simple case of single-slot packets the master transmits in even slots and receives in odd slots; the slave, conversely, receives in even slots and transmits in odd slots. Packets may be 1, 3 or 5 slots long but in all cases the master transmit will begin in even slots and the slave transmit in odd slots. A master Bluetooth device can communicate with a maximum of seven devices in a piconet (an ad-hoc computer network using Bluetooth technology), though not all devices reach this maximum. The devices can switch roles, by agreement, and the slave can become the master (for example, a headset initiating a connection to a phone will necessarily begin as master, as initiator of the connection; but may subsequently prefer to be slave). The Bluetooth Core Specification provides for the connection of two or more piconets to form a scatternet, in which certain devices simultaneously play the master role in one piconet and the slave role in another. At any given time, data can be transferred between the master and one other device (except for the little-used broadcast mode. The master chooses which slave device to address; typically, the master switches rapidly from one device to another in a round-robin fashion. Since the master chooses which slave to address, whereas a slave is (in theory) supposed to listen in each receive slot, being a master is a lighter burden than being a slave. Being a master of seven slaves is possible; being a slave of more than one master is difficult. Many of the services offered over Bluetooth can expose private data or allow the connecting party to control the Bluetooth device. For security reasons it is necessary to be able to recognize specific devices and thus enable control over which devices are allowed to connect to a given Bluetooth device. At the same time, it is useful for Bluetooth devices to be able to establish a connection without user intervention (for example, as soon as the Bluetooth devices of each other are in range). To resolve this conflict, Bluetooth uses a process called bonding, and a bond is created through a process called pairing. The pairing process is triggered either by a specific request from a user to create a bond (for example, the user explicitly requests to "Add a Bluetooth device"), or the pairing process is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices. Once pairing successfully completes, a bond will have been formed between the two devices, enabling those two devices to connect to each other in the future without requiring the pairing process in order to confirm the identity of the devices. When desired, the bonding relationship can later be removed by the user. Secure Simple Pairing (SSP): This is required by Bluetooth v2.1, although a Bluetooth v2.1 device may only use legacy pairing to interoperate with a v2.0 or earlier device. Secure Simple Pairing uses a form of public key cryptography, and some types can help protect against man in the middle, or MITM attacks. SSP has the following characteristics: Just works: As implied by the name, this method just works. No user interaction is required; however, a device may prompt the user to confirm the pairing process. This method is typically used by headsets with very limited IO capabilities, and is more secure than the fixed PIN mechanism which is typically used for legacy pairing by this set of limited devices. This method provides no man in the middle (MITM) protection. Numeric comparison: If both devices have a display and at least one can accept a binary Yes/No user input, both devices may use Numeric Comparison. This method displays a 6-digit numeric code on each device. The user should compare the numbers to ensure that the numbers are identical. If the comparison succeeds, the user(s) should confirm pairing on the device(s) that can accept an input. This method provides MITM protection, assuming the user confirms on both devices and actually performs the comparison properly. Passkey Entry: This method may be used between a device with a display and a device with numeric keypad entry (such as a keyboard), or two devices with numeric keypad entry. In the first case, the display is used to show a 6-digit numeric code to the user, who then enters the code on the keypad. In the second case, the user of each device enters the same 6-digit number. Both of these cases provide MITM protection. Out of band (OOB): This method uses an external means of communication, such as Near Field Communication (NFC) to exchange some information used in the pairing process. Pairing is completed using the Bluetooth radio, but requires information from the OOB mechanism. This provides only the level of MITM protection that is present in the OOB mechanism. SSP is considered simple for the following reasons: In most cases, SSP does not require a user to generate a passkey. For use-cases not requiring MITM protection, user interaction can be eliminated. For numeric comparison, MITM protection can be achieved with a simple equality comparison by the user. Using OOB with NFC enables pairing when devices simply get close, rather than requiring a lengthy discovery process.

In use, a received signal such as a text message, an e-mail message, or web page download will be processed by the communication subsystem 2104 and input to the main processor 2102. The main processor 2102 will then process the received signal for output to the display 2110 or alternatively to the auxiliary I/O subsystem 2112. A subscriber may also compose data items, such as e-mail messages, for example, using the keyboard 2116 in conjunction with the display 2110 and possibly the auxiliary I/O subsystem 2112. The auxiliary subsystem 2112 may include devices such as: a touch screen, mouse, track ball, infrared fingerprint detector, or a roller wheel with dynamic button pressing capability. The keyboard 2116 is preferably an alphanumeric keyboard and/or telephone-type keypad. However, other types of keyboards may also be used. A composed item may be transmitted over the wireless network 2105 through the communication subsystem 2104.

For voice communications, the overall operation of the hand-held device 2100 is substantially similar, except that the received signals are output to the speaker 2118, and signals for transmission are generated by the microphone 2120. Alternative voice or audio I/O subsystems, such as a voice message recording subsystem, can also be implemented on the hand-held device 2100. Although voice or audio signal output is accomplished primarily through the speaker 2118, the display 2110 can also be used to provide additional information such as the identity of a calling party, duration of a voice call, or other voice call related information.

FIG. 22 is a block diagram of a hardware and operating environment 2200 in which different implementations can be practiced. The description of FIG. 22 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

FIG. 22 illustrates an example of a computer environment 2200 useful in the context of the environment of FIG. 1-9, in accordance with an implementation. The computer environment 2200 includes a computation resource 2202 capable of implementing the processes described herein. It will be appreciated that other devices can alternatively used that include more modules, or fewer modules, than those illustrated in FIG. 22.

The illustrated operating environment 2200 is only one example of a suitable operating environment, and the example described with reference to FIG. 22 is not intended to suggest any limitation as to the scope of use or functionality of the implementations of this disclosure. Other well-known computing systems, environments, and/or configurations can be suitable for implementation and/or application of the subject matter disclosed herein.

The computation resource 2202 includes one or more processors or processing units 2204, a system memory 2206, and a bus 2208 that couples various system modules including the system memory 2206 to processing unit 2204 and other elements in the environment 2200. The bus 2208 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 2206 includes nonvolatile read-only memory (ROM) 2210 and random access memory (RAM) 2212, which can or can not include volatile memory elements. A basic input/output system (BIOS) 2214, containing the elementary routines that help to transfer information between elements within computation resource 2202 and with external items, typically invoked into operating memory during start-up, is stored in ROM 2210.

The computation resource 2202 further can include a non-volatile read/write memory 2216, represented in FIG. 22 as a hard disk drive, coupled to bus 2208 via a data media interface 2217 (e.g., a SCSI, ATA, or other type of interface); a magnetic disk drive (not shown) for reading from, and/or writing to, a removable magnetic disk 2220 and an optical disk drive (not shown) for reading from, and/or writing to, a removable optical disk 2226 such as a CD, DVD, or other optical media.

The non-volatile read/write memory 2216 and associated computer-readable media provide nonvolatile storage of computer-readable instructions, data structures, program modules and other data for the computation resource 2202. Although the exemplary environment 2200 is described herein as employing a non-volatile read/write memory 2216, a removable magnetic disk 2220 and a removable optical disk 2226, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 2216, magnetic disk 2220, optical disk 2226, ROM 2210, or RAM 2212, including an operating system 2230, one or more application programs 2232, program modules 2234 and program data 2236. Examples of computer operating systems conventionally employed include the NUCLEUS® operating system, the LINUX® operating system, and others, for example, providing capability for supporting application programs 2232 using, for example, code modules written in the C++® computer programming language. The application programs 2232 and/or the program modules 2234 can also include a temporal-variation-amplifier (as shown in 2148 in FIG. 21) and a vital sign generator (as shown in 2149 in FIG. 22). In some implementations, the temporal-variation-amplifier 2148 in the application programs 2232 and/or the program modules 2234 includes a skin-pixel-identifier 702, a frequency-filter 706, regional facial clusterial module 708 and a frequency filter 710 as in FIGS. 7 and 8. In some implementations, the temporal-variation-amplifier 2148 in application programs 2232 and/or the program modules 2234 includes a skin-pixel-identifier 702, a spatial bandpass-filter 902, regional facial clusterial module 708 and a temporal bandpass filter 904 as in FIG. 9. In some implementations, the temporal-variation-amplifier 2148 in the application programs 2232 and/or the program modules 2234 includes a pixel-examiner 1002, a temporal variation determiner 1006 and signal processor 1008 as in FIG. 10. In some implementations, the temporal-variation-amplifier 2148 in the application programs 2232 and/or the program modules 2234 includes a skin-pixel-identification module 1102, a frequency-filter module 1108, spatial-cluster module 1112 and a frequency filter module 1116 as in FIGS. 11 and 12. In some implementations, the temporal-variation-amplifier 2148 in the application programs 2232 and/or the program modules 2234 includes a skin-pixel-identification module 1102, a spatial bandpass filter module 1402, a spatial-cluster module 1112 and a temporal bandpass filter module 1406 as in FIG. 14. In some implementations, the temporal-variation-amplifier 2148 in the application programs 2232 and/or the program modules 2234 includes a pixel examination-module 1502, a temporal variation determiner module 1506 and a signal processing module 1510 as in FIG. 15. The camera 122 captures images 124 that are processed by the temporal-variation-amplifier 2148 and the vital sign generator 2149 to generate the vital sign(s) 716 that is displayed by display 2250 or transmitted by computation resource 2202, enunciated by a speaker or stored in program data 2236.

A user can enter commands and information into computation resource 2202 through input devices such as input media 2238 (e.g., keyboard/keypad, tactile input or pointing device, mouse, foot-operated switching apparatus, joystick, touchscreen or touchpad, microphone, antenna etc.). Such input devices 2238 are coupled to the processing unit 2204 through a conventional input/output interface 2242 that is, in turn, coupled to the system bus. Display 2250 or other type of display device is also coupled to the system bus 2208 via an interface, such as a video adapter 2252.

The computation resource 2202 can include capability for operating in a networked environment using logical connections to one or more remote computers, such as a remote computer 2260. The remote computer 2260 can be a personal computer, a server, a router, a network PC, a peer device or other common network node, and typically includes many or all of the elements described above relative to the computation resource 2202. In a networked environment, program modules depicted relative to the computation resource 2202, or portions thereof, can be stored in a remote memory storage device such as can be associated with the remote computer 2260. By way of example, remote application programs 2262 reside on a memory device of the remote computer 2260. The logical connections represented in FIG. 22 can include interface capabilities, e.g., such as interface capabilities in FIG. 5, a storage area network (SAN, not illustrated in FIG. 22), local area network (LAN) 2272 and/or a wide area network (WAN) 2274, but can also include other networks.

Such networking environments are commonplace in modern computer systems, and in association with intranets and the Internet. In certain implementations, the computation resource 2202 executes an Internet Web browser program (which can optionally be integrated into the operating system 2230), such as the "Internet Explorer®" Web browser manufactured and distributed by the Microsoft Corporation of Redmond, Wash.

When used in a LAN-coupled environment, the computation resource 2202 communicates with or through the local area network 2272 via a network interface or adapter 2276 and typically includes interfaces, such as a modem 2278, or other apparatus, for establishing communications with or through the WAN 2274, such as the Internet. The modem 2278, which can be internal or external, is coupled to the system bus 2208 via a serial port interface.

In a networked environment, program modules depicted relative to the computation resource 2202, or portions thereof, can be stored in remote memory apparatus. It will be appreciated that the network connections shown are exemplary, and other means of establishing a communications link between various computer systems and elements can be used.

A user of a computer can operate in a networked environment using logical connections to one or more remote computers, such as a remote computer 2260, which can be a personal computer, a server, a router, a network PC, a peer device or other common network node. Typically, a remote computer 2260 includes many or all of the elements described above relative to the computer 2200 of FIG. 22.

The computation resource 2202 typically includes at least some form of computer-readable media. Computer-readable media can be any available media that can be accessed by the computation resource 2202. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 2202.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

FIG. 23 is a representation of display 2300 that is presented on the display device of apparatus in FIG. 1-3, according to an implementation.

Some implementations of display 2300 include a representation of three detection modes 2302, a first detection mode being detection and display of surface temperature, a second detection mode being detection and display of body temperature and a third detection mode being detection and display of room temperature.

Some implementations of display 2300 include a representation of Celsius 2304 that is activated when the apparatus is in Celsius mode.

Some implementations of display 2300 include a representation of a sensed temperature 2306.

Some implementations of display 2300 include a representation of Fahrenheit 2308 that is activated when the apparatus is in Fahrenheit mode.

Some implementations of display 2300 include a representation of a mode 2310 of site temperature sensing, a first site mode being detection of an axillary surface temperature, a second site mode being detection of an oral temperature, a third site mode being detection of a rectal temperature and a fourth site mode being detection of a core temperature.

Some implementations of display 2300 include a representation of a temperature traffic light 2312, in which a green traffic light indicates that the temperature 120 is good; an amber traffic light indicates that the temperature 120 is low; and a red traffic light indicates that the temperature 120 is high.

Some implementations of display 2300 include a representation of a probe mode 2314 that is activated when the sensed temperature 2306 is from a contact sensor.

Some implementations of display 2300 include a representation of the current time/date 2316 of the apparatus.

FIG. 24-28 are schematics of the electronic components of a non-touch thermometer 2400 having a digital IR sensor. FIG. 24 is a portion of the schematic of the non-touch thermometer 2400 having a digital IR sensor, according to an implementation. As discussed above in regards to FIG. 2 and FIG. 3, thermal isolation of the digital IR sensor is an important feature. In second circuit board 2401, a digital IR sensor 2403 is thermally isolated from the heat of the microprocessor 2404 (shown in FIG. 25) through a first digital interface 2402. The digital IR sensor 2403 is not mounted on the same circuit board 2405 as the microprocessor 2404 (shown in FIG. 25) which reduces heat transfer from a first circuit board 2405 to the digital IR sensor 2403. The non-touch thermometer 2400 also includes a second circuit board 2401, the second circuit board 2401 including a second digital interface 2412, the second digital interface 2412 being operably coupled to the first digital interface 2402 and a digital infrared sensor 2403 being operably coupled to the second digital interface 2412, the digital infrared sensor 2403 having ports that provide only digital readout. The microprocessor 2404 (shown in FIG. 25) is operable to receive from the ports that provide only digital readout a digital signal that is representative of an infrared signal generated by the digital infrared sensor 2403 and the microprocessor 2404 (shown in FIG. 25) is operable to determine a temperature from the digital signal that is representative of the infrared signal. The first circuit board 2405 includes all of the components in FIG. 24, FIG. 25 and FIG. 26 other than the second circuit board 2401, the digital IR sensor 2403 and the second digital interface 2412.

Figure 25:
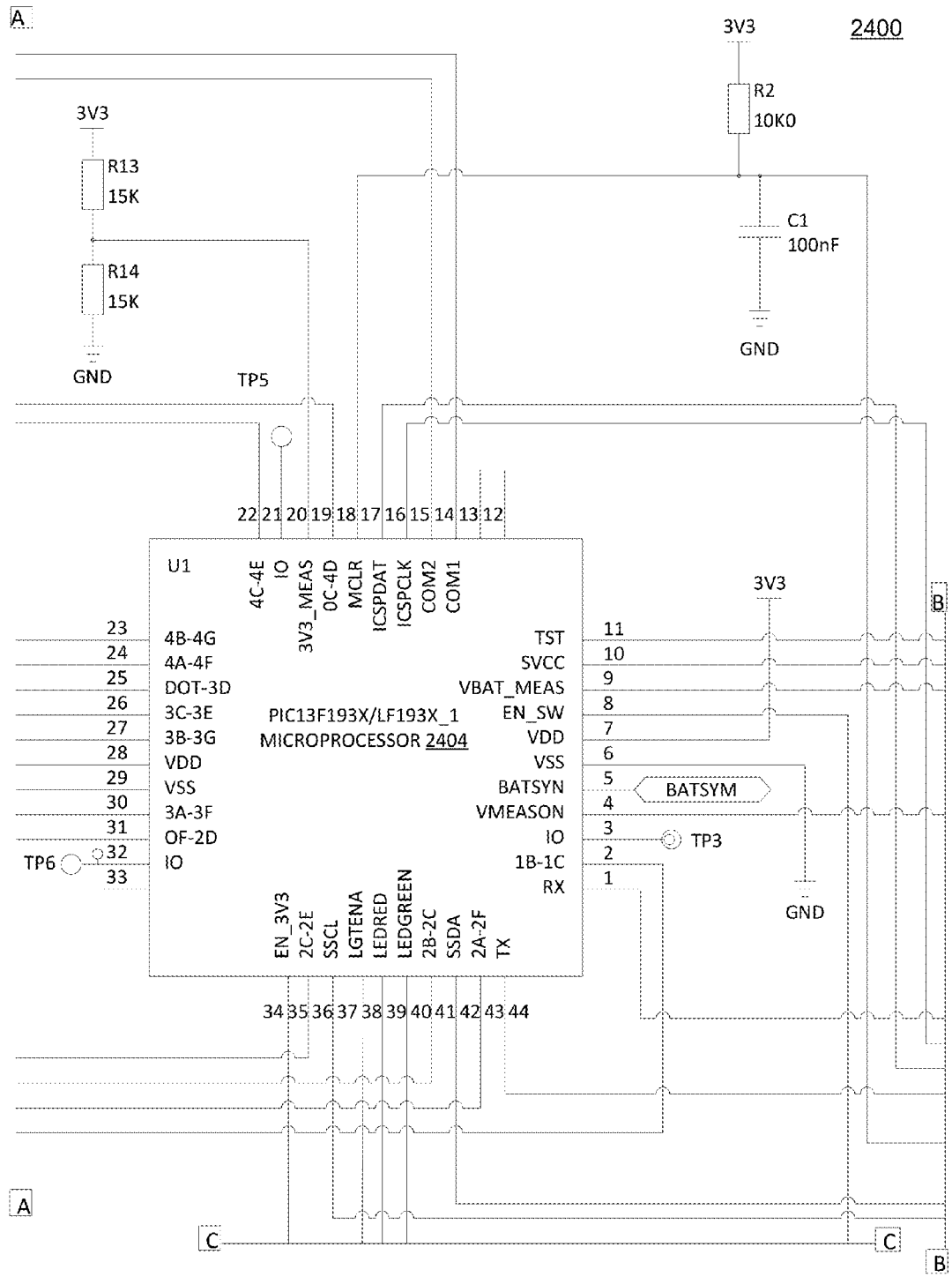
FIG. 25 is a portion of the schematic of the non-touch thermometer having the digital IR sensor, according to an implementation.

FIG. 25 is a portion of the schematic of the non-touch thermometer 2400 having the digital IR sensor, according to an implementation. A non-touch thermometer 2400 includes a first circuit board 2405, the first circuit board 2405 including the microprocessor 2404.

Figure 26:
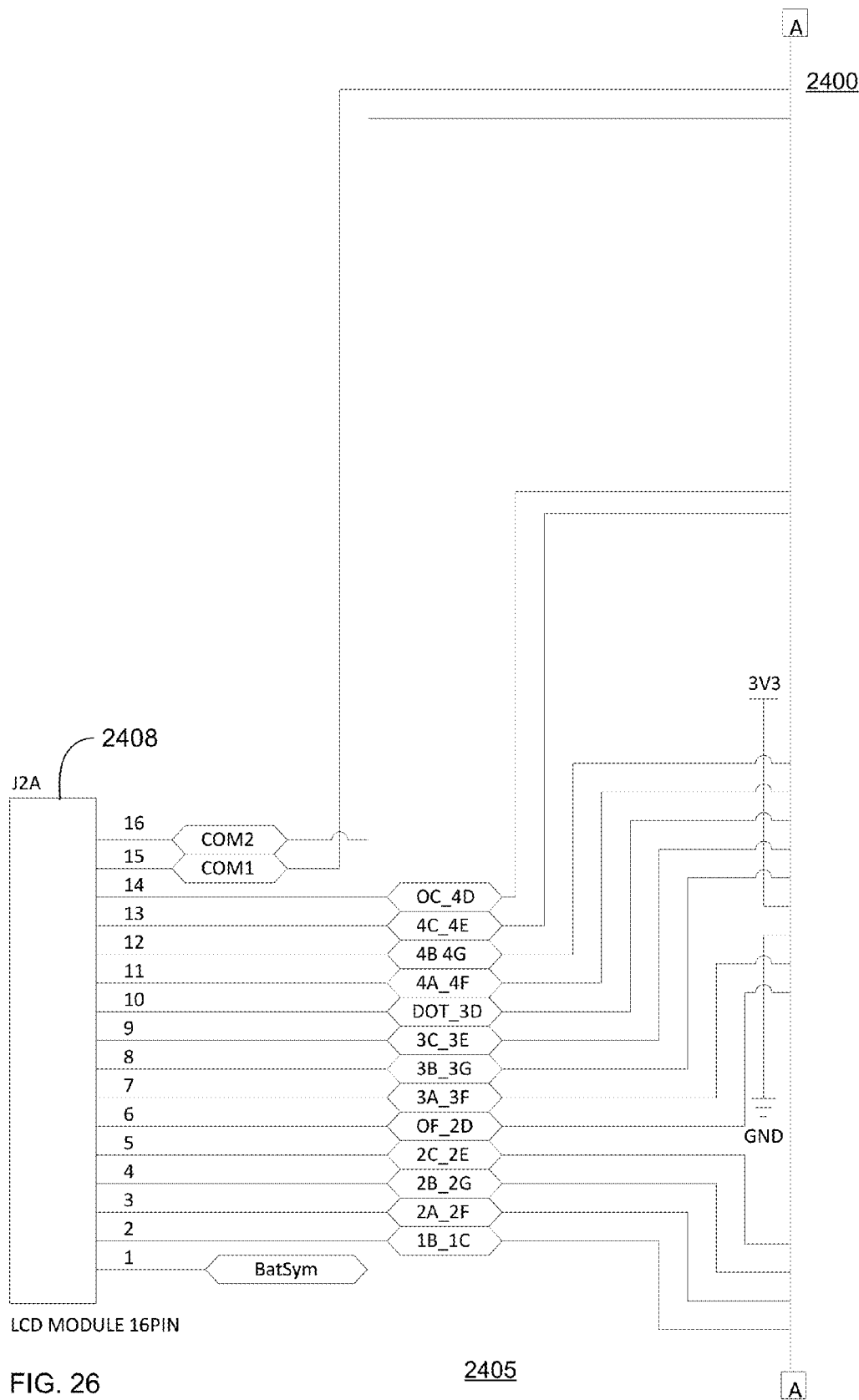
FIG. 26 is a portion of the schematic of the non-touch thermometer having the digital IR sensor, according to an implementation.

FIG. 26 is a portion of the schematic of the non-touch thermometer 2400 having the digital IR sensor, according to an implementation. The first circuit board 2405 includes a display device that is operably coupled to the microprocessor 2404 through a display interface 2408.

Figure 27:
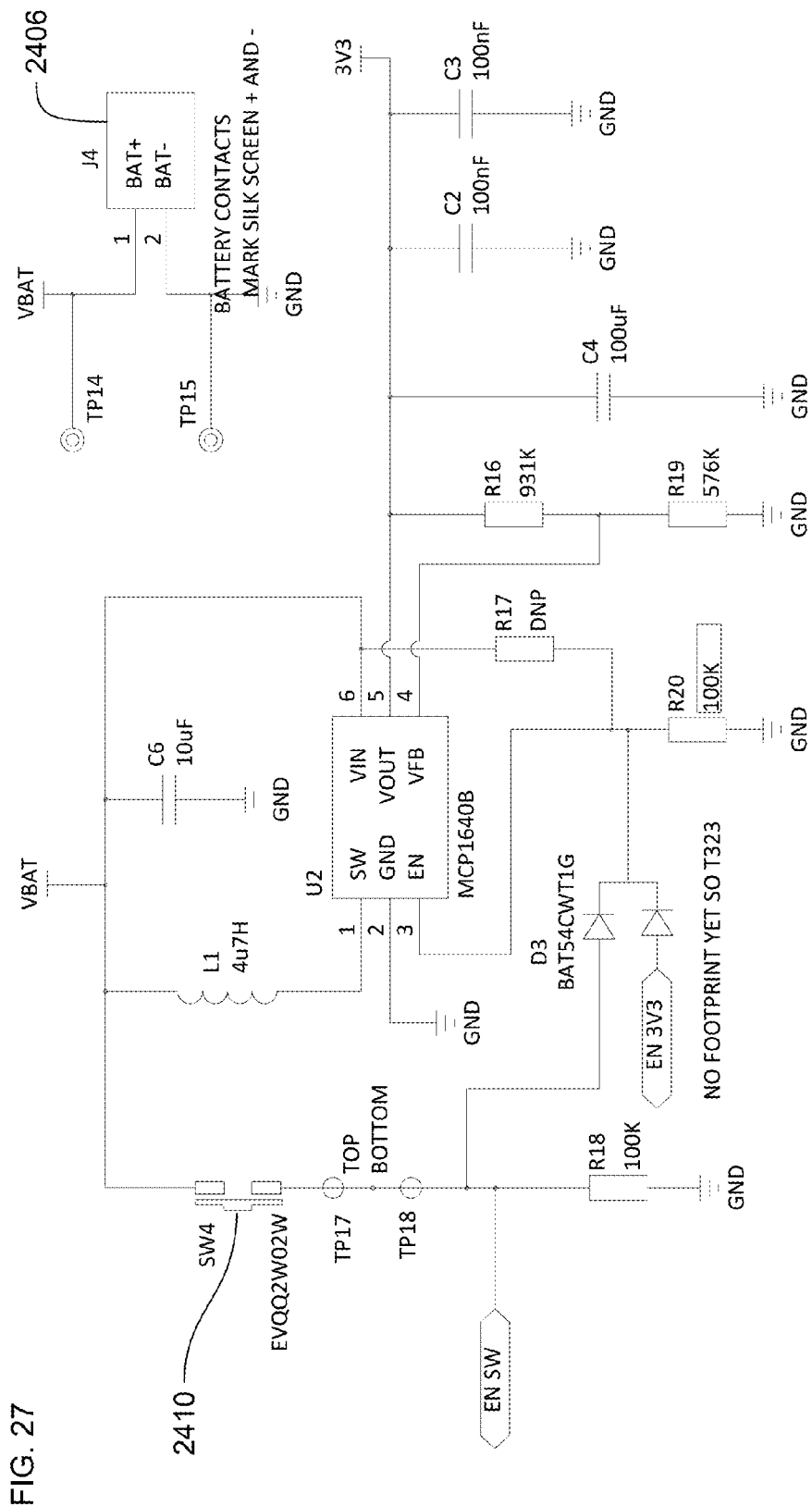
FIG. 27 is a circuit that is a portion of the schematic of the non-touch thermometer having the digital IR sensor, according to an implementation.

FIG. 27 is a circuit 2700 that is a portion of the schematic of the non-touch thermometer 2400 having the digital IR sensor, according to an implementation. Circuit 2700 includes a battery 2406 that is operably coupled to the microprocessor 2404, a single button 2410 that is operably coupled to the microprocessor 2404.

Figure 28:
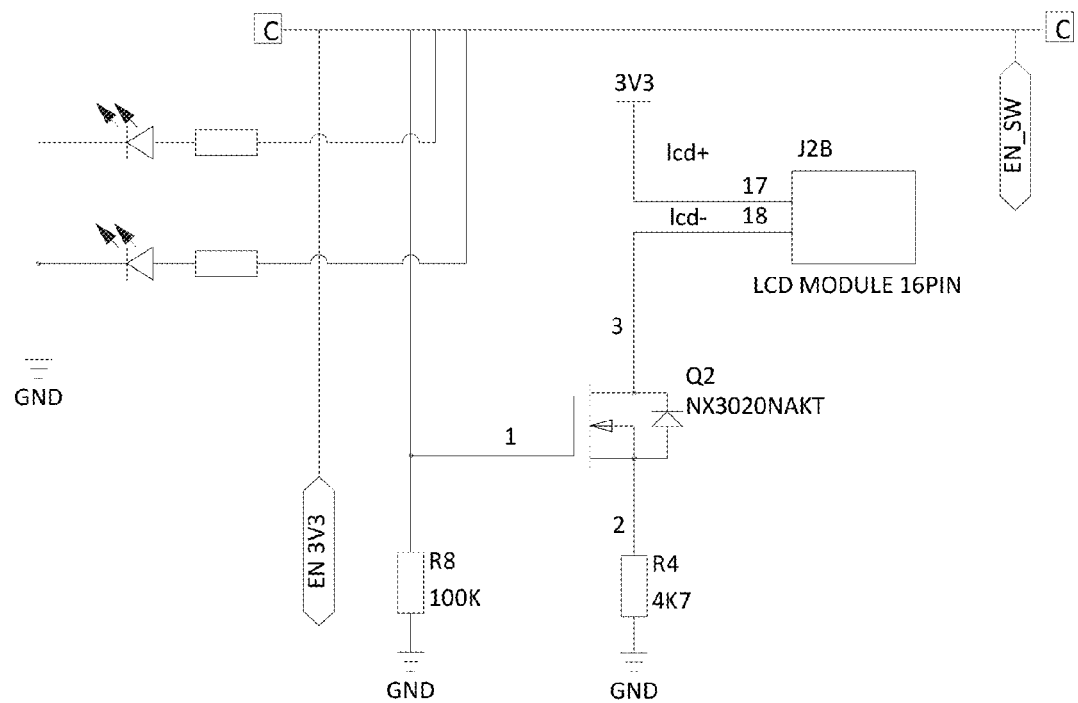
FIG. 28 is a circuit that is a portion of the schematic of the non-touch thermometer having the digital IR sensor, according to an implementation.

FIG. 28 is a circuit 2800 that is a portion of the schematic of the non-touch thermometer 2400 having the digital IR sensor, according to an implementation.

The non-touch thermometer further includes a housing, and where the battery 104 is fixedly attached to the housing. The non-touch thermometer where an exterior portion of the housing further includes: a magnet.

Conclusion

A non-touch thermometer that senses temperature from a digital infrared sensor is described. A technical effect of the apparatus is transmitting from the digital infrared sensor a digital signal representing a temperature without conversion from analog. Another technical effect of the apparatus and methods disclosed herein is generating a temporal variation of images from which a heartrate and the respiratory rate can be determined and displayed or stored. Although specific implementations are illustrated and described herein, it will be appreciated by those of ordinary skill in the art that any arrangement which is generated to achieve the same purpose may be substituted for the specific implementations shown. This application is intended to cover any adaptations or variations.

In particular, one of skill in the art will readily appreciate that the names of the methods and apparatus are not intended to limit implementations. Furthermore, additional methods and apparatus can be added to the modules, functions can be rearranged among the modules, and new modules to correspond to future enhancements and physical devices used in implementations can be introduced without departing from the scope of implementations. One of skill in the art will readily recognize that implementations are applicable to future non-touch temperature sensing devices, different temperature measuring sites on humans or animals and new display devices.

The terminology used in this application meant to include all temperature sensors, processors and operator environments and alternate technologies which provide the same functionality as described herein.

The invention claimed is:

1. A non-touch thermometer to measure temperature, the non-touch thermometer comprising:
   a microprocessor;
   a battery operably coupled to the microprocessor;
   a single button operably coupled to the microprocessor;
   a camera operably coupled to the microprocessor and providing at least two images to the microprocessor;
   a digital infrared sensor operably coupled to the microprocessor, the digital infrared sensor having ports that provide only digital readout, wherein no analog-to-digital converter is operably coupled between the digital infrared sensor and the microprocessor; and
   a display device operably coupled to the microprocessor, wherein the microprocessor is operable to receive from the ports that provide only digital readout a digital signal that is representative of an infrared signal detected by the digital infrared sensor and the microprocessor is operable to determine the temperature from the digital signal that is representative of the infrared signal and the microprocessor including a pixel-examination-module configured to examine pixel values of the at least two images, a temporal-variation module to determine temporal variation of the pixel values between the at least two images being below a particular threshold, a signal processing module configured to amplify the temporal variation resulting in amplified temporal variation, and a visualizer to visualize a pattern of flow of blood in the amplified temporal variation in the at least two images.

2. The non-touch thermometer of claim 1, wherein the display device further comprises:
a green traffic light operable to indicate that the temperature is good;
an amber traffic light operable to indicate that the temperature is low; and
a red traffic light operable to indicate that the temperature is high.

3. The non-touch thermometer of claim 1 further comprising:
a housing; and
wherein the battery is fixedly attached to the housing.

4. The non-touch thermometer of claim 3, wherein an exterior portion of the housing further comprises:
a magnet.

5. The non-touch thermometer of claim 1, wherein the digital infrared sensor further comprises:
a low noise amplifier, an analog-to-digital converter, a digital signal processor, and a pulse width modulator.

6. The non-touch thermometer of claim 1 further comprising:
the digital infrared sensor having no analog sensor readout ports.

7. The non-touch thermometer of claim 1, wherein the signal processing module is further configured to amplify variations of the pixel values between the at least two images.

8. The non-touch thermometer of claim 1, wherein the signal processing module performs temporal processing.

9. The non-touch thermometer of claim 8, wherein the temporal processing is a bandpass filter.

10. The non-touch thermometer of claim 9, wherein the bandpass filter is configured to analyze frequencies over time.

11. The non-touch thermometer of claim 1, wherein applying signal processing includes spatial processing.

12. A non-touch thermometer to measure temperature, the non-touch thermometer comprising:
a housing;
a microprocessor coupled to the housing;
a battery operably coupled to the microprocessor, and wherein the battery is fixedly attached to the housing;
a single button operably coupled to the microprocessor;
a camera operably coupled to the microprocessor and providing at least two images to the microprocessor;
a digital infrared sensor operably coupled to the microprocessor, the digital infrared sensor having only digital readout ports, the digital infrared sensor having no analog sensor readout ports; and
a display device operably coupled to the microprocessor, wherein the microprocessor is operable to receive from the digital readout ports a digital signal that is representative of an infrared signal detected by the digital infrared sensor and the microprocessor is operable to determine the temperature from the digital signal that is representative of the infrared signal and the microprocessor including a pixel-examination-module configured to examine pixel values of the at least two images, a temporal-variation module to determine temporal variation of the pixel values between the at least two images being below a particular threshold, a signal processing module configured to amplify the temporal variation resulting in amplified temporal variation, and a visualizer to visualize a pattern of flow of blood in the amplified temporal variation in the at least two images.

13. The non-touch thermometer of claim 12, wherein the display device further comprises:
a green traffic light operable to indicate that the temperature is good;
an amber traffic light operable to indicate that the temperature is low; and
a red traffic light operable to indicate that the temperature is high.

14. The non-touch thermometer of claim 12, wherein the digital infrared sensor further comprises:
a low noise amplifier, an analog-to-digital converter, a digital signal processor, and a pulse width modulator.

15. The non-touch thermometer of claim 12, wherein the signal processing module is further configured to amplify variations of the pixel values between the at least two images.

16. The non-touch thermometer of claim 12, wherein the signal processing module performs temporal processing.

17. The non-touch thermometer of claim 16, wherein the temporal processing is a bandpass filter.

18. The non-touch thermometer of claim 17, wherein the bandpass filter is configured to analyze frequencies over time.

19. The non-touch thermometer of claim 12, wherein applying signal processing includes spatial processing.

20. The non-touch thermometer of claim 19, wherein the spatial processing removes noise.

* * * * *